(12) United States Patent
Allan et al.

(10) Patent No.: US 9,890,134 B2
(45) Date of Patent: Feb. 13, 2018

(54) PROCESSES FOR PREPARING ANTIVIRAL COMPOUNDS

(71) Applicant: Gilead Pharmasset LLC, Foster City, CA (US)

(72) Inventors: Kevin M. Allan, San Francisco, CA (US); Shinji Fujimori, San Francisco, CA (US); Lars V. Heumann, Redwood City, CA (US); Grace May Huynh, San Mateo, CA (US); Katie Ann Keaton, Burlingame, CA (US); Chrisopher M. Levins, Redwood City, CA (US); Ganapati Reddy Pamulapati, San Ramon, CA (US); Benjamin James Roberts, San Francisco, CA (US); Keshab Sarma, Sunnyvale, CA (US); Martin Gerald Teresk, Parkville, MO (US); Xiang Wang, Foster City, CA (US); Scott Alan Wolckenhauer, Redwood City, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 0 days.

(21) Appl. No.: 15/582,224

(22) Filed: Apr. 28, 2017

(65) Prior Publication Data
US 2017/0283390 A1  Oct. 5, 2017

Related U.S. Application Data

(63) Continuation of application No. 14/733,139, filed on Jun. 8, 2015, now Pat. No. 9,670,187.

(60) Provisional application No. 62/010,813, filed on Jun. 11, 2014.

(51) Int. Cl.
*C07D 311/78* (2006.01)
*C07C 49/755* (2006.01)

(52) U.S. Cl.
CPC .......... *C07D 311/78* (2013.01); *C07C 49/755* (2013.01); *C07C 2602/10* (2017.05)

(58) Field of Classification Search
CPC .......................... C07C 49/755; C07D 311/78
See application file for complete search history.

(56) References Cited

FOREIGN PATENT DOCUMENTS

| CA | 2815082 A1 | 5/2013 |
|---|---|---|
| WO | WO-2013/075029 A1 | 5/2013 |

OTHER PUBLICATIONS

International Search Report & Written Opinion for PCT/US2015/034655, dated Oct. 2, 2015.

*Primary Examiner* — Laura L. Stockton
(74) *Attorney, Agent, or Firm* — Sheppard Mullin Richter & Hampton LLP

(57) ABSTRACT

The present disclosure provides processes for the preparation of a compound of formula:

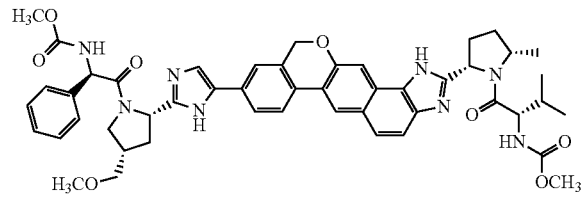

which is useful as an antiviral agent. The disclosure also provides compounds that are synthetic intermediates.

14 Claims, No Drawings

PROCESSES FOR PREPARING ANTIVIRAL COMPOUNDS

CROSS REFERENCE TO RELATED APPLICATIONS

This Application is a Continuation of Application U.S. patent application Ser. No. 14/733,139 filed on Jun. 8, 2015, now U.S. Pat. No. 9,670,187, which claims priority to and the benefit of U.S. Provisional Application 62/010,813, filed on Jun. 11, 2014. The entire contents of these applications are incorporated herein by reference in their entirety.

FIELD

The present disclosure relates generally to the field of organic synthetic methodology for the preparation of antiviral compounds and the synthetic intermediates prepared thereby.

BACKGROUND

Hepatitis C is recognized as a viral disease of the liver. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

SUMMARY

The compound of Formula (A) is known to exhibit antiviral properties (WO 2013/075029). Processes suitable for its production are disclosed herein.

The present disclosure provides processes for making a compound of formula (A):

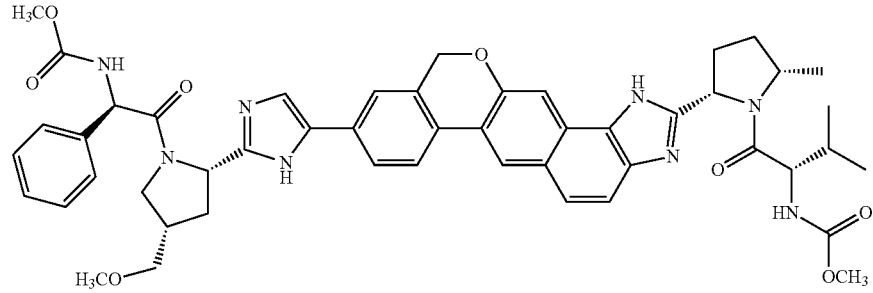

(A)

or a salt or solvate thereof.

In one embodiment, provided is a process for preparing a compound of formula (A):

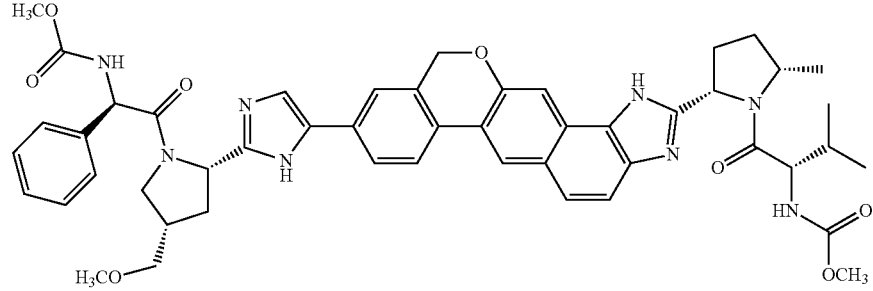

(A)

or a salt or solvate thereof, comprising the steps of:

(a) contacting a compound of formula (I), stereoisomer thereof, or mixture of stereoisomers thereof:

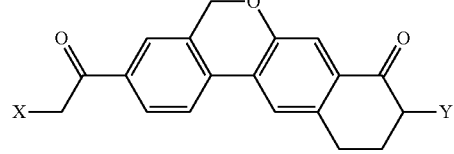
(I)

with a compound of formula (J) or salt thereof:

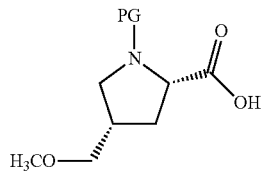
(J)

under conditions sufficient to yield a compound of formula (G), stereoisomer thereof, or mixture of stereoisomers thereof:

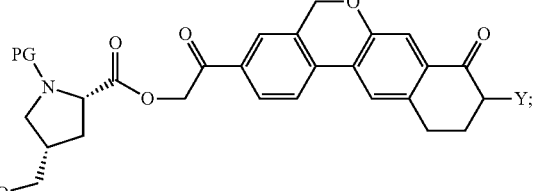
(G)

(b) contacting the compound of formula (G) with a compound of formula (H) or salt thereof:

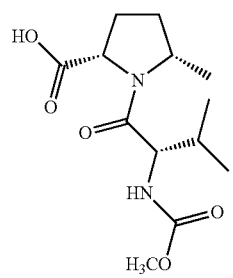
(H)

under conditions sufficient to yield a compound of formula (B), stereoisomer thereof, or mixture of stereoisomers thereof:

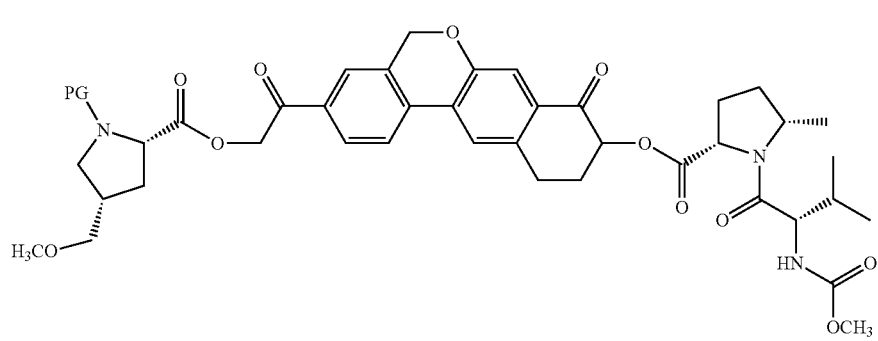
(B)

(c) cyclizing a compound of formula (B) under conditions sufficient to yield a compound of formula (C):

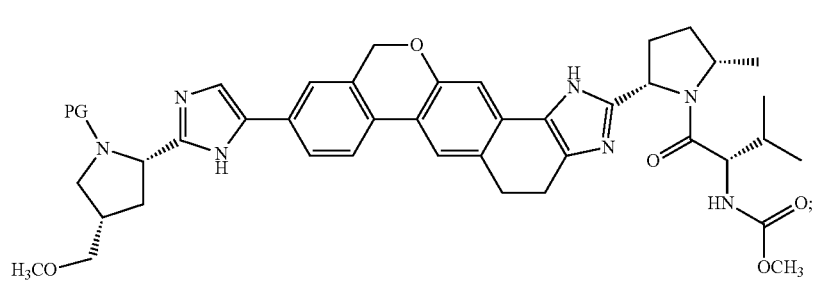
(C)

(d) dehydrogenating the compound of formula (C) under conditions sufficient to yield a compound of formula (D):

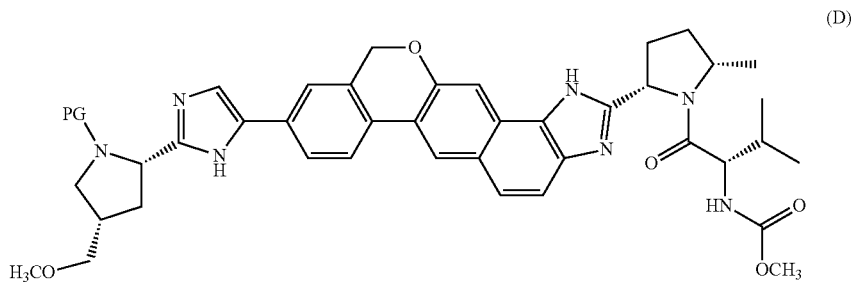

(e) deprotecting the compound of formula (D) under conditions sufficient to yield a compound of formula (E) or a salt thereof:

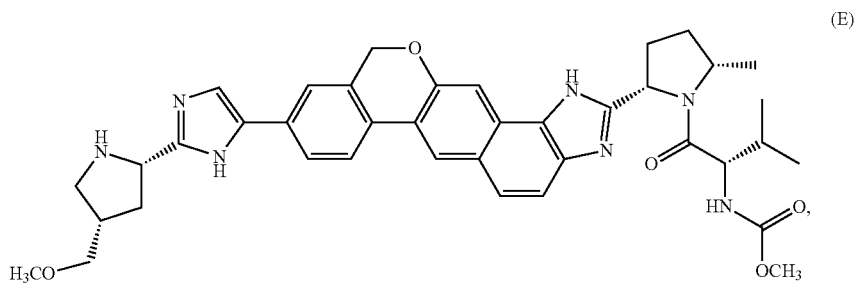 [SMILES: COC[C@@H]1CN[C@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)C1]

and (f) contacting the compound of formula (E) with a compound of formula (F):

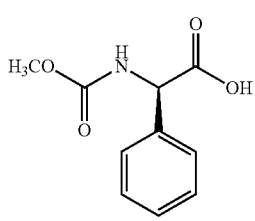

under conditions sufficient to yield a compound of formula (A), wherein PG is an amine protecting group, X and Y are each independently selected from the group consisting of halo, $-OSO_2R$, $-OP(O)OR$, and $-OP(O)(OR)_2$, and R is alkyl, haloalkyl, aryl, substituted aryl, heteroaryl, or substituted heteroaryl.

In another embodiment, provided is a process for preparing a compound of formula (A):

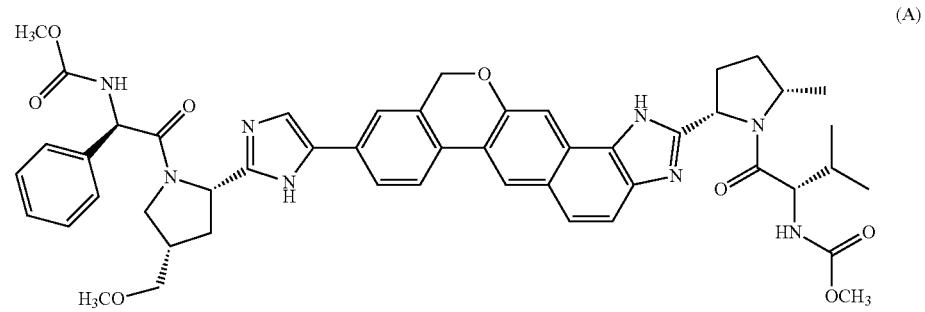 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

or a salt or solvate thereof, comprising the steps of:

(a) contacting a compound of formula (I-a), stereoisomer thereof, or mixture of stereoisomers thereof:

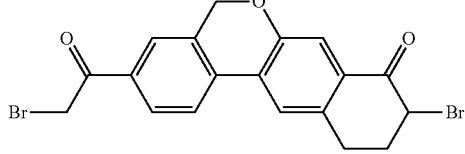
(I-a)

with a compound of formula (J) or salt thereof:

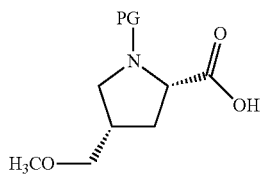
(J)

under conditions sufficient to yield a compound of formula (G'), stereoisomer thereof, or mixture of stereoisomers thereof:

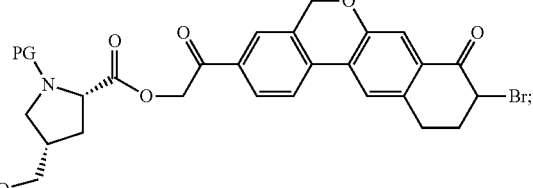
(G')

(b) contacting the compound of formula (G') with a compound of formula (H) or salt thereof:

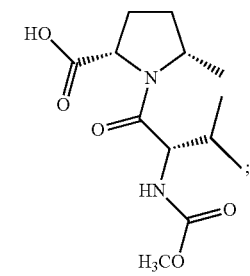
(H)

under conditions sufficient to yield a compound of formula (B), stereoisomer thereof, or mixture of stereoisomers thereof:

(B)
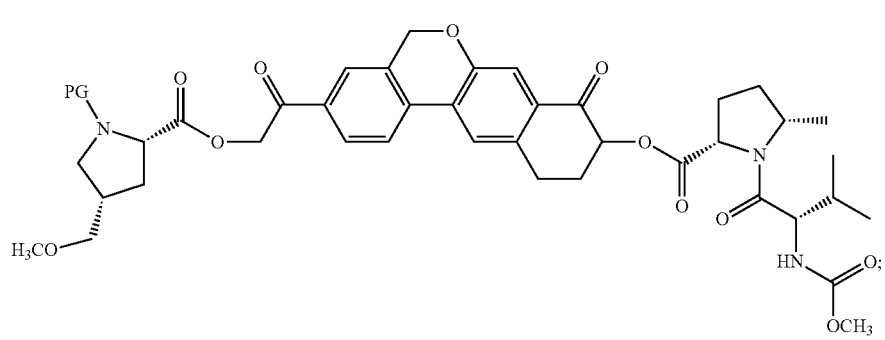

(c) cyclizing the compound of formula (B) under conditions sufficient to yield a compound of formula (C):

(C)
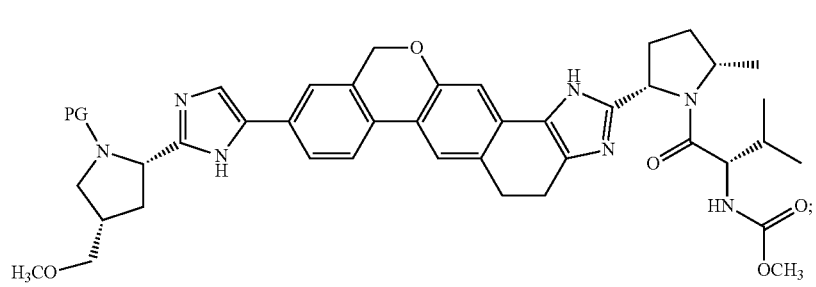

(d) dehydrogenating the compound of formula (C) under conditions sufficient to yield a compound of formula (D):

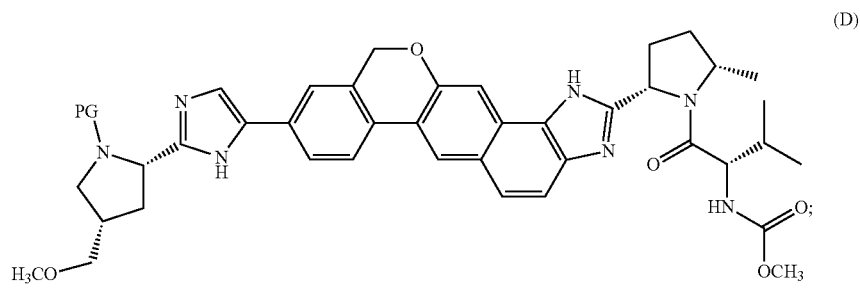

(e) deprotecting the compound of formula (D) under conditions sufficient to yield a compound of formula (E) or a salt thereof:

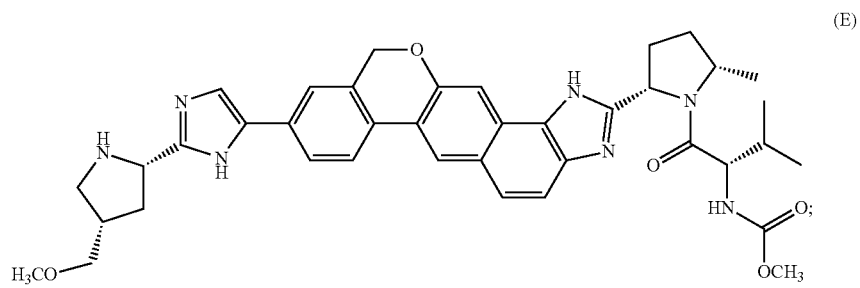 [SMILES: COC[C@@H]1CN[C@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)C1]

and (f) contacting the compound of formula (E) with a compound of formula (F):

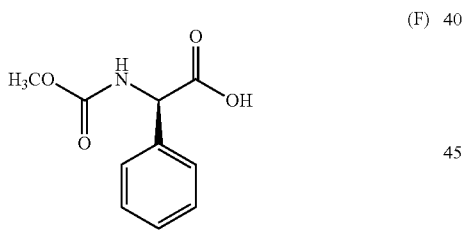

under conditions sufficient to yield a compound of formula (A), wherein PG is an amine protecting group.

Also provided herein is a process for preparing a compound of formula (D):

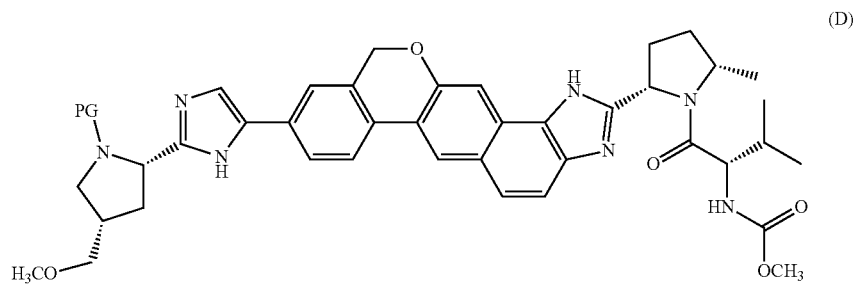

comprising (a) contacting a compound of formula (I), stereoisomer thereof, or mixture of stereoisomers thereof:

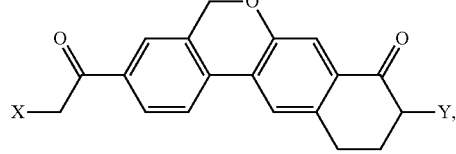

(I)

with a compound of formula (J) or salt thereof:

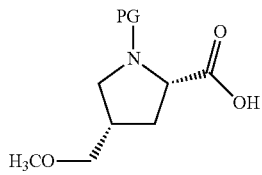

(J)

under conditions sufficient to yield a compound of formula (G), stereoisomer thereof, or mixture of stereoisomers thereof:

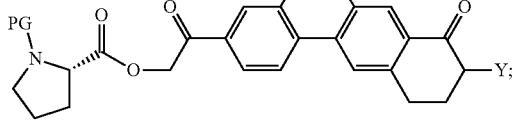

(G)

(b) contacting the compound of formula (G) with a compound of formula (H) or salt thereof:

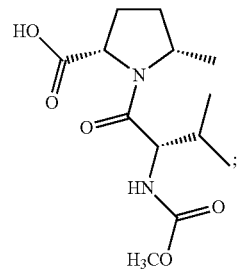

(H)

under conditions sufficient to yield a compound of formula (B), stereoisomer thereof, or mixture of stereoisomers thereof:

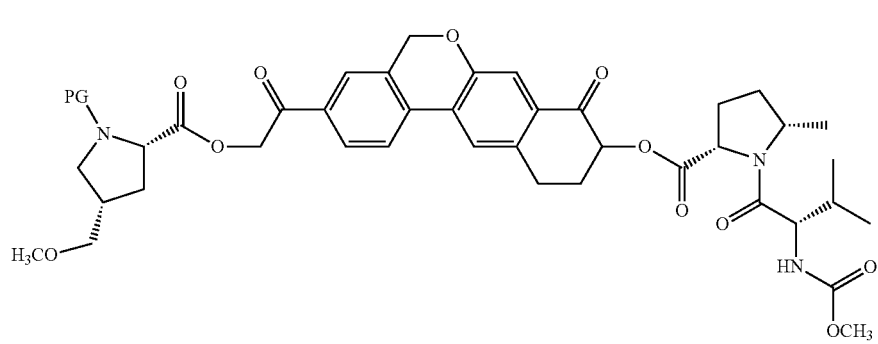

(B)

(c) cyclizing a compound of formula (B) under conditions sufficient to yield a compound of formula (C):

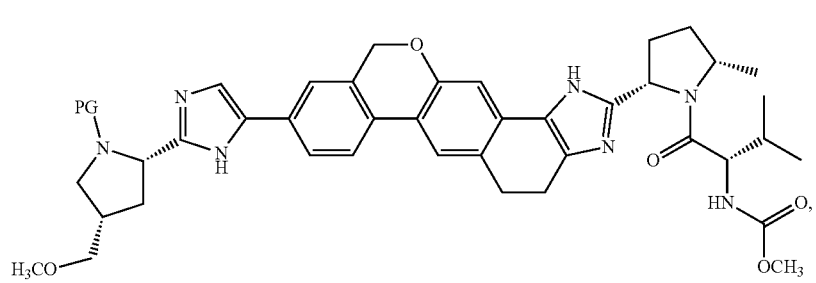

(C)

and (d) dehydrogenating a compound of formula (C) under conditions sufficient to yield a compound of formula (D), wherein PG is an amine protecting group, X and Y are each independently selected from the group consisting of halo, —OSO₂R, —OP(O)OR, and —OP(O)(OR)₂, and R is alkyl, haloalkyl, aryl, substituted aryl, heteroaryl, or substituted heteroaryl.

Also provided herein is a process for preparing a compound of formula (C):

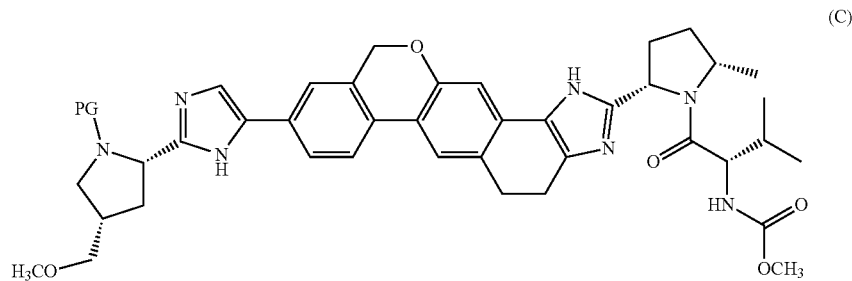

(C)

comprising (a) contacting a compound of formula (I), stereoisomer thereof, or mixture of stereoisomers thereof:

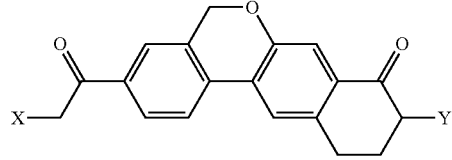

(I)

with a compound of formula (J) or salt thereof:

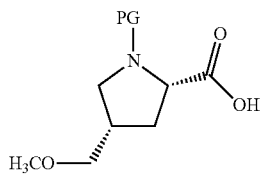

(J)

under conditions sufficient to yield a compound of formula (G), stereoisomer thereof, or mixture of stereoisomers thereof:

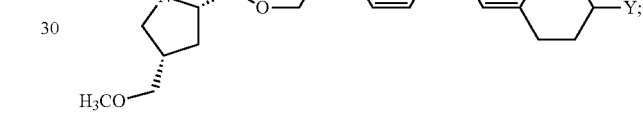

(G)

(b) contacting the compound of formula (G) with a compound of formula (H) or salt thereof:

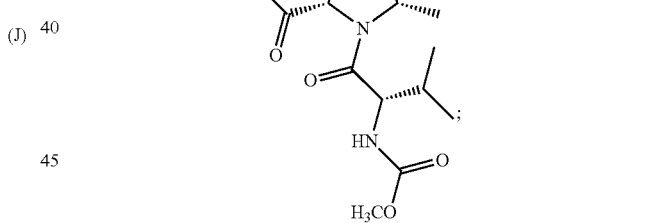

(H)

under conditions sufficient to yield a compound of formula (B), stereoisomer thereof, or mixture of stereoisomers thereof:

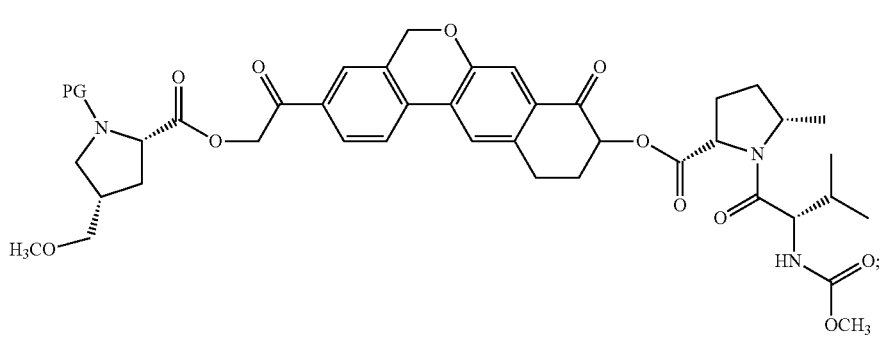

(B)

and (c) cyclizing a compound of formula (B) under conditions sufficient to yield a compound of formula (C), wherein PG is an amine protecting group, X and Y are each independently selected from the group consisting of halo, —OSO$_2$R, —OP(O)OR, and —OP(O)(OR)$_2$, and R is alkyl, haloalkyl, aryl, substituted aryl, heteroaryl, or substituted heteroaryl.

In another embodiment, provided is a process for preparing a compound of formula (I-a), stereoisomer, or mixture of stereoisomers thereof:

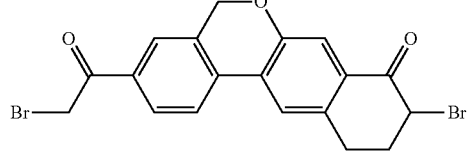

(I-a)

comprising the steps of:
(a) cyclizing a compound of formula (L):

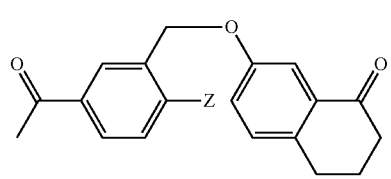

(L)

under conditions sufficient to yield a compound of formula (K):

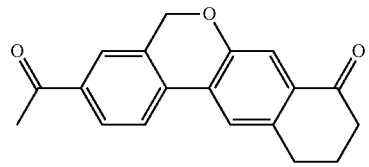

(K)

and (b) brominating the compound of formula (K) under conditions sufficient to yield a compound of formula (I-a), wherein Z is hydrogen, halo, —OSO$_2$R$^1$, —BF$_3^-$, —B(OR$^2$)$_2$, —CO$_2$H, or —NR$^1{}_3$ wherein R$^1$ is alkyl, haloalkyl, aryl, substituted aryl, heteroaryl, or substituted heteroaryl, and R$^2$ is alkyl.

Also provided are processes for preparing a compound of formula (K):

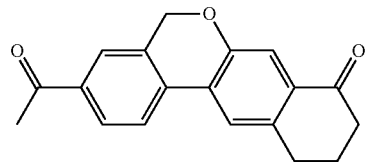

(K)

comprising reacting a compound of formula (O):

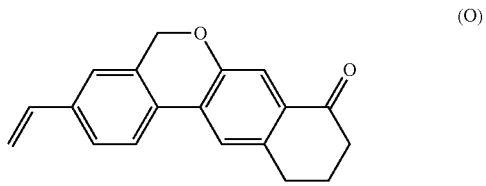 [SMILES: C=Cc1ccc2c(c1)COc1cc3c(cc1-2)CCCC3=O]

(O)

under conditions sufficient to yield a compound of formula (K).

In another embodiment, provided is a process for preparing a compound of formula (K):

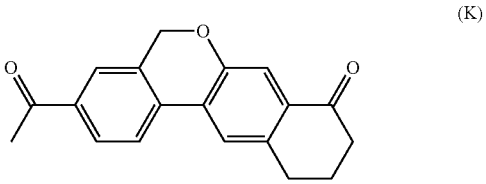 [SMILES: CC(=O)c1ccc2c(c1)COc1cc3c(cc1-2)CCCC3=O]

(K)

comprising hydrolyzing a compound of formula (P):

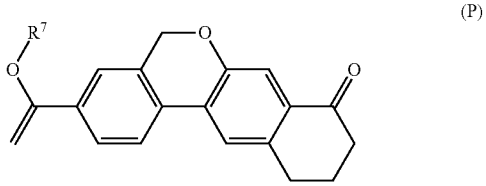

(P)

wherein R$^7$ is alkyl, under conditions sufficient to yield a compound of formula (K).

In another embodiment, provided is a process for preparing a compound of formula (K):

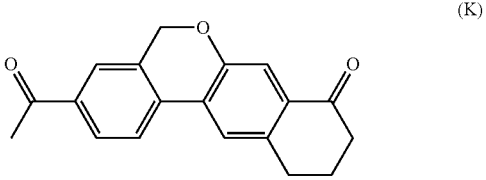 [SMILES: CC(=O)c1ccc2c(c1)COc1cc3c(cc1-2)CCCC3=O]

(K)

comprising derivatizing a compound of formula (Q):

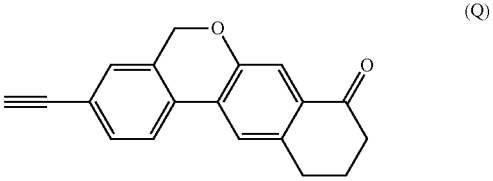 [SMILES: C#Cc1ccc2c(c1)COc1cc3c(cc1-2)CCCC3=O]

(Q)

under conditions sufficient to yield the compound of formula K.

In one embodiment, a compound of formula (R):

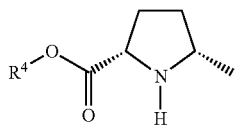
(R)

is prepared by (a) cyclizing a compound of formula (U):

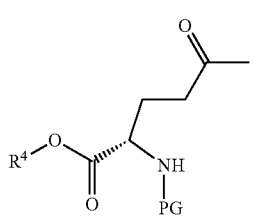
(U)

under conditions sufficient to yield the compound of formula (V):

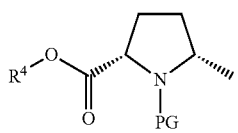
(V)

and (b) contacting the compound of formula (V) with an acid under conditions sufficient to yield the complex of formula (R), wherein PG is an amine protecting group and $R^4$ is an optionally substituted alkyl or optionally substituted aryl. In some embodiments, salts of (R) may be synthesized using certain acids such as para-toluenesulfonic acid, camphor sulfonic acid, methane sulfonic acid, benzene sulfonic acid, or p-bromobenzene sulfonic acid, among others. In particular embodiments $R^4$ is alkyl and in more particular embodiments $R^4$ is ethyl.

In one specific embodiment, provided is a process for preparing a salt of (R) wherein $R^4$ is ethyl which is a complex of formula (R-a):

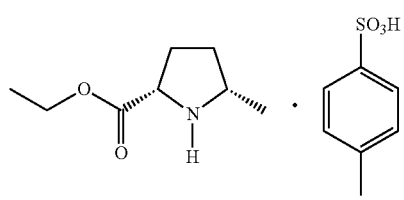
(R-a)

comprising the steps of:
(a) cyclizing a compound of formula (U'):

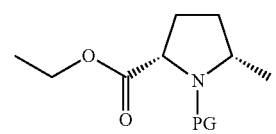
(U')

under conditions sufficient to yield the compound of formula (V'):

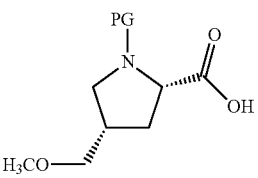
(V')

and (b) contacting the compound of formula (V') with para-toluenesulfonic acid, wherein PG is an amine protecting group, under conditions sufficient to yield the complex of formula (R-a).

Also provided herein is a process for preparing a compound of formula (J) or salt thereof:

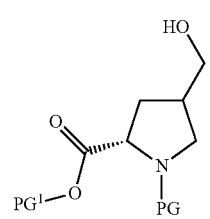
(J)

comprising the steps of:
(a) contacting a compound of formula (W):

(W)

with a hydroboration reagent under conditions sufficient to yield a compound of formula (X):

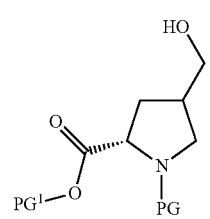
(X)

(b) methylating the compound of formula (X) under conditions sufficient to yield a compound of formula (Y):

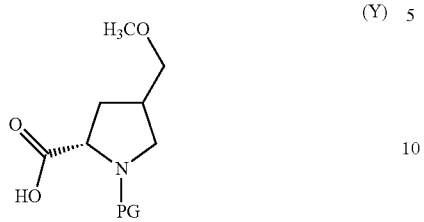

and (c) resolving the compound of formula (Y) under conditions sufficient to yield a compound of formula (J), wherein PG is an amine protecting group and $PG^1$ is a carboxylic acid protecting group.

In other embodiments, the disclosure provides intermediate compounds that are useful in the processes described herein. Thus, for instance, one embodiment is a compound of the formula L:

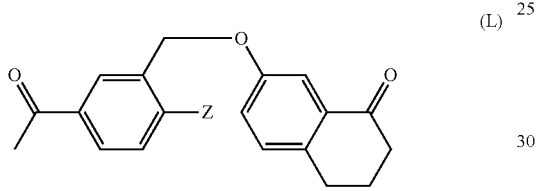

wherein Z is hydrogen, halo, —$OSO_2R^1$, —$BF_3^-$, —$B(OR^2)_2$, —$CO_2H$, or —$NR^1_3$ wherein $R^1$ is alkyl, haloalkyl, aryl, substituted aryl, heteroaryl, or substituted heteroaryl, and $R^2$ is alkyl.

Also provided herein are compounds of formula (Q):

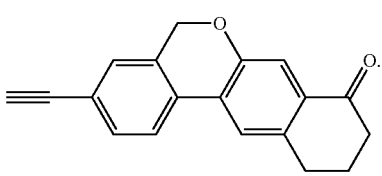

The inventions of this disclosure are described throughout. In addition, specific embodiments are as disclosed herein.

DETAILED DESCRIPTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —$S(O)_2$-alkyl, —$S(O)_2$-cycloalkyl, —$S(O)_2$-heterocyclyl, —$S(O)_2$-aryl and —$S(O)_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_n R^a$, in which $R^a$ is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and $NR^a$, where $R^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_n R^a$, in which $R^a$ is alkyl, aryl or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4 or 5 atoms) as defined above.

The term "haloalkyl" refers to an alkyl group substituted with one or more halogen groups. For example, "$C_{1-3}$ haloalkyl" refers to an alkyl group having from 1 to 3 carbon atoms covalently bonded to from 1 to 7, or from 1 to 6, or from 1 to 3, halogen(s), where alkyl and halogen are defined herein. In some embodiments, $C_{1-3}$ haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, 3-fluoropropyl.

The term "lower alkyl" refers to a monoradical branched or unbranched saturated hydrocarbon chain having 1, 2, 3, 4, 5 or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (in some embodiments, 1, 2 or 3 substituents), as defined for substituted alkyl or a lower alkyl group as defined above that is interrupted by 1, 2, 3, 4 or 5 atoms as defined for substituted alkyl or a lower alkyl group as defined above that has both 1, 2, 3, 4 or 5 substituents as defined above and is also interrupted by 1, 2, 3, 4 or 5 atoms as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "lower alkylene" refers to a diradical of a branched or unbranched saturated hydrocarbon chain, in some embodiments, having 1, 2, 3, 4, 5 or 6 carbon atoms.

The term "substituted alkylene" refers to an alkylene group as defined above having 1 to 5 substituents (in some embodiments, 1, 2 or 3 substituents) as defined for substituted alkyl.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH=CH$_2$), 1-propylene (or allyl, i.e. —CH$_2$CH=CH$_2$), isopropylene (—C(CH$_3$)=CH$_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is substituted alkylene and Z is substituted alkenyl or substituted alkynyl, where substituted alkyl, substituted alkenyl and substituted alkynyl are as defined herein.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in some embodiments, 1, 2 or 3 substituents) as defined for substituted alkyl.

The term "alkynylene" refers to a diradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. The term "substituted cycloalkyl" also includes cycloalkyl groups wherein one or more of the annular carbon atoms of the cycloalkyl group has an oxo group bonded thereto. In addition, a substituent on the cycloalkyl or cycloalkenyl may be attached to the same carbon atom as, or is geminal to, the attachment of the substituted cycloalkyl or cycloalkenyl to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring. In some embodiments, the heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. In addition, a substituent on the heterocyclic group may be attached to the same carbon atom as, or is geminal to, the attachment of the substituted heterocyclic group to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine.

The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "benzyl" refers to the group —$CH_2$—$C_6H_5$

The term "amino" refers to the group —$NH_2$.

The term "amine" refers to substituted amino, alkyl amine, dialkylamine, or trialkyl amine groups.

The term "substituted amino" refers to the group —NRR where each R is independently selected from the group consisting of hydrogen, alkyl, cycloalkyl, aryl, heteroaryl and heterocyclyl provided that both R groups are not hydrogen or a group -Y-Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkyl amine" refers to R—$NH_2$ in which R is optionally substituted alkyl.

The term "dialkyl amine" refers to R—NHR in which each R is independently an optionally substituted alkyl.

The term "trialkyl amine" refers to $NR_3$ in which each R is independently an optionally substituted alkyl.

The term "cyano" refers to the group —CN.

The term "azido" refers to a group

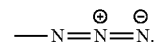

The term "nitro" refers to a group —$NO_2$.

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, $CF_3$, amino, substituted amino, cyano or —S(O)$_n$R$^a$, in which R$^a$ is alkyl, aryl or heteroaryl and n is 0, 1 or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acyl halide" denotes the group —C(O)RX, in which R is hydrogen, alkyl, cycloalkyl, heterocyclyl, aryl or heteroaryl. X is a halide group. The term "halide" halide ion refers to a halogen atom bearing a negative charge. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkoxycarbonylamino" refers to the group —N(R$^d$)C(O)OR in which R is alkyl and R$^d$ is hydrogen or alkyl. Unless otherwise constrained by the definition, each alkyl may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aminocarbonylamino" refers to the group —NR$^c$C(O)NRR, wherein R$^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthio" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "aminosulfonyl" refers to the group —S(O)$_2$NRR, wherein each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "hydroxy" or "hydroxyl" refers to the group —OH.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

The term "hydroboration reagent" refers to a reagent that contains boron and can be used during a hydroboration reaction. Non-limiting examples can be $BH_3$-THF, 9-borabicyclo[3.3.1]nonane ("9-BBN"), catecholborane, and disiamylborane.

The term "reagent" refers to a substance or compound that can be added to bring about a chemical reaction.

The term "oxidant" refers to a compound that has a carbon that can gain electron density from another compound in a chemical reaction.

The term "amine reagent" refers to a compound that has nitrogen.

The term "additive" can refer to a compound that can be added to a chemical reaction.

The term "coupling reagent" or "coupling agent" refers to a compound that aids in bringing about a reaction to couple one compound to another compound.

The term "organic base" is an organic compound that acts as a base.

The term "organic acid" is an organic compound that acts as an acid.

The term "brominating reagent" or "brominating agent" refers to a compound that can be added to carry out a bromination reaction.

The term "borohydride reagent" refers to a borohydride compound, such as sodium triacetoxyborohydride, sodium borohydrodride, or sodium tripropionoxyborohydride.

The term "complex" refers to a formation resulting from the interaction between a molecule and a second molecule.

A "leaving group" includes a molecular fragment that can depart with a pair of electrons from a covalent bond to the reacting carbon atom during a chemical reaction.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of a given formula is intended to encompass the compounds of the disclosure, and the pharmaceutically acceptable salts, pharmaceutically acceptable esters, isomers, tautomers, solvates, isotopes, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as "tautomeric isomers" or "tautomers." Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers. Non-limiting examples of amide-comprising and imidic acid-comprising tautomers are shown below:

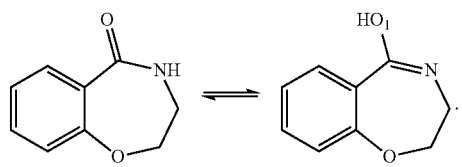

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound and a solvent.

The term "hydrate" refers to the complex formed by the combining of a compound and water.

The term "prodrug" refers to compounds that include chemical groups which, in vivo, can be converted and/or can be split off from the remainder of the molecule to provide for the active drug, a pharmaceutically acceptable salt thereof or a biologically active metabolite thereof.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds in which from 1 to n hydrogens attached to a carbon atom is/are replaced by deuterium, in which n is the number of hydrogens in the molecule. Such compounds exhibit increased resistance to metabolism and are thus useful for increasing the half life of any compound of Formula I when administered to a mammal. See, for example, Foster, "Deuterium Isotope Effects in Studies of Drug Metabolism", Trends Pharmacol. Sci. 5(12): 524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base "salts" by virtue of the presence of amino and/or carboxyl groups or groups similar thereto. In some cases, the "salt" of a given compound is a pharmaceutically acceptable salt. The term "pharmaceutically acceptable salt" of a given compound refers to salts that retain the biological effectiveness and properties of the given compound, and which are not biologically or otherwise undesirable.

Base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein monosubstituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroaryl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to $NH(heteroaryl)_2$, wherein "heteroaryl" is as defined herein and so on. Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. Acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "reaction conditions" is intended to refer to the physical and/or environmental conditions under which a chemical reaction proceeds. Examples of reaction conditions include, but are not limited to, one or more of following: reaction temperature, solvent, pH, pressure, reaction time, mole ratio of reactants, the presence of a base or acid, or catalyst, radiation, etc. Reaction conditions may be named after the particular chemical reaction in which the conditions are employed, such as, coupling conditions, hydrogenation conditions, acylation conditions, reduction conditions, etc. Reaction conditions for most reactions are generally known to those skilled in the art or can be readily obtained from the literature. Exemplary reaction conditions sufficient for performing the chemical transformations provided herein can be found throughout, and in particular, the examples below. It is also contemplated that the reaction conditions can include reagents in addition to those listed in the specific reaction.

The term "reducing agent" refers to the addition of hydrogen to a molecule. Exemplary reducing agents include hydrogen gas ($H_2$) and hydride reagents such as borohydrides, lithium aluminium hydride, diisobutylaluminium hydride (DIBAL-H) and lithium triethylborohydride.

The term "protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion.

The term "deprotecting" refers to removing the protecting group.

The term "amine protecting group" refers to a chemical moiety which is added to, and later removed from, an amine functionality to obtain chemoselectivity in a subsequent chemical reaction. Suitable nitrogen protecting groups include carbobenzyloxy (Cbz) (removed by hydrogenolysis), p-methoxybenzyl carbonyl (Moz or MeOZ) (removed by hydrogenolysis), tert-butyloxycarbonyl (Boc) (removed by concentrated strong acids, such as HCl or trifluoroacetic acid, or by heating), 9-fluorenylmethyloxycarbonyl (FMOC) (removed by base, such as piperidine), acetyl (Ac) (removed by treatment with a base), benzoyl (Bz) (removed by treatment with a base, most often with aqueous or gaseous ammonia or methylamine), benzyl (Bn) (removed by hydrogenolysis), a carbamate (removed by acid and mild heating), p-methoxybenzyl (PMB) (removed by hydrogenolysis), 3,4-dimethoxybenzyl (DMPM) (removed by hydrogenolysis), p-methoxyphenyl (PMP) (removed by ammonium cerium(IV) nitrate), a succinimide (i.e., a cyclic imide) (removed by treatment with a base), tosyl (Ts) (removed by concentrated acid and strong reducing agents), and other sulfonamides (Nosyl and Nps) (removed by samarium iodide, tributyltin hydride, etc.).

The term "carboxylic acid protecting group" refers to a chemical moiety which is added to, and later removed from, a carboxylic acid functionality to obtain chemoselectivity in a subsequent chemical reaction. Suitable carboxylic acid protecting groups include methyl esters (removed by acid or base), benzyl esters (removed by hydrogenolysis), tert-butyl esters (removed by acid, base, and some reductants), silyl esters (removed by acid, base, and organicmetallic reagents), orthoesters (removed by mild aqueous acid to form esters, which can be removed according to the ester's properties), and oxazoline (removed at pH<1 or pH>12 with heat).

The term "succinimide" refers to a cyclic imide, and may be monocyclic, bicyclic (e.g., phthalimides) or polycyclic, and may further be optionally substituted. Non limiting examples include N-pthalimide, N-dichlorophthalimide, N-tetrachlorophthalimide, N-4-nitrophthalimide, N-dithiasuccinimide, N-2,3-diphenylmaleimide, and N-2,3-dimethylmaleimide.

The term "catalyst" refers to a chemical substance that enables a chemical reaction to proceed at a usually faster rate or under different conditions (such as at a lower temperature) than otherwise possible.

In addition, abbreviations as used herein have respective meanings as follows:

| | |
|---|---|
| 2-MeTHF | 2-methyltetrahydrofuran |
| 9-BBN | 9-borabicyclo[3.3.1]nonane |
| Ac | Acetate |
| aq | Aqueous |
| Boc | tert-Butoxycarbonyl |
| BOP | (Benzotriazol-1-yloxy)tris(dimethylamino)phosphonium hexafluorophosphate |
| brs | Broad singlet |
| Bu | Butyl |
| CDI | Carbonyldiimidazole |
| CDMT | 2-chloro-4,6-bis[3-(perfluorohexyl)propyloxy]-1,3,5-triazine |
| comp | Complicated |
| conc. | Concentrated |
| COMU | (1-Cyano-2-ethoxy-2-oxoethylidenaminooxy)dimethylamino-morpholino-carbenium hexafluorophosphate |
| d | Doublet |
| Dba | dibenzylideneacetone |
| DBU | 1,8-Diazabicyclo[5.4.0]undec-7-ene |
| DCM | Dichloromethane |
| DCC | N,N'-Dicyclohexylcarbodiimide |
| dd | Doublet of doublets |
| DMAc | Dimethylacetamide |
| DMAP | 4-Dimethylaminopyridine |
| DMF | Dimethylformamide |
| DMSO | Dimethylsulfoxide |
| EDC/EDCI | 1-Ethyl-3-(3-dimethylaminopropyl)carbodiimide |
| Equiv | Equivalents |
| Et | Ethyl |
| EtOAc | Ethyl acetate |
| EtOH | Ethanol |
| g | Gram |
| h | Hour |
| HATU | 1-[Bis(dimethylamino)methylene]-1H-1,2,3-triazolo[4,5-b]pyridinium 3-oxid hexafluorophosphate |
| HBTU | N,N,N',N'-Tetramethyl-O-(1H-benzotriazol-1-yl)uronium hexafluorophosphate |
| HOBt | Hydroxybenzotriazole |
| HPLC | High-pressure liquid chromatography |
| Hz | Hertz |
| iPr | Isopropyl |
| J | Coupling constant |
| LCMS | Liquid chromatography-mass spectrometry |
| m | Multiplet |
| M | Molar |
| m/z | Mass to charge |
| Me | Methyl |
| MeOH | Methanol |
| MEK | Methyl ethyl ketone |
| mg | Milligram |
| MHz | Mega hertz |
| MIBK | Methyl isobutyl ketone |
| mL | Milliliter |
| mmol | Millimole |
| MTBE | Methyl-tert-butyl ether |
| NMM | N-Methylmorpholine |
| NMP | N-Methyl-2-pyrrolidone |
| NMR | Nuclear magnetic resonance |
| Oxyma | Ethyl 2-Cyano-2-(hydroxyimino)acetate |
| Ph | Phenyl |
| Pr | Propyl |
| PSI/psi | Pound-force per square inch |
| Py | Pyridine |
| PyBOP | benzotriazol-1-yl-oxytripyrrolidinophosphonium hexafluorophosphate |
| PyClOP | Chlorotripyrrolidinophosphonium hexafluorophosphate |
| s | Singlet |
| t | Triplet |
| T3P | Propylphosphonic Anhydride |

-continued

| | |
|---|---|
| TBDMS | Tert-butyldimethylsilyl |
| TBS | Tert-butyldimethylsilyl |
| TBTU | O-(Benzotriazol-1-yl)-N,N,N',N'-tetramethyluronium tetrafluoroborate |
| t-Bu | tert-Butyl |
| TEMPO | (2,2,6,6-Tetramethylpiperidin-1-yl)oxy |
| TFA | Trifluoroacetic acid |
| THF | Tetrahydrofuran |
| TLC | Thin layer chromatography |
| Ts | Tosyl |
| vol | Volume |
| wt | Weight |
| Δ | Chemical shift |
| μL | Microliter |

Processes

As described generally above, the disclosure provides in some embodiments processes for making a compound of formula (A).

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemie or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller, C. H., (1975) *J. Chromatogr.*, 113, 3) 283-302). Racemic mixtures of chiral compounds of the disclosure can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched substrate. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (Chiral Liquid Chromatography (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Scheme 1 represents an exemplary synthesis of compound of formula (A) and can be carried out according to the embodiments described herein.

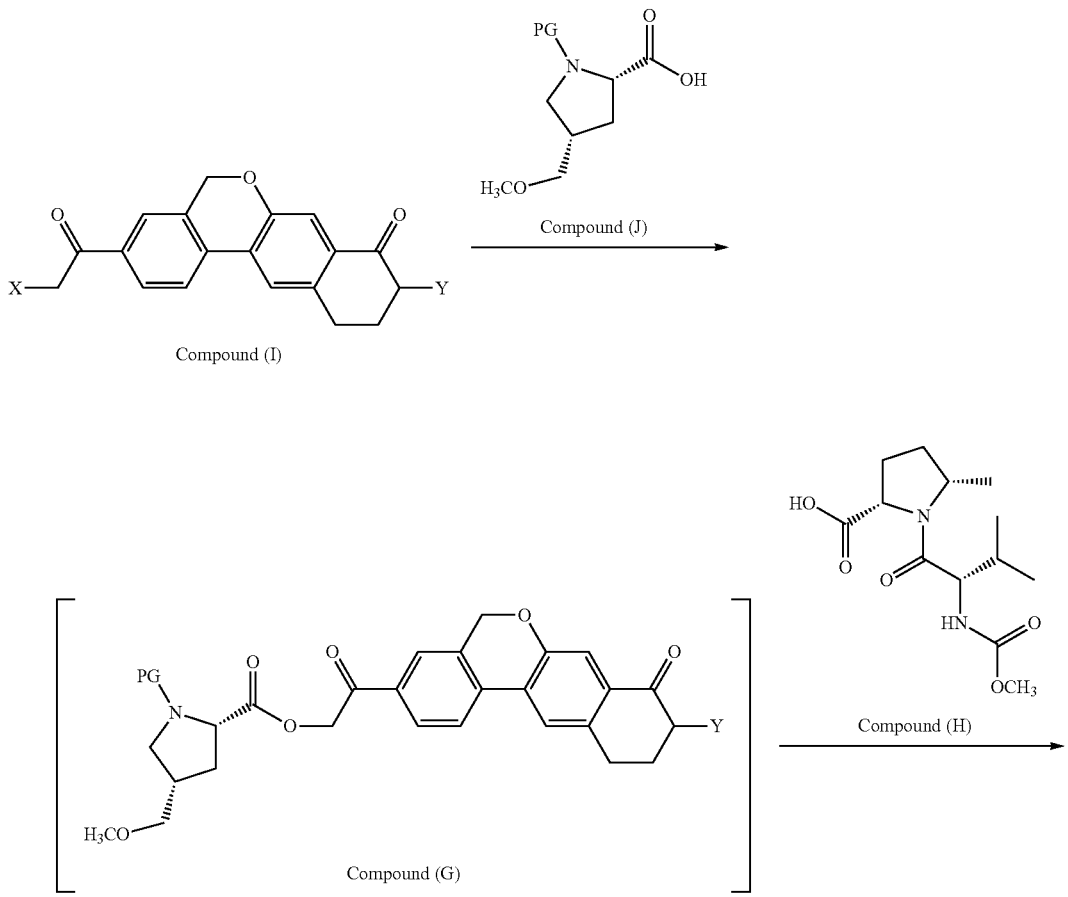

-continued
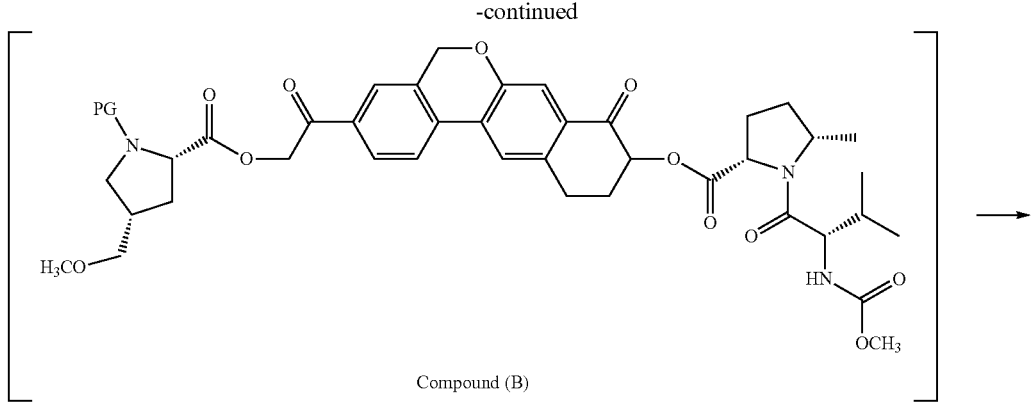
Compound (B)
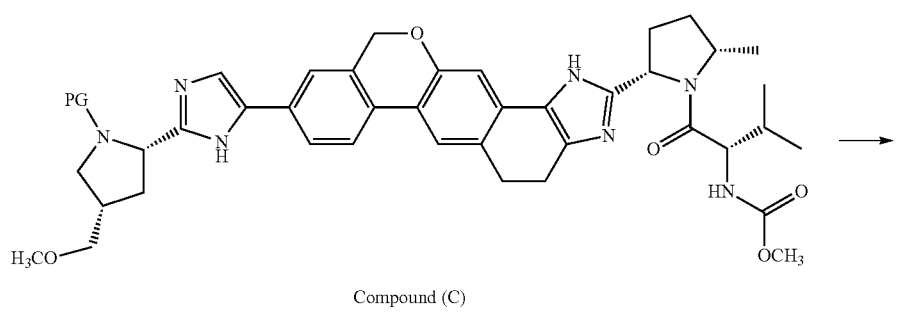
Compound (C)
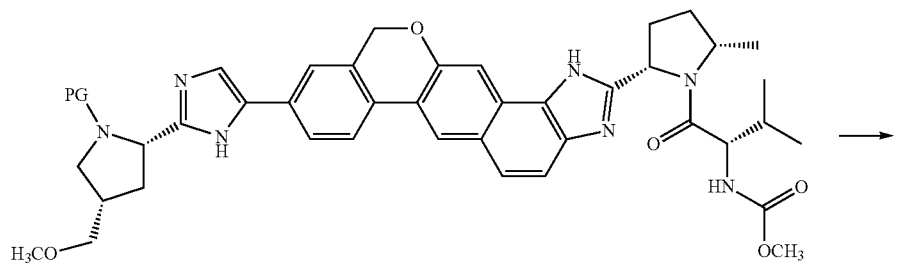
Compound (D)
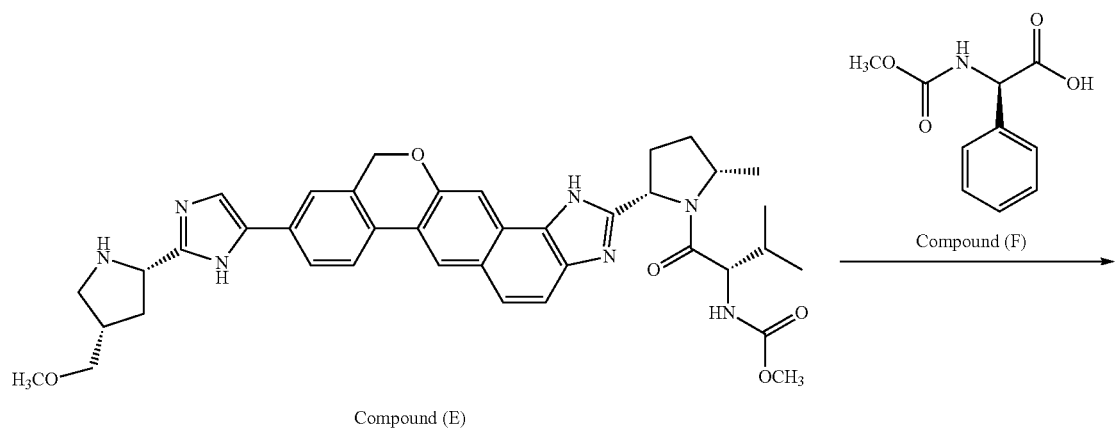
Compound (E)   Compound (F)

-continued

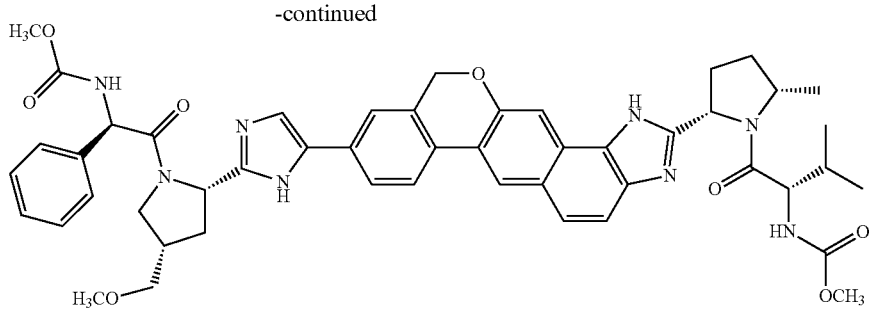

Compound (A)

In some embodiments, X and Y may be various moieties as discussed below. The particular reaction conditions and reagents employed in Scheme 1 are discussed below.

In one embodiment, the present disclosure provides for a process for preparing a compound of formula (A):

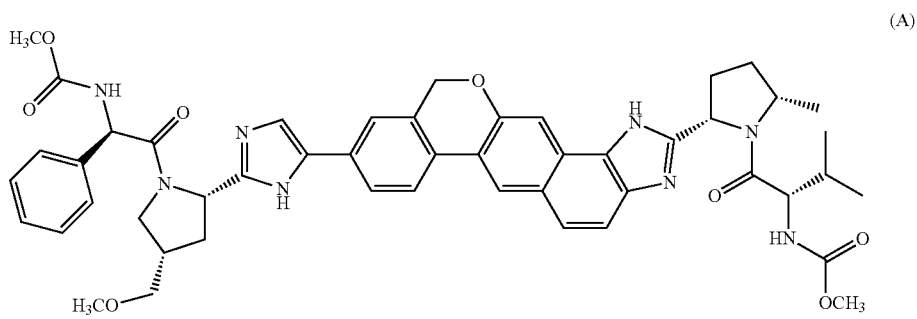 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

(A)

or a salt or solvate thereof, comprising the steps of:

(a) contacting a compound of formula (I), stereoisomer thereof, or mixture of stereoisomers thereof:

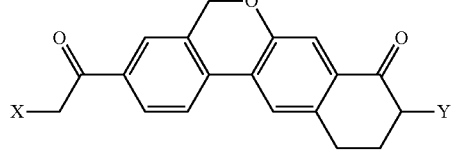

(I)

with a compound of formula (J) or salt thereof:

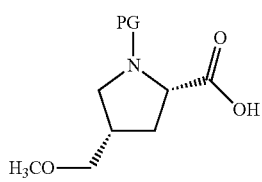

(J)

under conditions sufficient to yield a compound of formula (G), stereoisomer thereof, or mixture of stereoisomers thereof:

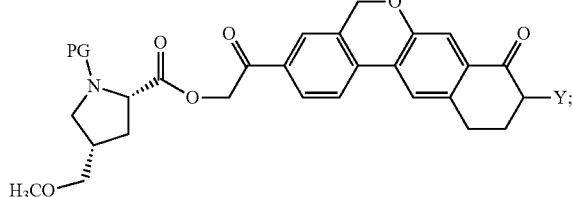

(G)

(b) contacting the compound of formula (G) with a compound of formula (H) or salt thereof:

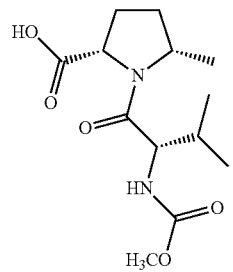

(H)

under conditions sufficient to yield a compound of formula (B), stereoisomer thereof, or mixture of stereoisomers thereof:

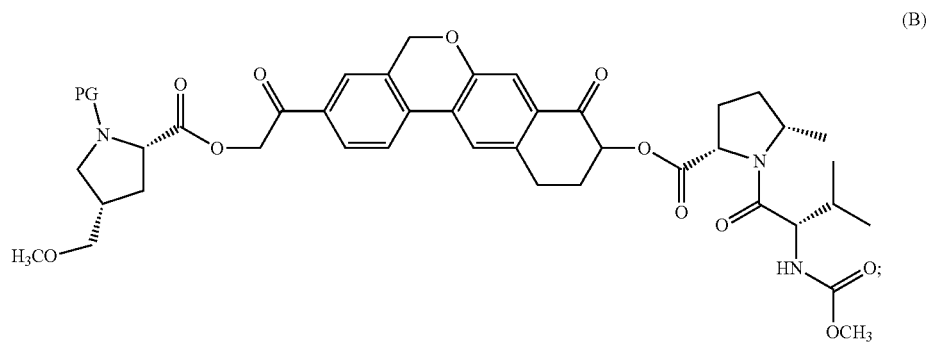
(B)

(c) cyclizing a compound of formula (B) under conditions sufficient to yield a compound of formula (C):

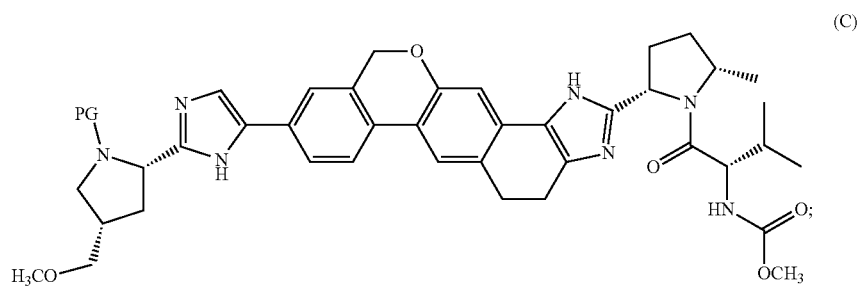
(C)

(d) dehydrogenating the compound of formula (C) under conditions sufficient to yield a compound of formula (D):

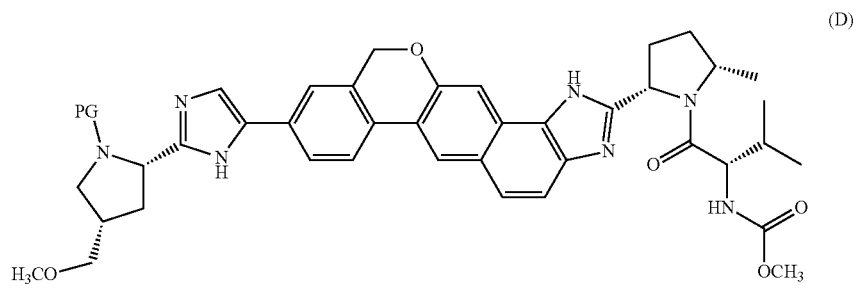
(D)

(e) deprotecting the compound of formula (D) under conditions sufficient to yield a compound of formula (E) or a salt thereof:

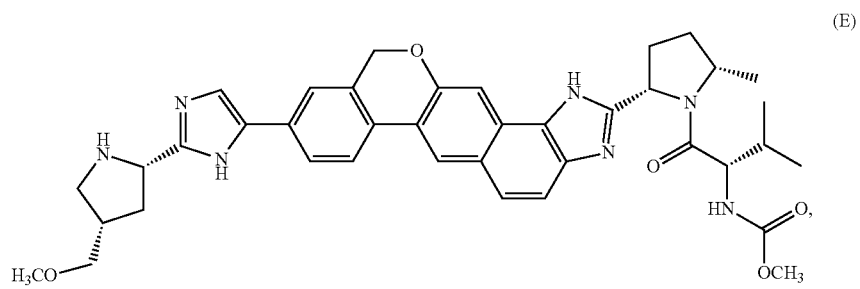 [SMILES: COC[C@@H]1CN[C@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)C1]
(E)

and (f) contacting the compound of formula (E) with a compound of formula (F):

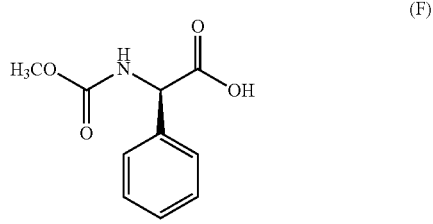 [SMILES: COC(=O)N[C@@H](C(=O)O)c1ccccc1]

(F)

under conditions sufficient to yield a compound of formula (A), wherein PG is an amine protecting group, X and Y are each independently selected from the group consisting of halo, —OSO$_2$R, —OP(O)OR, and —OP(O)(OR)$_2$, wherein R is alkyl, haloalkyl, aryl, substituted aryl, heteroaryl, or substituted heteroaryl.

In some embodiments, the substituted aryl may be an aryl having one or more substituents, such as alkyl, alkoxy, hydroxyl, nitro, halogen, and others as discussed above.

In an embodiment, X is bromo and Y is bromo.

In certain embodiments, the reaction conditions of step (a) comprise a solvent selected from the group consisting of dichloromethane, 2-methyltetrahydrofuran, tetrahydrofuran, isopropyl acetate, ethyl acetate, tert-butyl methyl ether, cyclopentyl methyl ether, dimethylformamide, acetone, methyl ethyl ketone ("MEK"), and methyl isobutyl ketone ("MIBK"). In some embodiments, the reaction conditions of step (a) comprise a temperature of from about 10° C. to about 60° C. or from about 10° C. to about 30° C.

In some embodiments, the reaction conditions of step (a) comprise a phosphate salt or a carbonate salt. In certain embodiments, the phosphate salt includes but is not limited to KH$_2$PO$_4$, K$_3$PO$_4$, Na$_2$HPO$_4$, and Na$_3$PO$_4$. In some embodiments, the carbonate salt includes but is not limited to Na$_2$CO$_3$, Cs$_2$CO$_3$, and NaHCO$_3$.

In certain embodiments, the compound of formula (J) is a potassium, sodium, or cesium salt.

In certain embodiments, the reaction conditions of step (b) comprise a solvent selected from the group consisting of tetrahydrofuran, 2-methyltetrahydrofuran, dichloromethane, toluene, isopropyl acetate, ethyl acetate, 1-methyl-2-pyrrolidinone, N,N-dimethylacetamide, acetone, MEK, MIBK, and a mixture thereof. In certain embodiments, the reaction conditions of step (b) comprise a temperature of from about 40° C. to about 60° C. or from about 40° C. to about 50° C.

In some embodiments, the reaction conditions of step (b) comprise a phosphate salt or a carbonate salt. In certain embodiments, the phosphate salt includes but is not limited to KH$_2$PO$_4$, K$_3$PO$_4$, Na$_2$HPO$_4$, and Na$_3$PO$_4$. In some embodiments, the carbonate salt includes but is not limited to Na$_2$CO$_3$, Cs$_2$CO$_3$, Li$_2$CO$_3$, CsHCO$_3$, K$_2$CO$_3$, KHCO$_3$ and NaHCO$_3$. In certain embodiments, one or more phase transfer reagents may be used to assist with the reaction.

In certain embodiments, the compound of formula (H) is a potassium, a sodium, or a cesium salt.

In some embodiments, the reaction conditions of step (c) comprises an amine reagent, wherein the amine reagent comprises ammonium acetate, hexamethyldisilzane, ammonia, ammonium formate, ammonium propionate, ammonium hexanoate, or ammonium octanoate.

In certain embodiments, the reaction conditions of step (c) comprise a solvent selected from the group consisting of toluene, xylene, an alcohol, and a mixture thereof. In certain embodiments, the reaction conditions of step (c) comprise a temperature of from about 60° C. to about 110° C. or from about 85° C. to about 95° C. In some embodiments, the alcohol can be isopropanol, 1-propanol, 1-butanol, 2-butanol, 2-methoxyethanol, or a glycol, such as ethylene glycol or propylene glycol. In some embodiments, the reaction condition comprises a mixture of toluene and 2-butanol or isopropanol. In some embodiments, water is removed during the process.

In certain embodiments, the reaction conditions of step (d) comprise an oxidant. In some embodiments, the oxidant is 2,3-dichloro-5,6-dicyano-1,4-benzoquinone.

In certain embodiments, the reaction conditions of step (d) comprise an additive selected from the group consisting of carbonate base (such as potassium carbonate, potassium bicarbonate, sodium carbonate, or sodium bicarbonate), amine (such as triethylamine or diisopropylethylamine), acid (organic acids and inorganic acids), and acetate salts (such as sodium acetate or potassium acetate). In some embodiments, the additive is acetic acid.

In certain embodiments, the reaction conditions of step (d) comprise 2-methyltetrahydrofuran, or a mixture of toluene and tetrahydrofuran. In certain embodiments, the reaction conditions of step (d) comprise a temperature of from about −15° C. to about 80° C. or from about −15° C. to about 10° C. In some embodiments, the temperature is about 0° C.

In certain embodiments, the reaction conditions of step (e) comprise a deprotection reagent, wherein the deprotection reagent may be hydrochloric acid (including wherein hydrochloric acid is generated from acetyl chloride), phosphoric acid, trifluoroacetic acid, p-toluenesulfonic acid, methanesulfonic acid, ethanesulfonic acid, benzenesulfonic acid, p-toluenesulfonic acid, 4-bromobenzenesulfonic acid, thionyl chloride, and trimethylsilyl chloride. A wide range of solvents may be employed, including but not limited to water, methanol, ethanol, acetonitrile, acetone, tetrahydrofuran, 1,4-dioxane, and toluene. Deprotection may proceed at temperatures ranging from about 20° C. to about 110° C. or from about 55° C. to about 65° C.

In certain embodiments, step (e) further comprises neutralizing the compound of formula (E). In some embodiments, neutralizing the compound of formula (E) may be in a variety of organic solvents and aqueous solvents and may be performed at a temperature of from about −20° C. to about 60° C. or from about 5° C. to about 15° C. The neutralization reagent may be a wide variety of bases. In certain embodiments, the base may be sodium methoxide. In some embodiments, the neutralization solvent may be methanol.

In certain embodiments, step (e) further comprises crystallizing the compound of formula (E). In some embodiments, recrystallization of compound formula (E) comprises water, an alcohol (such as 1-propanol, 2-propanol, methanol, or ethanol), or acetonitrile. In some embodiments, the temperature may range from about −20° C. to about 100° C. The temperature may be from about 60° C. and may be ramped to cool to about 20° C. In some embodiments, recrystallization of compound of formula (E) comprises a crystallization reagent. The crystallization reagent may be an acid, such as hydrochloric acid, hydrobromic acid, sulfuric acid, ethanesulfonic acid, benzenesulfonic acid, 4-bromobenzenesulfonic acid, oxalic acid, glucuronic acid, or phosphoric acid. In some embodiments, the crystallization reagent is phosphoric acid.

In certain embodiments, the reaction conditions of step (f) comprise a solvent selected from the group consisting of dichloromethane, methanol, N,N-dimethylformamide, and a mixture thereof. In certain embodiments, the reaction conditions of step (f) comprise a temperature of from about −20° C. to about 30° C. or from about 10° C. to about 20° C.

In some embodiments, the reaction conditions of step (f) comprises a coupling agent and an organic base. The coupling agent may be those typically known in the art. In some embodiments, the coupling agent is 4-(4,6-dimethoxy-1,3,5-triazin-2-yl)-4-methylmorpholinium chloride. In some embodiments, the organic base may be an amine. In certain embodiments, the organic base is N-methylmorpholine.

In another embodiment, provided is a process for preparing compound of formula (A):

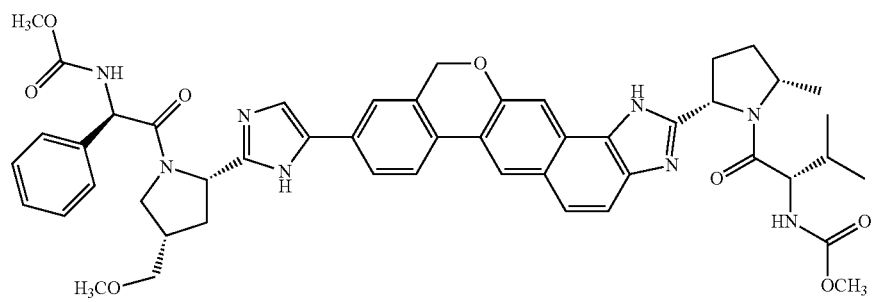

(A)

or a salt or solvate thereof, comprising the steps of:
(a) contacting a compound of formula (I-a), stereoisomer thereof, or mixture of stereoisomers thereof:

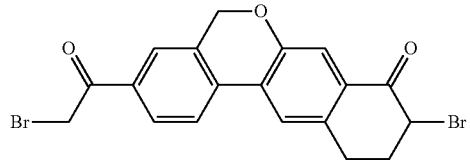

(I-a)

with a compound of formula (J) or salt thereof:

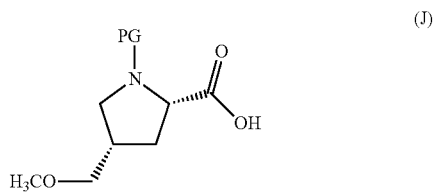

(J)

under conditions sufficient to yield a compound of formula (G'), stereoisomer thereof, or mixture of stereoisomers thereof:

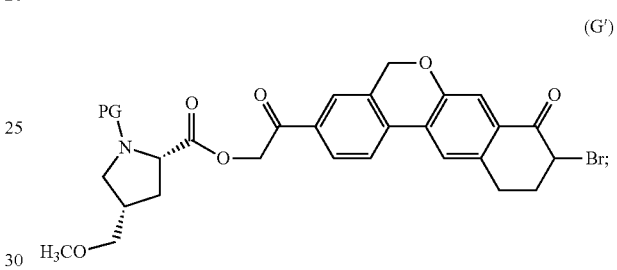

(G')

(b) contacting the compound of formula (G') with a compound of formula (H) or salt thereof:

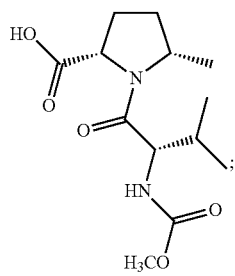

(H)

under conditions sufficient to yield a compound of formula (B), stereoisomer thereof, or mixture of stereoisomers thereof:

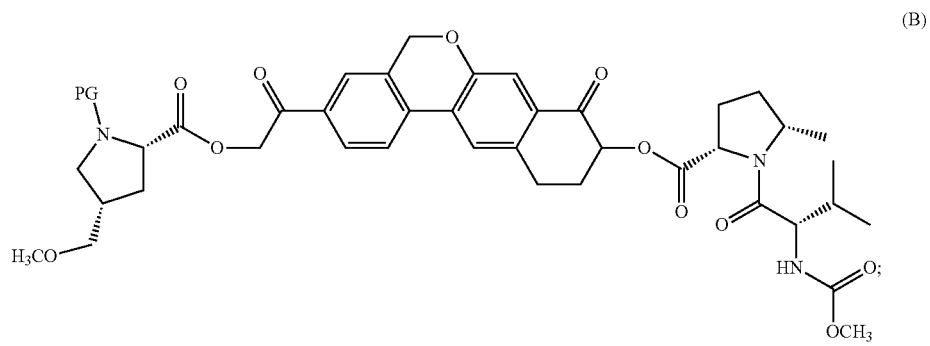

(B)

(c) cyclizing the compound of formula (B) under conditions sufficient to yield a compound of formula (C):

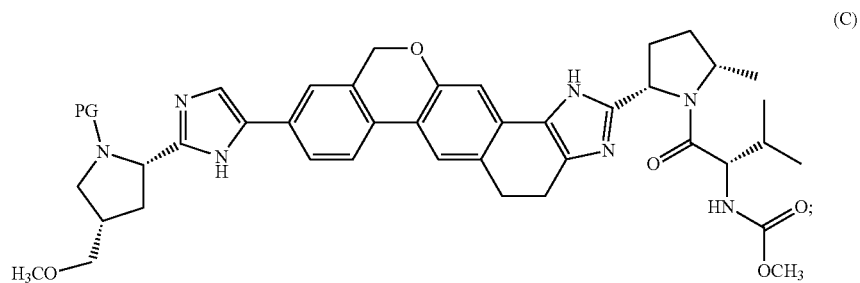

(C)

(d) oxidizing the compound of formula (C) under conditions sufficient to yield a compound of formula (D):

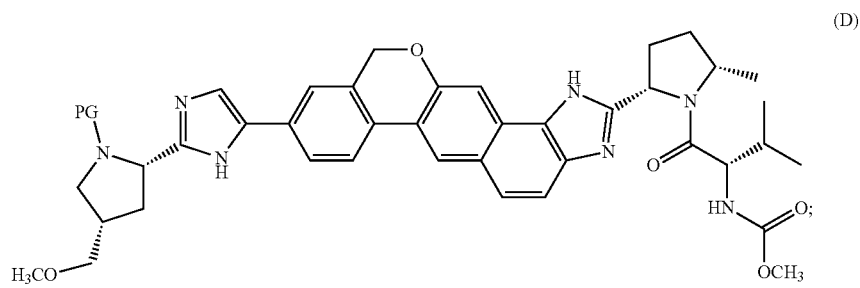

(D)

(e) deprotecting the compound of formula (D) under conditions sufficient to yield a compound of formula (E) or a salt thereof:

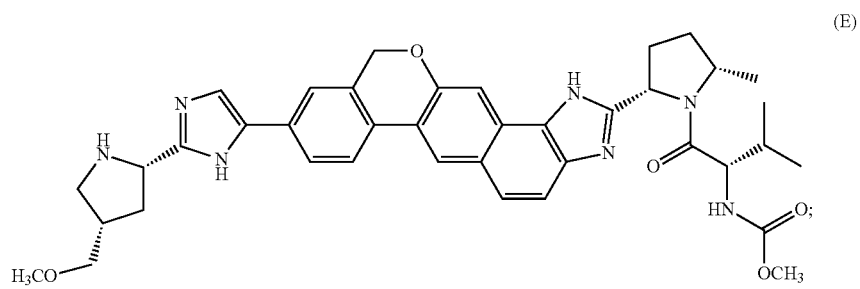 [SMILES: COC[C@@H]1CN[C@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)C1]

(E)

and (f) contacting the compound of formula (E) with a compound of formula (F):

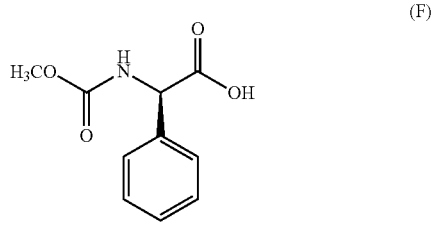 [SMILES: COC(=O)N[C@@H](C(=O)O)c1ccccc1]

under conditions sufficient to yield a compound of formula (A), wherein PG is an amine protecting group.

In certain embodiments, the reaction conditions of step (a) comprise a solvent selected from the group consisting of dichloromethane, 2-methyltetrahydrofuran, tetrahydrofuran, isopropyl acetate, ethyl acetate, tert-butyl methyl ether, cyclopentyl methyl ether, dimethylformamide, acetone, MEK, and MIBK. In certain embodiments, the reaction conditions of step (a) comprise a temperature of from about 10° C. to about 60° C. or from about 10° C. to about 30° C.

In some embodiments, the reaction conditions of step (a) comprise a phosphate salt or a carbonate salt. In certain embodiments, the phosphate salt includes but is not limited to $KH_2PO_4$, $K_3PO_4$, $Na_2HPO_4$, and $Na_3PO_4$. In some embodiments, the carbonate salt includes but is not limited to $Na_2CO_3$, $Cs_2CO_3$, and $NaHCO_3$.

In certain embodiments, the compound of formula (J) is a potassium, a sodium, or a cesium salt.

In certain embodiments, the reaction conditions of step (b) comprise a solvent selected from the group consisting of tetrahydrofuran, 2-methyltetrahydrofuran, dichloromethane, toluene, isopropyl acetate, ethyl acetate, 1-methyl-2-pyrrolidinone, N,N-dimethylacetamide, acetone, MEK, MIBK, and a mixture thereof. In certain embodiments, the reaction conditions of step (b) comprise a temperature of from about 40° C. to about 60° C. or from about 40° C. to about 50° C.

In some embodiments, the reaction conditions of step (b) comprise a phosphate salt or carbonate salt. In certain embodiments, the phosphate salt includes but is not limited to $KH_2PO_4$, $K_3PO_4$, $Na_2HPO_4$, and $Na_3PO_4$. In some embodiments, the carbonate salt includes but is not limited to $Na_2CO_3$, $Cs_2CO_3$, $Li_2CO_3$, and $NaHCO_3$.

In certain embodiments, the compound of formula (H) is a potassium, a sodium, or a cesium salt.

In some embodiments, the reaction conditions of step (c) comprise an amine reagent, wherein the amine reagent comprises ammonium acetate, hexamethyldisilzane, ammonia, ammonium formate, ammonium propionate, ammonium hexanoate, or ammonium octanoate.

In certain embodiments, the reaction conditions of step (c) comprise a solvent selected from the group consisting of toluene, xylene, an alcohol, and a mixture thereof. In certain embodiments, the reaction conditions of step (c) comprise a temperature of from about 60° C. to about 110° C. or from about 85° C. to about 95° C. In some embodiments, the alcohol can be isopropanol, 1-propanol, 1-butanol, 2-butanol, 2-methoxyethanol, or a glycol, such as ethylene glycol or propylene glycol. In some embodiments, the reaction condition comprises a mixture of toluene and isopropanol.

In certain embodiments, the reaction conditions of step (d) comprise an oxidant. In some embodiments, the oxidant is 2,3-dichloro-5,6-dicyano-1,4-benzoquinone.

In certain embodiments, the reaction conditions of step (d) comprise an additive selected from the group consisting of carbonate base (such as potassium carbonate, potassium bicarbonate, sodium carbonate, or sodium bicarbonate), amine (such as triethylamine or diisopropylethylamine), acid (organic acids and inorganic acids), and acetate salts (such as sodium acetate or potassium acetate). In some embodiments, the additive is acetic acid.

In certain embodiments, the reaction conditions of step (d) comprise 2-methyltetrahydrofuran, or a mixture of toluene and tetrahydrofuran. In certain embodiments, the reaction conditions of step (d) comprise a temperature of from about −15° C. to about 80° C. or from about −15° C. to about 10° C. In some embodiments, the temperature is about 0° C.

In certain embodiments, the reaction conditions of step (e) comprise a deprotection reagent, wherein the deprotection reagent may be hydrochloric acid (including wherein hydrochloric acid is generated from acetyl chloride), phosphoric acid, trifluoroacetic acid, p-toluenesulfonic acid, methanesulfonic acid, ethanesulfonic acid, benzenesulfonic acid, p-toluenesulfonic acid, 4-bromobenzenesulfonic acid, thionyl chloride, and trimethylsilyl chloride. A wide range of solvents may be employed, including but not limited to water, methanol, ethanol, acetonitrile, acetone, tetrahydrofuran, 1,4-dioxane, and toluene. Deprotection may proceed at temperatures ranging from about 20° C. to about 110° C. or from about 55° C. to about 65° C.

In certain embodiments, step (e) further comprises neutralizing the compound of formula (E). In some embodiments, neutralizing the compound of formula (E) may be in a variety of organic solvents and aqueous solvents and may be performed at a temperature of from about −20° C. to about 60° C. or from about 5° C. to about 15° C. The neutralization reagent may be a wide variety of bases. In certain embodiments, the base may be sodium methoxide. In some embodiments, the neutralization solvent may be methanol.

In certain embodiments, step (e) further comprises crystallizing the compound of formula (E). In some embodiments, recrystallization of compound formula (E) comprises water, an alcohol (such as 1-propanol, 2-propanol, methanol, or ethanol), or acetonitrile. In some embodiments, the temperature may range from about −20° C. to about 100° C. The temperature may be from about 60° C. and may be ramped to cool to about 20° C. In some embodiments, recrystallization of compound formula (E) comprises a crystallization reagent. The crystallization reagent may be an acid, such as hydrochloric acid, hydrobromic acid, sulfuric acid, ethanesulfonic acid, benzenesulfonic acid, 4-bromobenzenesulfonic acid, oxalic acid, glucuronic acid, or phosphoric acid. In some embodiments, the crystallization reagent is phosphoric acid.

In certain embodiments, the reaction conditions of step (f) comprise a solvent selected from the group consisting of dichloromethane, methanol, N,N-dimethylformamide, and a mixture thereof. In certain embodiments, the reaction conditions of step (f) comprise a temperature of from about −20° C. to about 30° C. or from about 10° C. to about 20° C.

In some embodiments, the reaction conditions of step (f) comprises a coupling agent and an organic base. The coupling agent may be those typically known in the art. In some embodiments, the coupling agent is 4-(4,6-dimethoxy-1,3,5-triazin-2-yl)-4-methylmorpholinium chloride. In some embodiments, the organic base may be an amine. In certain embodiments, the organic base is N-methylmorpholine.

In an embodiment, the compound of formula (D):

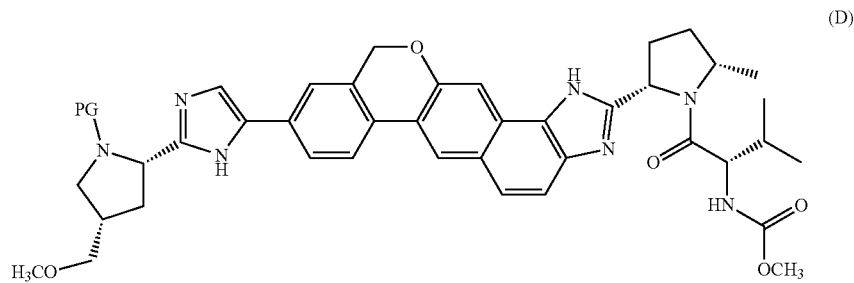

is prepared by (a) contacting a compound of formula (I), stereoisomer thereof, or mixture of stereoisomers thereof:

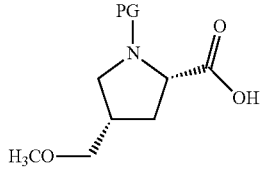

with a compound of formula (J) or salt thereof:

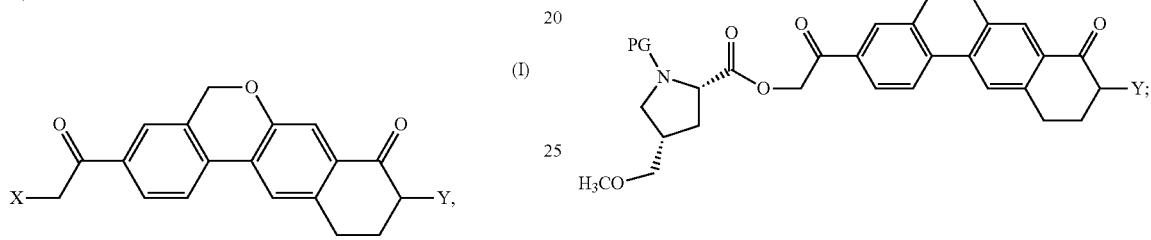

under conditions sufficient to yield a compound of formula (G), stereoisomer thereof, or mixture of stereoisomers thereof:

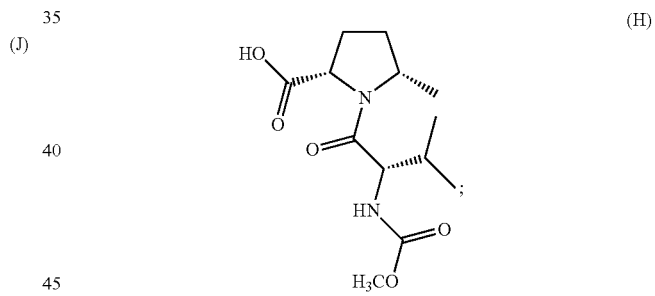

(b) contacting the compound of formula (G) with a compound of formula (H) or salt thereof:

under conditions sufficient to yield a compound of formula (B), stereoisomer thereof, or mixture of stereoisomers thereof:

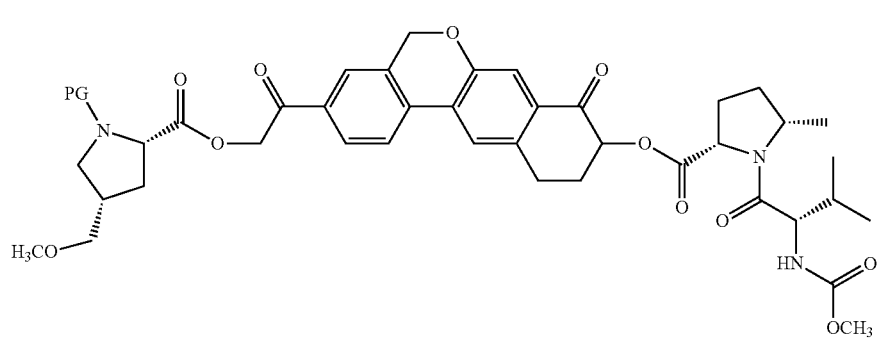

(c) cyclizing a compound of formula (B) under conditions sufficient to yield a compound of formula (C):

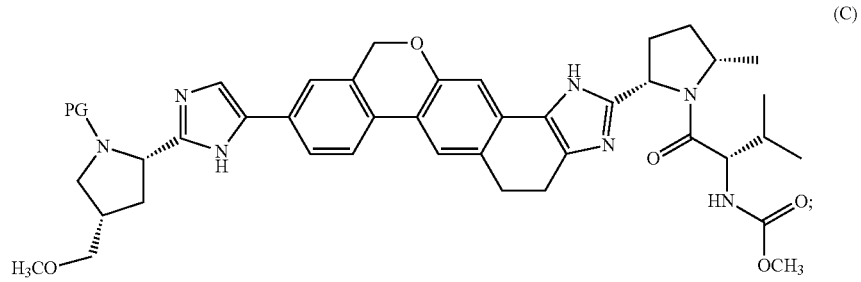

and (d) dehydrogenating a compound of formula (C) under conditions sufficient to yield a compound of formula (D), wherein PG is an amine protecting group, X and Y are each independently selected from the group consisting of halo, —OSO₂R, —OP(O)OR, and —OP(O)(OR)₂, wherein R is alkyl, haloalkyl, or aryl or substituted aryl.

In some embodiments, the substituted aryl may be an aryl having one or more substituents, such as alkyl, alkoxy, hydroxyl, nitro, halogen, and others as discussed above.

In an embodiment, X is bromo and Y is bromo.

In certain embodiments, the reaction conditions of step (a) comprise a solvent selected from the group consisting of dichloromethane, 2-methyltetrahydrofuran, tetrahydrofuran, isopropyl acetate, ethyl acetate, tert-butyl methyl ether, cyclopentyl methyl ether, dimethylformamide, acetone, MEK, and MIBK. In certain embodiments, the reaction conditions of step (a) comprise a temperature of from about 10° C. to about 60° C. or from about 10° C. to about 30° C.

In some embodiments, the reaction conditions of step (a) comprise a phosphate salt or carbonate salt. In certain embodiments, the phosphate salt includes but is not limited to KH₂PO₄, K₃PO₄, Na₂HPO₄, and Na₃PO₄. In some embodiments, the carbonate salt includes but is not limited to Na₂CO₃, Cs₂CO₃, and NaHCO₃.

In certain embodiments, the compound of formula (J) is a potassium, a sodium, or a cesium salt.

In certain embodiments, the reaction conditions of step (b) comprise a solvent selected from the group consisting of tetrahydrofuran, 2-methyltetrahydrofuran, dichloromethane, toluene, isopropyl acetate, ethyl acetate, 1-methyl-2-pyrrolidinone, N,N-dimethylacetamide, acetone, MEK, MIBK, and a mixture thereof. In certain embodiments, the reaction conditions of step (b) comprise a temperature of from about 40° C. to about 60° C. or from about 40° C. to about 50° C.

In some embodiments, the reaction conditions of step (b) comprise a phosphate salt or carbonate salt. In certain embodiments, the phosphate salt includes but is not limited to KH₂PO₄, K₃PO₄, Na₂HPO₄, and Na₃PO₄. In some embodiments, the carbonate salt includes but is not limited to Na₂CO₃, Cs₂CO₃, Li₂CO₃, and NaHCO₃.

In certain embodiments, the compound of formula (H) is a potassium, a sodium, or a cesium salt.

In some embodiments, the reaction conditions of step (c) comprises an amine reagent, wherein the amine reagent comprises ammonium acetate, hexamethyldisilzane, ammonia, ammonium formate, ammonium propionate, ammonium hexanoate, or ammonium octanoate.

In certain embodiments, the reaction conditions of step (c) comprise a solvent selected from the group consisting of toluene, xylene, an alcohol, and a mixture thereof. In certain embodiments, the reaction conditions of step (c) comprise a temperature of from about 60° C. to about 110° C. or from about 85° C. to about 95° C. In some embodiments, the alcohol can be isopropanol, 1-propanol, 1-butanol, 2-butanol, 2-methoxyethanol, or a glycol, such as ethylene glycol or propylene glycol. In some embodiments, the reaction condition comprises a mixture of toluene and isopropanol.

In certain embodiments, the reaction conditions of step (d) comprise an oxidant. In some embodiments, the oxidant is 2,3-dichloro-5,6-dicyano-1,4-benzoquinone.

In certain embodiments, the reaction conditions of step (d) comprise an additive selected from the group consisting of carbonate base (such as potassium carbonate, potassium bicarbonate, sodium carbonate, or sodium bicarbonate), amine (such as triethylamine or diisopropylethylamine), acid (organic acids and inorganic acids), and acetate salts (such as sodium acetate or potassium acetate). In some embodiments, the additive is acetic acid.

In certain embodiments, the reaction conditions of step (d) comprise 2-methyltetrahydrofuran, or mixture of toluene and tetrahydrofuran. In certain embodiments, the reaction conditions of step (d) comprise a temperature of from about −15° C. to about 80° C. or from about −15° C. to about 10° C. In some embodiments, the temperature is about 0° C.

In one embodiment, provided is a process for preparing a compound of formula (C):

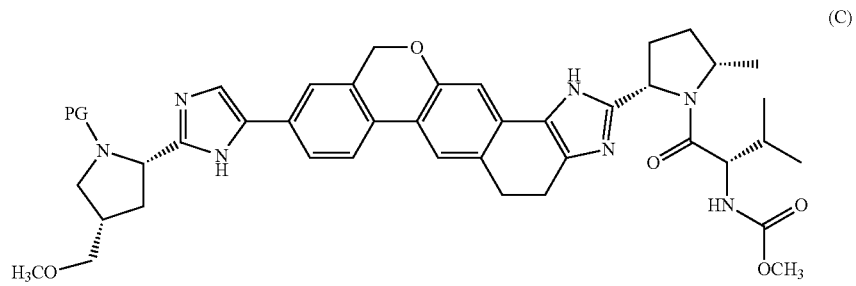

comprising (a) contacting a compound of formula (I), stereoisomer thereof, or mixture of stereoisomers thereof:

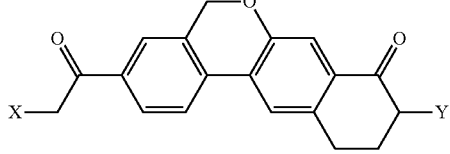

with a compound of formula (J) or salt thereof:

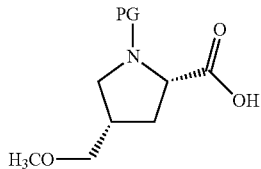

under conditions sufficient to yield a compound of formula (G), stereoisomer thereof, or mixture of stereoisomers thereof:

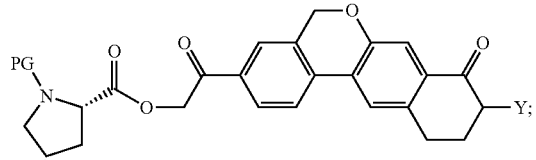

(b) contacting the compound of formula (G) with a compound of formula (H) or salt thereof:

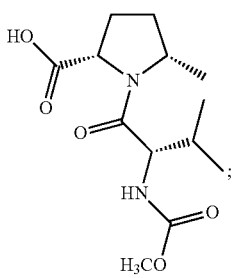

under conditions sufficient to yield a compound of formula (B), stereoisomer thereof, or mixture of stereoisomers thereof:

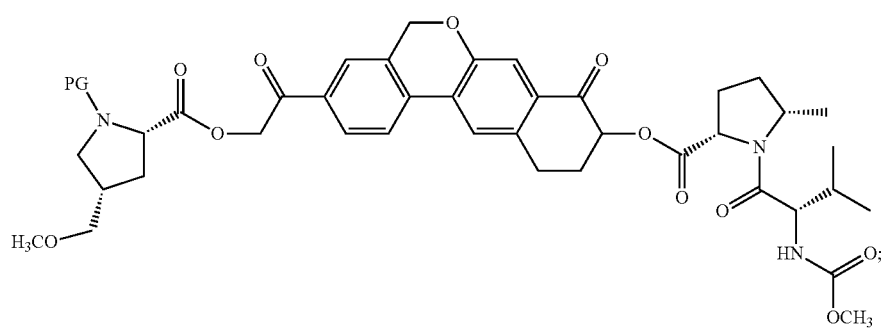

and (c) cyclizing a compound of formula (B) under conditions sufficient to yield a compound of formula (C), wherein PG is an amine protecting group, X and Y are each independently selected from the group consisting of halo, —OSO$_2$R, —OP(O)OR, and —OP(O)(OR)$_2$, wherein R is alkyl, haloalkyl, or aryl or substituted aryl.

In some embodiments, the substituted aryl may be an aryl having one or more substituents, such as alkyl, alkoxy, hydroxyl, nitro, halogen, and others as discussed above.

In an embodiment, X is bromo and Y is bromo.

In certain embodiments, the reaction conditions of step (a) comprise a solvent selected from the group consisting of dichloromethane, 2-methyltetrahydrofuran, tetrahydrofuran, isopropyl acetate, ethyl acetate, tert-butyl methyl ether, cyclopentyl methyl ether, dimethylformamide, acetone, MEK, and MIBK. In certain embodiments, the reaction conditions of step (a) comprise a temperature of from about 10° C. to about 60° C. or from about 10° C. to about 30° C.

In some embodiments, the reaction conditions of step (a) comprise a phosphate salt or carbonate salt. In certain embodiments, the phosphate salt includes but is not limited to KH$_2$PO$_4$, K$_3$PO$_4$, Na$_2$HPO$_4$, and Na$_3$PO$_4$. In some embodiments, the carbonate salt includes but is not limited to Na$_2$CO$_3$, Cs$_2$CO$_3$, and NaHCO$_3$.

In certain embodiments, the compound of formula (J) is a potassium, a sodium, or a cesium salt.

In certain embodiments, the reaction conditions of step (b) comprise a solvent selected from the group consisting of tetrahydrofuran, 2-methyltetrahydrofuran, dichloromethane, toluene, isopropyl acetate, ethyl acetate, 1-methyl-2-pyrrolidinone, N,N-dimethylacetamide, acetone, MEK, MIBK, and a mixture thereof. In certain embodiments, the reaction conditions of step (b) comprise a temperature of from about 40° C. to about 60° C. or from about 40° C. to about 50° C.

In some embodiments, the reaction conditions of step (b) comprise a phosphate salt or carbonate salt. In certain embodiments, the phosphate salt includes but is not limited to KH$_2$PO$_4$, K$_3$PO$_4$, Na$_2$HPO$_4$, and Na$_3$PO$_4$. In some embodiments, the carbonate salt includes but is not limited to Na$_2$CO$_3$, Cs$_2$CO$_3$, Li$_2$CO$_3$, and NaHCO$_3$.

In certain embodiments, the compound of formula (H) is a potassium, a sodium, or a cesium salt.

In some embodiments, the reaction conditions of step (c) comprises an amine reagent, wherein the amine reagent comprises ammonium acetate, hexamethyldisilzane, ammonia, ammonium formate, ammonium propionate, ammonium hexanoate, or ammonium octanoate.

In certain embodiments, the reaction conditions of step (c) comprise a solvent selected from the group consisting of toluene, xylene, an alcohol, and a mixture thereof. In certain embodiments, the reaction conditions of step (c) comprise a temperature of from about 60° C. to about 110° C. or from about 85° C. to about 95° C. In some embodiments, the alcohol can be isopropanol, 1-propanol, 1-butanol, 2-butanol, 2-methoxyethanol, or a glycol, such as ethylene glycol or propylene glycol. In some embodiments, the reaction condition comprises a mixture of toluene and isopropanol.

In one embodiment, provided is a process for preparing a compound of formula (I-a), stereoisomer thereof, or mixture of stereoisomers thereof:

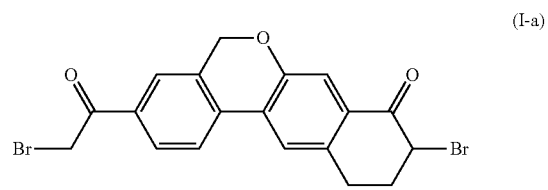 [SMILES: O=C(CBr)c1ccc2c(c1)COc1cc3c(cc1-2)CCC(Br)C3=O]
(I-a)

comprising the steps of:
(a) cyclizing a compound of formula (L):

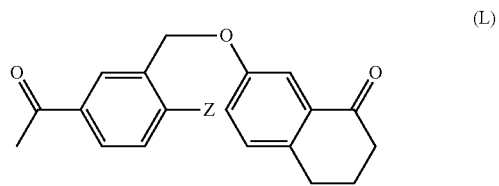
(L)

under conditions sufficient to yield a compound of formula (K):

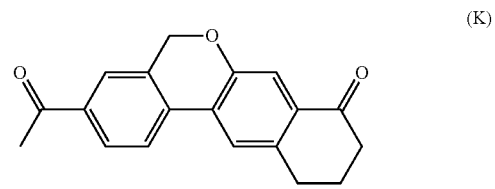
(K)

and
(b) brominating the compound of formula (K) under conditions sufficient to yield a compound of formula (I-a), wherein Z is hydrogen, halo, OSO$_2$R$^1$, —BF$_3^-$, —B(OR$^2$)$_2$, —CO$_2$H, or —NR$^1_3$ wherein R$^1$ is alkyl, haloalkyl, aryl or substituted aryl, and R$^2$ is alkyl. In some embodiments, the substituted aryl may be an aryl having one or more substituents, such as alkyl, alkoxy, hydroxyl, nitro, halogen, and others as discussed above.

In certain embodiments, the reaction conditions of step (a) comprise a solvent selected from the group consisting of N,N-dimethylacetamide, N,N-dimethylformamide, and acetonitrile. In certain embodiments, the reaction conditions of step (a) comprise a temperature of from about 20° C. to about 80° C. In some embodiments, the temperature is about 80° C.

In certain embodiments, the reaction conditions of step (a) comprise at least one of palladium catalyst, carbonate salt, and phosphine reagent. In some embodiments, the palladium catalyst may be palladium (II) acetate. In some embodiments, the phosphine reagent may be PPh$_3$. In some embodiments, the carbonate salt may be potassium carbonate. The reaction conditions may further comprise tetrabutylammonium bromide. The reaction may take place from about 5 hours to about 7 hours.

In certain embodiments, the reaction conditions of step (b) comprise a brominating reagent selected from the group consisting of pyridinium tribromide, bromine, and N-bromosuccinimide. In certain embodiments, the reaction conditions of step (b) comprise a solvent selected from the group consisting of dichloromethane, methanol, and a mixture thereof. In certain embodiments, the reaction conditions of step (b) comprise a temperature of about 20° C. The reaction may take place for about 2 hours to about 5 hours.

In one embodiment, compound of formula (L) is prepared by contacting a compound of formula (M):

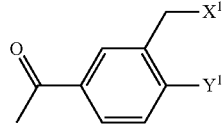

(M)

with a compound of formula (N):

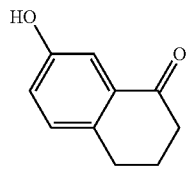

(N)

under conditions sufficient to yield the compound of formula (L), wherein $X^1$ is a leaving group, $Y^1$ is hydrogen, halo, or trifluoromethanesulfonate, and Z is hydrogen, halo, —$OSO_2R^1$, —$BF_3^-$, —$B(OR^2)_2$, —$CO_2H$, or —$NR^1_3$ wherein $R^1$ is alkyl, haloalkyl, aryl or substituted aryl, and $R^2$ is alkyl. In some embodiments, $X^1$ is halo, —OH, or —$S(O)_2R^3$, and $R^3$ is alkyl, haloalkyl, or aryl, and the aryl is optionally substituted with halo, alkyl, haloalkyl, nitro, hydroxyl, or alkoxy.

In certain embodiments, the reaction conditions comprise a solvent selected from the group consisting of N,N-dimethylacetamide, tetrahydrofuran, 2-methyltetrahydrofuran, N,N-dimethylformamide, and acetonitrile. In certain embodiments, the reaction conditions comprise a temperature of from about 20° C. to about 70° C. In some embodiments, the temperature is about 70° C. In some embodiments, the reaction conditions comprise a carbonate base, such as potassium carbonate. Sodium iodide may also be used. The reaction may take place for about 2 hours.

In one embodiment, provided is a process for preparing a compound of formula (I-a):

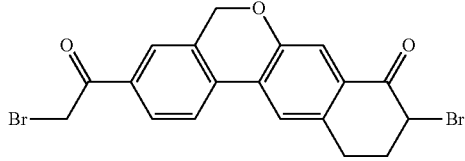

(I-a)

comprising reacting a compound of formula (O):

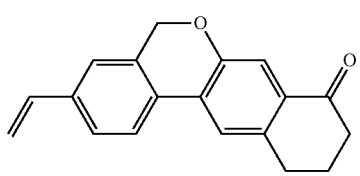

(O)

under conditions sufficient to yield a compound of formula (I-a).

In certain embodiments, the reaction conditions comprise an oxidizing reagent and palladium catalyst. The palladium catalyst may be dichloro[2-(4,5-dihydro-2-oxazolyl)quinoline]palladium(II). The oxidizing agent may be tert-butylhydroperoxide. An additive may be used, such as silver tetrafluoroborate.

In some embodiments, the reaction conditions comprise a solvent selected from the group consisting of N,N-dimethylformamide, water, and a mixture thereof. In some embodiments, the reaction conditions comprise a temperature of from about 20° C. to about 25° C. or from about 0° C. to about 100° C. The reaction may take place for about 30 minutes to about 12 hours or from about 30 minutes to about 48 hours.

In one embodiment, a compound of formula (K) is prepared by hydrolyzing a compound of formula (P):

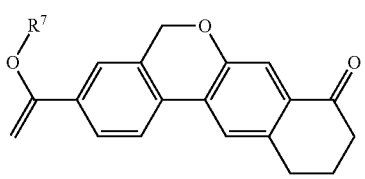

(P)

wherein $R^7$ is alkyl, under conditions sufficient to yield a compound of formula (K).

In certain embodiments, the reaction conditions comprise an acid. In some embodiments, the reaction conditions comprise a solvent selected from the group consisting of dichloromethane, water, and a mixture thereof. In some embodiments, the reaction conditions comprise a temperature of from about 5° C. to about 35° C. or from about 0° C. to about 100° C.

The acid may be trifluoroacetic acid. The reaction may take place from about 30 minutes to about 2 hours or from about 30 minutes to about 48 hours.

In one embodiment, a compound of formula (K) is prepared by derivatizing a compound of formula (Q):

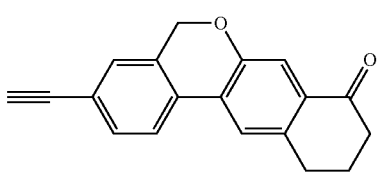

(Q)

under conditions sufficient to yield the compound of formula (K).

In certain embodiments, the reaction conditions comprise an acid. In some embodiments, the reaction conditions comprise a solvent selected from the group consisting of an organic solvent, aqueous solvent, and a mixture thereof. In certain embodiments, the reaction conditions comprise a temperature of from about 0° C. to about 100° C., 60° C. to about 70° C., or about 65° C. The reaction may take place in about 0.2 hours to about 48 hours or for about 3 hours. In some embodiments, the solvent may be water. In some embodiments, the acid may be trifluoroacetic acid.

In one embodiment, provided is a process for preparing a compound of formula (H):

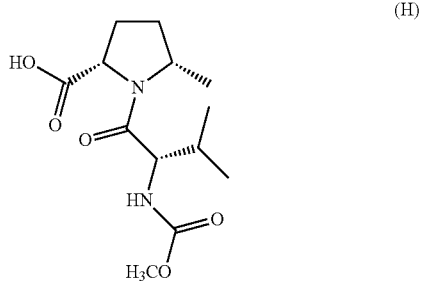 [SMILES: COC(=O)N[C@H](C(=O)N1[C@@H](C)CC[C@H]1C(=O)O)C(C)C]

comprising the steps of:
(a) contacting a salt of a compound of formula (R):

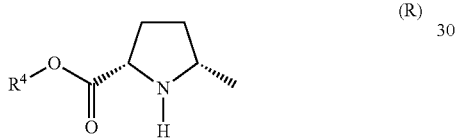

with a compound of formula (S):

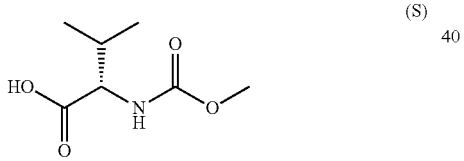

under conditions sufficient to yield the compound of formula (T):

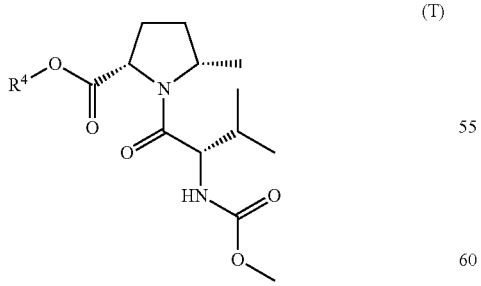

and
(b) hydrolyzing the compound of formula (T) under conditions sufficient to yield the compound of formula (H), wherein $R^4$ is an optionally substituted alkyl or optionally substituted aryl.

In some embodiments, the reaction conditions of step (a) comprise a coupling reagent. In certain embodiments, the reaction conditions comprise a solvent selected from the group consisting of N,N-dimethylformamide, N,N-dimethylacetamide, N-methyl-2-pyrrolidone, dichloromethane, tetrahydrofuran, and 2-methyltetrahydrofuran. In certain embodiments, the reaction conditions comprise a temperature of from about 0° C. to about 25° C. In some embodiments, the coupling reagent can be typical peptide coupling reagents, such as N,N,N',N'-Tetramethyl-O-(benzotriazol-1-yl)uronium tetrafluoroborate. In some embodiments, a base, such as diisopropylethylamine, can be used.

In certain embodiments, the reaction conditions of step (b) comprise a hydroxide base. In certain embodiments, the reaction conditions of step (b) comprise a solvent selected from the group consisting of tetrahydrofuran, an alcohol (such as methanol, ethanol, or isopropanol), water, N,N-dimethylformamide, N,N-dimethylacetamide, N-methyl-2-pyrrolidone, and a mixture thereof. In certain embodiments, the reaction conditions of step (b) comprise a temperature of from about 15° C. to about 25° C. In some embodiments, the hydroxide base may be sodium hydroxide, potassium hydroxide, or lithium hydroxide. In some embodiments, the solvent may be a mixture of tetrahydrofuran, methanol, and water.

In one embodiment, a compound of formula (R) is prepared by (a) cyclizing a compound of formula (U):

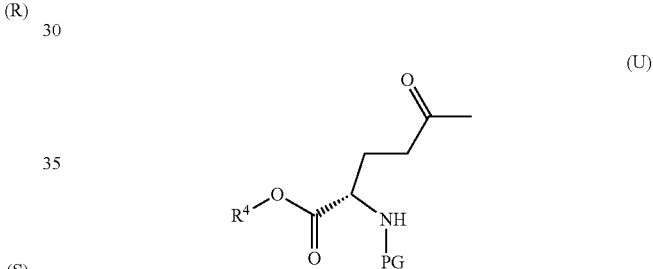

under conditions sufficient to yield the compound of formula (V):

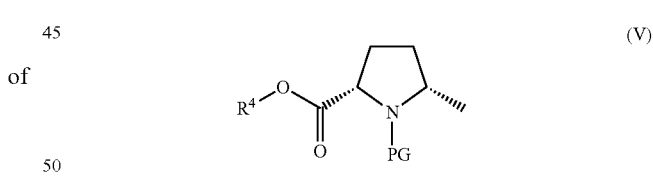

and
(b) contacting the compound of formula (V) with an acid under conditions sufficient to yield the complex of formula (R), wherein PG is an amine protecting group and $R^4$ is an optionally substituted alkyl or optionally substituted aryl.

In certain embodiments, the reaction conditions of step (a) comprise a borohydride reagent and an organic acid. In certain embodiments, the reaction conditions of step (a) comprise an alkyl acetate solvent. In certain embodiments, the reaction conditions of step (a) comprise a temperature of from about −10° C. to about 0° C. or about −10° C. to about 20° C. The alkyl acetate solvent may be, for example, ethyl acetate, isopropyl acetate, propyl acetate, butyl acetate, and the like. The borohydride reagent may be sodium triacetoxyborohydride, sodium borohydrodride, or sodium tripropionoxyborohydride. The organic acid may be trifluoroacetic acid, acetic acid, or propionic acid. In some embodiments, sodium triacetoxyborohydride and trifluoroacetic acid may be used.

In some embodiments, the reaction conditions of step (b) comprise a solvent selected from the group consisting of dichloromethane, toluene, ethyl acetate, isopropyl acetate, methanol, ethanol, and isoprophanol. In some embodiments, the reaction conditions of step (b) comprise ethyl acetate. In some embodiments, the reaction conditions of step (b) comprise a temperature of from about 15° C. to about 110° C. or about 15° C. to about 80° C.

In some embodiments, the acid is selected from the group consisting of trifluoroacetic acid, hydrochloric acid, methanesulfonic acid, benezensulfonic acid, and napthalenesulfonic acid. In some embodiments, the complex of formula (R) is a trifluoroacetate salt, hydrochloride salt, mesylate salt, besylate salt, or naphthalenesulfonate salt.

In some embodiments, the acid is para-toluenesulfonic acid, and the salt of formula (R) is a para-toluenesulfonic salt. In such embodiments, $R^4$ is an ethyl group. In some embodiments, the acid is hydrochloric acid, and the salt of formula (R) is a hydrochloric salt. In such embodiments, the $R^4$ can be a benzyl group.

In one embodiment, provided is a process for preparing a complex of formula (R-a):

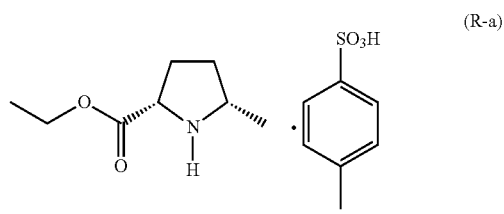

(R-a)

comprising the steps of:
(a) cyclizing a compound of formula (U'):

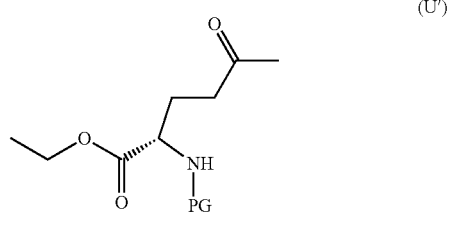

(U')

under conditions sufficient to yield the compound of formula (V'):

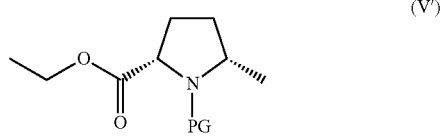

(V')

and
(b) contacting the compound of formula (V') with para-toluenesulfonic acid, wherein PG is an amine protecting group, under conditions sufficient to yield the complex of formula (R-a).

In certain embodiments, the reaction conditions of step (a) comprise a borohydride reagent and an organic acid. In certain embodiments, the reaction conditions of step (a) comprise an alkyl acetate solvent. In certain embodiments, the reaction conditions of step (a) comprise a temperature of from about −10° C. to about 0° C. or about −10° C. to about 20° C. The alkyl acetate solvent may be, for example, ethyl acetate, isopropyl acetate, N-propyl acetate, butyl acetate, and the like. The borohydride reagent may be sodium triacetoxyborohydride, sodium borohydrodride, or sodium tripropionoxyborohydride. The organic solvent may be trifluoroacetic acid, acetic acid, or propionic acid. In some embodiments, sodium triacetoxyborohydride and trifluoroacetic acid may be used. In some embodiments, step (a) comprises cyclizing and reducing a compound of formula (U').

In some embodiments, the reaction conditions of step (b) comprise a solvent selected from the group consisting of dichloromethane, toluene, ethyl acetate, isopropyl acetate, methanol, ethanol, and isoprophanol. In some embodiments, the reaction conditions of step (b) comprise ethyl acetate. In some embodiments, the reaction conditions of step (b) comprise a temperature of from about 15° C. to about 110° C. or about 15° C. to about 80° C.

In one embodiment, provided is a process for preparing a compound of formula (J) or salt thereof:

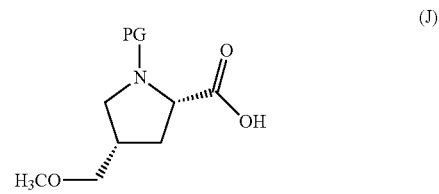

(J)

comprising the steps of:
(a) contacting a compound of formula (W):

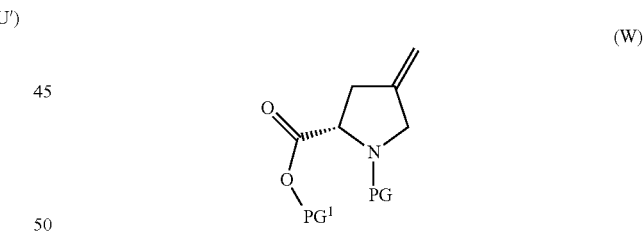

(W)

with a hydroboration reagent under conditions sufficient to yield a compound of formula (X):

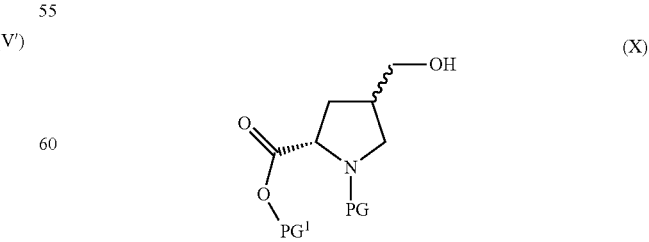

(X)

(b) methylating the compound of formula (X) under conditions sufficient to yield a compound of formula (Y):

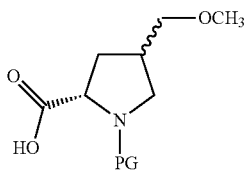
(Y)

and (c) resolving the compound of formula (Y) under conditions sufficient to yield a compound of formula (J), wherein PG is an amine protecting group and PG¹ is a carboxylic acid protecting group.

In some embodiments, the reaction conditions of step (a) comprise a hydroboration reagent, wherein the hydroboration reagent is borane-dimethylsulfide. In some embodiments, the reaction conditions of step (a) comprise a solvent selected from the group consisting of tetrahydrofuran, methyl tert-butyl ether, 2-methyltetrahydrofuran, isopropyl acetate, isobutyl acetate, diethyl ether, isopropyl ether, toluene, and N,N-dimethylformamide. In some embodiments, the reaction conditions of step (a) comprise a temperature of from about −30° C. to about −20° C. or about 0° C. to about 100° C.

In some embodiments, the reaction conditions of step (b) may comprise an acid and methanol. In some embodiments, the acid may be hydrochloric acid. In some embodiments, the reaction conditions of step (a) comprise a temperature of from about 20° C. to about 60° C. or about 25° C.

In an embodiment, a compound of formula (J) or salt thereof is prepared by:

(a) contacting a compound of formula (Z):

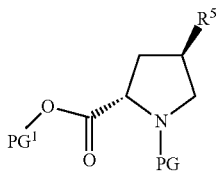
(Z)

with HCN or salt thereof under conditions sufficient to yield a compound of formula (AA):

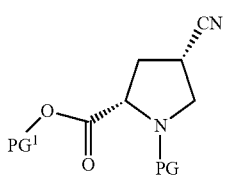
(AA)

(b) contacting the compound of formula (AA) with an acyl halide or acid and R⁶—OH under conditions sufficient to yield a compound of formula (BB):

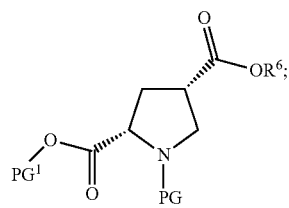
(BB)

(c) selective hydrolysis of the compound of formula (BB) under conditions sufficient to form a compound of formula (CC):

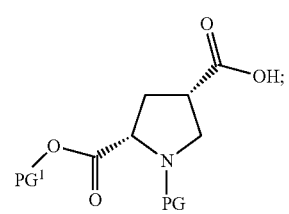
(CC)

(d) contacting the compound of formula (CC) with a borane reagent under conditions sufficient to yield a compound of formula (DD):

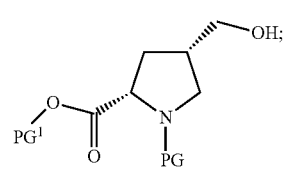
(DD)

and (e) methylating the compound of formula (DD) under conditions sufficient to yield a compound of formula (J), wherein R⁵ is a leaving group, R⁶ is an optionally substituted alkyl, PG is an amine protecting group, and PG¹ is a carboxylic acid protecting group.

In some embodiments, R⁵ may be halo, —OH, or —OSO₂R⁸, wherein R⁸ is alkyl, haloalkyl, aryl, or substituted aryl. In some embodiments, R⁵ may be —OTs. In some embodiments, the reaction conditions of step (a) comprise a sodium or potassium salt of HCN. In certain embodiments, the reaction conditions of step (a) comprise a solvent selected from the group consisting of dimethylsulfoxide, dimethylformamide, or dimethylacetamide.

In certain embodiments, the reaction conditions of step (b) comprise an acid. In certain embodiments, the reaction conditions of step (b) comprise a solvent selected from the group consisting of methanol, dioxane, chloroform, benzene, and nitrobenzene. In certain embodiments, the reaction conditions of step (b) comprise a temperature of from about 20° C. to about 60° C. In some embodiments, the temperature may be about 55° C. The acid may be hydrochloric acid, sulfuric acid, methanesulfonic acid, hydrobromic acid, camphorsulfonic acid, para-toluene sulfonic acid, or acetic acid.

In certain embodiments, the reaction conditions of step (b) may further comprise an additional step to add a protecting group(s) if necessary (e.g. if protecting groups have been cleaved during the reaction). Such methods are well-known in the art and can vary based on the protection group used as described herein. For example, in some embodiments, di-tert-butyl dicarbonate may be used along with sodium bicarbonate and ethyl acetate at a temperature of about 20° C.

In certain embodiments, the reaction conditions of step (c) comprise a hydroxide salt. In certain embodiments, the reaction conditions of step (c) comprise a solvent selected from the group consisting of tetrahydrofuran, methanol, and 2-methyltetrahydrofuran. In certain embodiments, the reaction conditions of step (c) comprise a temperature of from about −20° C. to about 20° C. or about 0° C. The hydroxide salt may be sodium hydroxide, lithium hydroxide, potassium hydroxide, or barium hydroxide.

In certain embodiments, the reaction conditions of step (d) comprise a solvent selected from the group consisting of 2-methyltetrahydrofuran, methanol, ethanol, tetrahydrofuran, and water. In certain embodiments, the reaction conditions of step (d) comprise a temperature of from about −20° C. to about 40° C. or about 20° C.

In some embodiments, the borane reagent comprises diborane or a borane complex, wherein the borane complex comprises a borane dimethyl sulfide complex, borane-tetrahydrofuran complex, or a borane-amine complex.

In some embodiments, the reaction conditions of step (e) comprise methyl iodide and a base selected from the group consisting of a hydroxide salt, 2,6-lutidine, 2,6-di-tert-butylmethyl pyridine, and potassium tert-butoxide. In some embodiments, the reaction conditions of step (e) comprise a solvent selected from the group consisting of tetrahydrofuran, dichloromethane, acetonitrile, water, methanol, dimethyl sulfoxide, and toluene. In some embodiments, the reaction conditions of step (e) comprise a temperature of from about −10° C. to about 40° C. or from about −4° C. to about 1° C. In some embodiments, the base is sodium hydroxide.

The present processes may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula A, B, C, D, E, F, G, H, I, J, K, L, M, N, O, P, Q, R, S, T, U, V, W, X, Y, Z, AA, BB, CC, DD, EE, A-a, A-b, B-a, C-a, D-a, E-a, E-b, G-a, G', I-a, I-b, J-a, L-a, M-a, M-b, M-c, P-a, R-a, T-a, U-a, U', V-a, V', W-a, X-a, Y-a, AA-a, BB-a, BB-b, CC-a, DD-a, DD-b, or other formulas or compounds disclosed herein (e.g. numbered compounds 1-1, 1-2, etc.), may be accomplished as described in the following examples. If available, reagents may be purchased commercially, e.g. from Sigma Aldrich or other chemical suppliers.

Compounds

In other embodiments, the disclosure provides for intermediate compounds that are useful in the processes described herein. Thus, for instance, one embodiment is a compound of the formula (L):

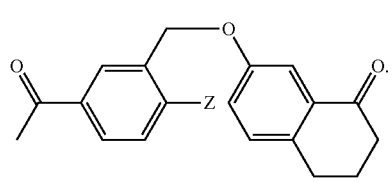

(L)

wherein Z is hydrogen, halo, —OSO$_2$R$^1$, —BF$_3^-$, —B(OR$^2$)$_2$, —CO$_2$H, or —NR$^1_3$ wherein R$^1$ is alkyl, haloalkyl, aryl, substituted aryl, heteroaryl, or substituted heteroaryl, and R$^2$ is alkyl.

In an embodiment, Z is bromo. In some embodiments, Z is chloro. In some embodiments, the substituted aryl may be an aryl having one or more substituents, such as alkyl, alkoxy, hydroxyl, nitro, halogen, and others as discussed above.

In another embodiment, provided is a compound of formula (Q):

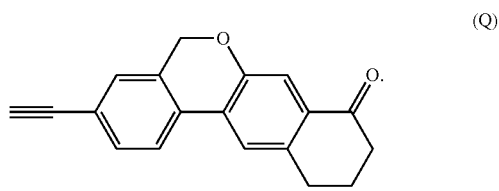 [SMILES: C#Cc1ccc2c(c1)COc1cc3c(cc1-2)CCCC3=O]

(Q)

EXAMPLES

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, may be accomplished as described in the following examples. If available, reagents may be purchased commercially, e.g. from Sigma Aldrich or other chemical suppliers. Unless otherwise noted, the starting materials for the following reactions may be obtained from commercial sources.

Example 1

Synthesis of Compound (H)

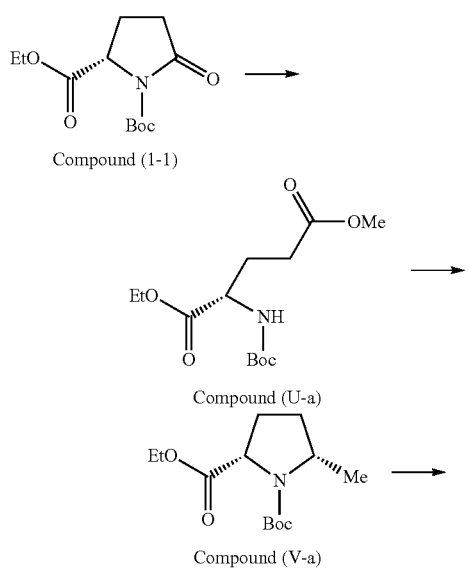

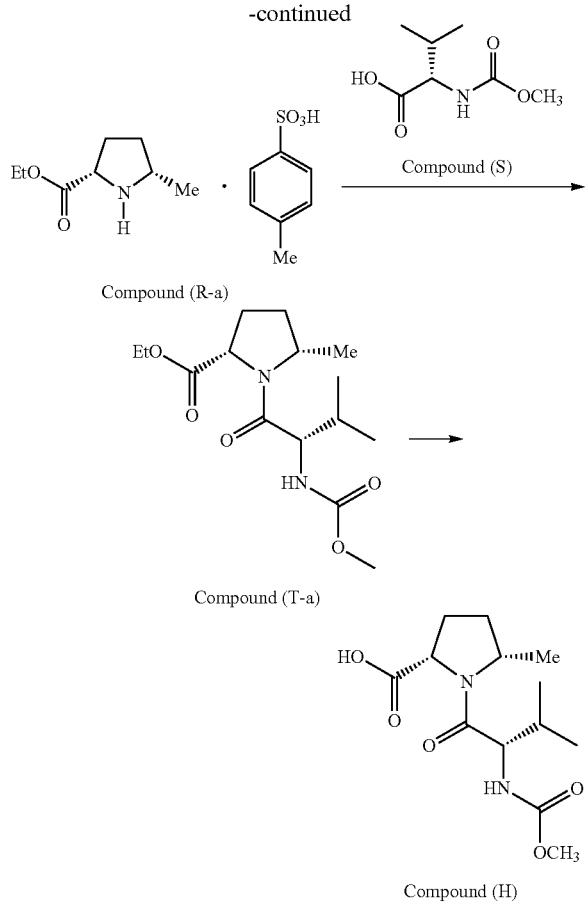

Grignard Addition: Conversion of Compound (1-1) to Compound (U-a)

A reaction vessel was charged with THF (30 mL) followed by 3 M MeMgBr in THF (19.4 ml, 58.4 mmol, 1.5 equiv). The solution was cooled to about −12° C. and then a solution of N-Boc-pyroglutamic acid ethyl ester (10.0 g, 38.9 mmol, 1 equiv) (Compound (1-1)) in THF (20 mL) was added into the reaction contents over 30 minutes maintaining internal temperature of about less than −5° C. Upon reaction completion, 20% aq NH$_4$Cl (50 mL) was added and the mixture was phase separated. The aqueous phase was extracted with EtOAc (50 mL) and the combined organic phases were then washed with 1:1 (v/v) 20% aq NH$_4$Cl/10% aq NaCl (50 mL). The organic phase was polish filtered through a Celite pad and then concentrated by rotary evaporation and further dried to afford Compound (U-a): $^1$H NMR (400 MHz, CDCl3) δ 5.24-4.94 (br s, 1H), 4.37-3.95 (m, 3H), 2.70-2.36 (m, 2H), 2.30-1.97 (m, 4H), 1.96-1.76 (m, 1H), 1.61-1.38 (m, 9H), 1.36-1.05 (m, 3H).

Alternative reagents and reaction conditions to those disclosed above may also be employed. For example, in lieu of N-Boc-pyroglutamic acid ethyl ester, alternative starting material may be N-Boc-pyroglutamic acid benzyl ester, N-Boc-pyroglutamic acid methyl ester, N-Boc-pyroglutamic acid isopropyl ester, N-Boc-pyroglutamic acid t-butyl ester. Additionally, the Grignard reagent may be methylmagnesium chloride in lieu of methylmagnesium bromide.

Alternative solvents may be used in the reaction, such as tetrahydrofuran, methyl-tetrahydrofuran, t-butylmethyl ether, and cyclopentyl methyl ether. The reaction may also take place in temperatures ranging from about −78° C. to about 10° C. or about −10° C. to about 0° C.

Reductive Cyclization: Conversion of Compound (U-a) to Compound (V-a)

A reaction flask was charged with sodium triacetoxyborohydride (9.7 g, 46 mmol, 1.3 equiv) and EtOAc (48 mL). The mixture was cooled to about −10° C. and a solution of Compound (U-a) (9.5 g, 35 mmol, 1 equiv) in EtOAc (48 mL) was added followed by trifluoroacetic acid (11.5 mL, 150 mmol, 4.3 equiv) while maintaining content temperature at less than 0° C. Upon reaction completion, 20% aq K$_2$HPO$_4$ (25 mL) was added and the mixture was phase separated. The organic phase was washed with 20% aq K$_2$HPO$_4$ (3×25 mL) followed by H$_2$O (25 mL) and then concentrated and further dried to afford Compound (V-a). $^1$H NMR (400 MHz, CDCl3) δ 4.46-3.77 (m, 4H), 2.34-1.79 (m, 9H), 1.73-0.98 (m, 10H).

Alternative reagents and reaction conditions to those disclosed above may also be employed. For example, sodium tristrifluoroacetoxyborohydride or sodium tripropionyloxyborohydride may be used in lieu of sodium triacetoxyborohydride. Additionally, in lieu of trifluoroacetic acid, acetic acid or prioionic acid may be used. Alternative solvents may include isopropyl acetate, propyl acetate, and butyl acetate, and temperatures ranging from about −10 to about 0° C. or about −10 to about 20° C. may be employed.

Deprotection and Salt Formation: Conversion of Compound (V-a) to Compound (R-a)

A reaction flask was charged with para-toluenesulfonic acid monohydrate (6.6 g, 35 mmol, 1 equiv) and then a solution of Compound (V-a) (11.0 g, assumed 35 mmol, 1 equiv) in EtOAc (40 mL) was polish filtered through a pad of Celite into the flask followed by a rinse forward of EtOAc (10 mL). The mixture was warmed to about 50° C. and held for about 90 min. Upon reaction completion, the slurry was cooled to about 20° C. and then filtered, rinsing forward EtOAc (2×10 mL). The solids were dried under vacuum at about 40° C. to afford Compound (R-a). $^1$H NMR (400 MHz, CD$_3$OD) δ 7.70 (d, J=4.6 Hz, 2H), 7.23 (d, J=4.6 Hz, 2H), 4.54-4.40 (m, 1H), 4.40-4.18 (m, 2H), 3.88-3.64 (m, 1H), 2.53-2.33 (m, 5H), 2.32-2.08 (m, 2H), 1.80-1.56 (m, 1H), 1.43 (d, J=6.6 Hz, 3H), 1.30 (t, J=7.1 Hz, 3H).

Alternative reagents and reaction conditions to those disclosed above may also be employed. For example, in lieu of para-toluenesulfonic acid, alternative reagents may be trifluoroacetic acid, anhydrous HCl, hydrochloric acid, methanesulfonic acid, benzenesulfonic acid, naphthalenesulfonic acid. Various solvents may also be used, such as dichloromethane, toluene, isopropyl acetate, methanol, ethanol, and isopropanol. The reaction may be carried out at temperatures of about 15° C. to about 110° C. The resultant salt may be isolated as a trifluoroacetate salt, hydrochloride salt, mesylate salt, besylate salt, and naphthalenesulfonate salt.

Peptide Coupling of Compound (R-a) to Form Compound (T-a)

A reaction vessel was charged with Compound (R-a) (30.0 g, 91.0 mmol, 1 equiv), 2-(S)-methoxycarbonylamino-3-methyl-butyric acid (17.5 g, 100 mmol, 1.10 equiv), and HATU (38.0 g, 100 mmol, 1.10 equiv) followed by dichloromethane (450 mL) and diisopropylethylamine (49.6 mL, 300 mmol, 3.30 equiv). After about 1 h, the mixture was concentrated by rotary evaporation and diluted with ethyl acetate (200 mL). The solution was washed with 10% HCl (4×50 mL) followed by 5% Na$_2$CO$_3$ (4×50 mL) and 20% NaCl (50 mL). The organic phase was filtered through Celite, concentrated, and then evaporated from dichloromethane to produce crude Compound (T-a) that was used without further purification.

Alternative reagents and reaction conditions to those disclosed above may also be employed. For example, alternative reagents may be T3P, 4-(4,6-dimethoxy-1,3,5-triazin-2-yl)-4-methylmorpholinium chloride, CDI, EDCI-HOBt, EDCI-HATU, isobutyl chloroformate/NMM. The reaction may take place in various solvents, including DMAc, NMP, DCM, THF, 2-Me-THF, and in temperatures of about 0° C. to about 25° C.

Ester Hydrolysis of Compound (T-a) to Form Compound (H)

Crude Compound (T-a) was added with THF (200 mL) and MeOH (50 mL) to produce a solution. To this solution was added a solution of LiOH (10.9 g, 0.455 mol) in water (100 mL). After about 13 h, the reaction was concentrated by rotary evaporation and the resulting solution was washed with MTBE (3×50 mL). The aqueous phase was polish filtered through Celite and acidified to pH 2 with 6N HCl (100 mL). The mixture was extracted with dichloromethane (3×50 mL) and the combined organic phases were dried over $Na_2SO_4$, filtered and concentrated to produce Compound (H). $^1$H NMR (400 MHz, $d_6$-acetone) δ 6.50-6.19 (m, 1H), 4.80-4.53 (m, 1H), 4.48-4.29 (m, 1H), 4.27-3.94 (m, 1H), 3.75-3.38 (m, 3H), 2.44-1.52 (m, 9H), 1.32 (d, 3H), 0.96 (m, 6H).

Alternative reagents and reaction conditions to those disclosed above may also be employed. For example, various bases may be used, such as sodium hydroxide and potassium hydroxide. Various solvents, such as ethanol, isopropanol, DMF, DMAc, and NMP, may be used and temperatures may range from about 15° C. to about 25° C.

Example 2

Synthesis of Compound (J-a)

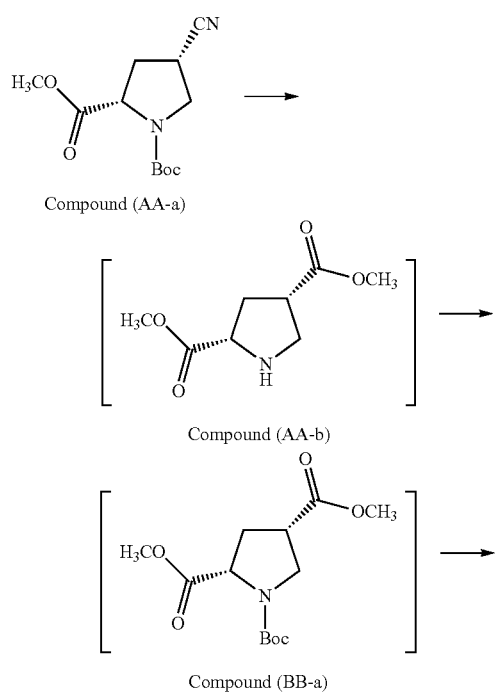

Compound (AA-a)

Compound (AA-b)

Compound (BB-a)

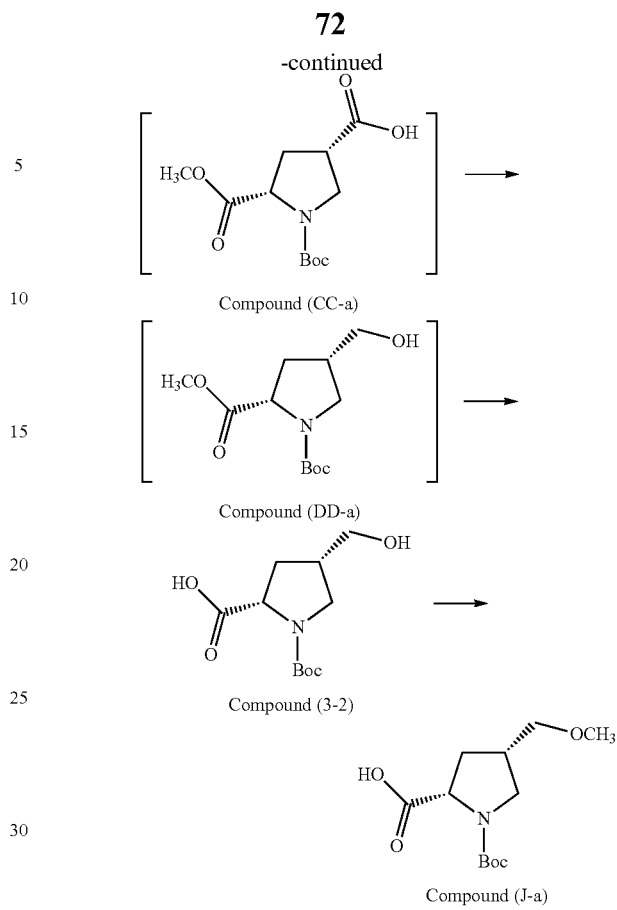

Compound (CC-a)

Compound (DD-a)

Compound (3-2)

Compound (J-a)

Hydrolysis and Boc-Protection: Conversion of Compound (AA-a) to Compound (BB-a)

Acetyl chloride (9.88 kg, 126 mol) was added slowly to cold methanol (6.73 kg). The resulting methanolic hydrogen chloride solution was added over about 1 hour to a solution of Compound (AA-a) (4.26 kg, 16.8 mol) in methanol (10.1 kg) while maintaining reaction temperature below 25° C. The reaction mixture was agitated at about 20° C. for about 1 hour, and then heated at reflux until reaction completion. The reaction mixture was concentrated under vacuum, cooled to about 15° C., and basified with sodium bicarbonate (8 wt. % aqueous solution, 34.9 L). Ethyl acetate (19.2 kg) and a solution of di-tert-butyl dicarbonate (3.66 kg, 16.8 mol) in ethyl acetate (7.7 kg) were added, the mixture was agitated for about 1 hour, and the layers were separated. The aqueous layer was extracted with ethyl acetate (12.8 kg) and the combined organic layers were concentrated under vacuum to provide Compound (BB-a). $^1$H NMR (400 MHz, $CDCl_3$) δ: 4.25 (dt, 1H), 3.84-3.52 (comp m, 8H), 3.01 (m, 1H), 2.45 (m, 1H), 2.28 (m, 1H), 1.38 (m, 9H).

Alternative reagents and reaction conditions to those disclosed above may also be employed. For example, various acids may be employed for hydrolysis, such as sulfuric acid, methanesulfonic acid, hydrobromic acid, camphorsulfonic acid, para-toluene sulfonic acid, and acetic acid, and alternative solvents may include dioxane, chloroform, benzene, and nitrobenzene. Alternatively, hydrolysis may be carried out with palladium in methanol. The reaction may take place at temperatures of about 20° C. to about 60° C.

Other boc-protection reagents, including but not limited to phenyl tert-butyl carbonate, tert-butyl N-succinimidyl carbonate, tert-butyl 4-formylphenyl carbonate, and tert-butyl carbonate azide, may be used. Alternative bases for use during the boc-protection step may include phosphate bases (such as potassium phosphate monobasic, potassium phosphate dibasic, potassium phosphate tribasic, sodium phosphate monobasic, sodium phosphate dibasic, and sodium phosphate tribasic), carbonate bases (such as potassium carbonate and cesium carbonate), hydroxide bases (such as potassium hydroxide, sodium hydroxide, lithium hydroxide), hydrides (such as sodium hydride), and organic bases (such as amines, including triethyl amine, diisopropyl amine, and diisopropyl ethyl amine). Various solvents, such as methyl tert-butyl ether, 2-methyltetrahydrofuran, tetrahydrofuran, isopropyl acetate, isobutyl acetate, methyl acetate, diethyl ether, isopropyl ether, dichloromethane, toluene, and N,N-dimethylformamide, may be employed. Temperatures may also range from about 0° C. to about 100° C.

Selective Ester Hydrolysis to Prepare Compound (CC-a)

Sodium hydroxide (1 N aqueous solution, 20.2 kg, 20.2 mol) was added over about 2 hours to a solution of Compound (BB-a) (4.32 kg, 15.04 mol) in tetrahydrofuran (22 kg) while maintaining reaction temperature below −1° C. Upon complete conversion, glacial acetic acid (0.5 kg) was added and the mixture was warmed to about 20° C. Methyl tert-butyl ether (13.6 kg) was added, the mixture was agitated, and the layers were separated. The organic layer was extracted twice with sodium bicarbonate (5% aqueous solution, 2×8.5 kg). The three aqueous layers were combined, methyl tert-butyl ether (14.5 kg) was added, and the mixture was acidified to pH 1 with hydrochloric acid (10% aqueous solution, 14.7 kg) while maintaining internal temperature below 15° C. The layers were separated and the aqueous layer was extracted with methyl tert-butyl ether (13.7 kg). The combined organic layers were washed twice with 25% brine (2×8.2 kg), and concentrated under vacuum to the minimum stirrable volume. 2-Methyltetrahydrofuran (28 kg) was charged to the residue and the mixture was concentrated under vacuum to the minimum stirrable volume. 2-Methyltetrahydrofuran (19.6 kg) was charged to the residue to provide Compound (CC-a) as a solution. $^1$H-NMR (400 MHz, acetone-d6) δ: 4.27 (t, 1H), 3.83-3.52 (comp m, 5H), 3.19 (m, 1H), 2.55 (m, 1H), 2.19 (m, 1H), 1.39 (m, 9H).

Alternative reagents and reaction conditions to those disclosed above may also be employed. For example, alternative bases may include lithium hydroxide, potassium hydroxide, barium hydroxide, and enzymes. Various solvents, such as methanol or Me-THF, may be employed, and temperatures may range from −20° C. to 20° C.

Reduction of Compound (CC-a) to Form Compound (DD-a)

Borane-dimethyl sulfide complex (2 M solution in tetrahydrofuran, 9.2 kg, 1.5 equiv.) was added over 90 minutes to a solution of Compound (CC-a) (3.8 kg) in 2-methyltetrahydrofuran (16.5 kg), while maintaining reaction temperature below 25° C. Upon complete conversion 10% aqueous ammonium acetate solution (19.6 kg) was added, the mixture was agitated for about 1 hour, and the layers were separated. The organic layer was diluted with methyl tert-butyl ether (7.2 kg) and washed with 10% aqueous ammonium acetate solution (11.4 kg). The combined aqueous layers were back-extracted with methyl tert-butyl ether (6.8 kg). The combined organic layers were washed with 20% brine solution (12.7 kg) and concentrated under vacuum to provide Compound (DD-a). $^1$H NMR (400 MHz, CDCl$_3$) δ: 4.28 (dt, 1H), 3.73 (s, 3H), 3.65 (m, 3H), 3.25 (dd, 1H), 2.42 (m, 2H), 1.79 (m, 1H), 1.63 (s, 1H), 1.44 (m, 9H).

Alternative reagents and reaction conditions to those disclosed above may also be employed. For example, other reduction reagents may be used. Non-limiting examples include sodium borohydride-boron trifluoride etherate mixture, diborane, borane-tetrahydrofuran complex, and various borane-amine complexes (such as borane-triethylamine, borane-diethylaniline and the like). Alternatively, activation reagents may also be used, and non-limiting examples of such activation reagents include thionyl chloride, oxalyl chloride, 1,1'-carbonyldiimidazole, 2-chloro-4,6-dimethoxy-1,3,5-triazine, cyanuric chloride, N,N'-dicyclohexylcarbodiimide, ethyl chloroformate, isobutyl chloroformate, N-hydroxysuccinimide, and 2,2,2-trifluoroethanol; reduction reagents may then include sodium sodium borohydride and lithium borohydride. Various solvents, such as methanol, ethanol, tetrahydrofuran, and water, may be used, and temperatures can range from about −20° C. to 40° C.

Synthesis of Compound (3-2) from Compound (DD-a)

An aqueous solution of sodium hydroxide (30% w/w, 103 g) is added to a solution of Compound (DD-a) (80.3 g) in methyl tert-butyl ether (320 mL) at about 10° C. The mixture is warmed to about 20° C. and agitated for about 2 hours. Water (80 mL) is added, the mixture is agitated, and then the layers are separated. Sodium chloride (20.8 g) is charged to the aqueous layer and agitated until dissolved. The solution is cooled to about 5° C. and then an aqueous solution of 15% w/w hydrochloric acid (195 g) is added over about 2 hours. The batch is seeded with Compound (3-2) (0.08 g) and the contents are agitated for about 1 hour. The resulting slurry is filtered and the isolated solids are washed with an aqueous solution of 10% w/w sodium chloride (240 mL) followed by water (40 mL). The wet solids are dried to provide Compound (3-2).

Synthesis of Compound (J-a) from Compound (3-2)

Methyl iodide (18.3 mL) is added to a solution of Compound (3-2) (48.0 g) in tetrahydrofuran (240 mL) and the mixture is cooled to about 10° C. Sodium tert-butoxide (45.0 g) is added over about 10 minutes and then the reaction mixture is warmed to about 20° C. and agitated for about an additional 3 hours. Methyl tert-butyl ether (125 mL) and water (125 mL) are then added. The biphasic mixture is agitated, the layers are separated, and the organic layer is extracted with water (125 mL). The aqueous layers are combined and sodium chloride (48.0 g) is added. Methyl tert-butyl ether (192 mL) is added and the temperature is adjusted to about 10° C. A solution of 15% w/w hydrochloric acid (60 g) is added over about 15 minutes. The mixture is agitated and the layers are separated. The organic layer is washed sequentially with a solution of 20% w/w sodium metabisulfite/10% w/w sodium chloride (48 mL) followed by 10% w/w sodium chloride (48 mL), then dried over magnesium sulfate and filtered. One third of the total organic filtrate was concentrated to remove the solvent and then isopropanol (38 mL) is added. The solution is concentrated to remove solvent and then isopropanol (7.5 mL) is added. The solution is adjusted to about 20° C. and water (12 mL) is added. The solution is seeded with Compound (J-a) (0.04 g) and agitated for about 30 minutes. Water (3 mL) is added and the mixture is agitated for about 1 hour. Water (33 mL) is added over about 2 hours and then the mixture is heated to about 35° C. over about 1.5 hours. The mixture is agitated at about 35° C. for about 2 hours and then cooled to about 0° C. over about 3.5 hours. The resulting slurry is filtered, washed with a mixture of 5:1 v/v water:isopropanol (7.5 mL), and dried to provide Compound (J-a). $^1$H NMR (400 MHz, acetone-d6) δ: 4.20 (dd, 1H), 3.61 (m, 1H), 3.35 (m, 2H), 3.26 (s, 3H), 3.10 (m, 1H), 2.45 (m, 2H), 1.73 (m, 1H), 1.39 (m, 9H).

Alternative Synthesis of Compound (J-a) from Compound (DD-a)

Methyl iodide (11.8 kg) was added to a solution of Compound (DD-a) (3.0 kg, 11.5 mol) in tetrahydrofuran (20 kg). Sodium hydroxide (20 wt. % aqueous solution, 9.3 kg) was added over about 1 hour while maintaining reaction temperature below about 15° C., and the mixture was diluted with methyl tert-butyl ether (8.8 kg) and water (3 kg). The mixture was agitated, the layers were separated, and the organic layer was extracted with water (6.2 kg). The combined aqueous layers were acidified to pH 1 with hydrochloric acid (10 wt. % aqueous solution, 34.0 kg) and extracted twice with methyl tert-butyl ether (2×9.7 kg). The combined organic layers were washed with sodium bisulfite (10 wt. % aqueous solution, 6 kg) and 10% brine (6 kg), and concentrated under vacuum. Toluene (18.6 kg) was added, and the solution was concentrated under vacuum. The residue was dissolved in toluene (5.4 kg), heptane (3.0 kg) was added, and the batch was seeded with Compound (J-a) (0.034 kg). Heptane (12.8 kg) was added over 30 minutes, and the resulting slurry was stirred at about 20° C. for about 2 hours. The precipitated product was filtered, washed with heptane (4.2 kg), and dried under vacuum at about 20° C. to provide Compound (J-a).

Alternative reagents and reaction conditions to those disclosed above may also be employed. For example, other reagents and additives may include dimethyl sulfate, methyl p-toluenesulfonate, methyl triflate, and methyl carbonate. Silver triflate may also be added. Various bases, such as potassium hydroxide, 2,6-lutidine, 2,6-di-tert-butyl-methyl pyridine, and potassium tert-butoxide, sodium tert-butoxide, lithium hydroxide, may also be employed. Alternative solvents include but are not limited to dichloromethane, acetonitrile, tetrahydrofuran, water, methanol, dimethyl sulfoxide, and toluene. The reaction may also proceed at temperatures ranging from about 0° C. to about 60° C. or about 15° C. Compound (J-a) may also be isolated in various forms, such as a dicyclohexylamine salt in toluene, isopropyl acetate, methyl tert-butyl ether, and 2-methyltetrahydrofuran; a dicyclohexylamine salt in toluene, isopropyl acetate, methyl tert-butyl ether, and 2-methyltetrahydrofuran; a sodium salt; potassium salt; or lithium salt.

Example 3

Alternative Synthesis of Compound (J-a)

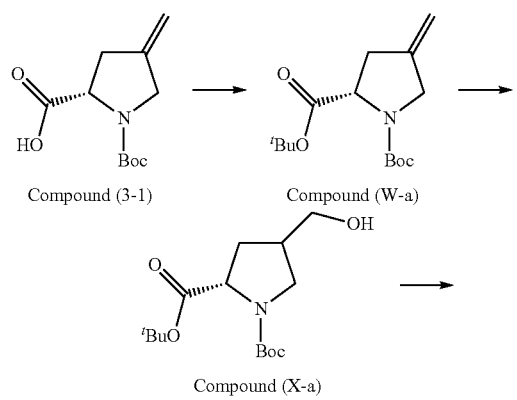

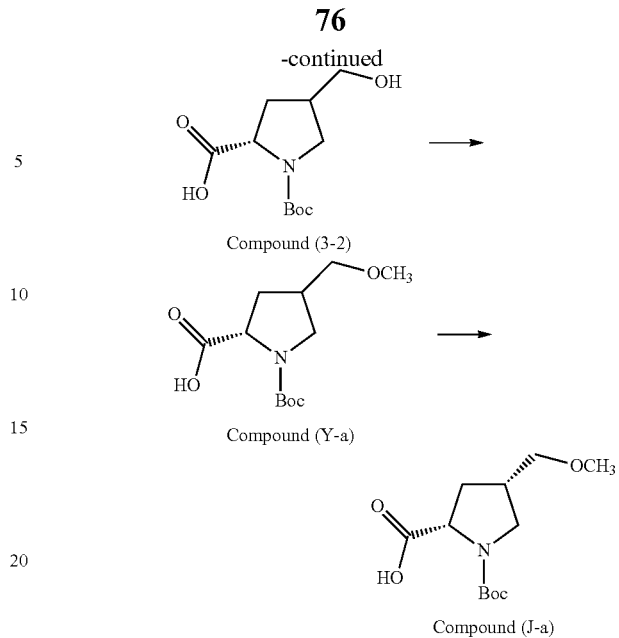

Esterification of Compound (3-1) to Form Compound (W-a)

A reactor is charged with Compound (3-1) (100 g, 0.440 mol, 1.0 equiv), 4,4-dimethylamino-pyridine (10.7 g, 0.088 mol, 0.2 equiv) and methyl tert-butyl ether (600 mL). To this solution is added di-tert-butyl dicarbonate (105 g, 0.484 mol, 1.1 equiv) over 2 hours. The resulting mixture is stirred at about 20° C. to about 30° C. for additional about 2 to about 3 hours until the reaction is complete and then washed successively with dilute hydrochloric acid (200 mL), dilute aqueous sodium hydroxide solution (200 mL) and brine (100 mL). The organic phase obtained after layer separation is dried over anhydrous sodium sulfate and concentrated by vacuum distillation to obtain Compound (W-a), which is used directly in the next step.

Alternative reagents and reaction conditions to those disclosed above may also be employed. For example, other boc-protection reagents, including but not limited to phenyl tert-butyl carbonate, tert-butyl N-succinimidyl carbonate, tert-butyl 4-formylphenyl carbonate, and tert-butyl carbonate azide, may be used. Various solvents, such as methyl tert-butyl ether, 2-methyltetrahydrofuran, tetrahydrofuran, isopropyl acetate, isobutyl acetate, methyl acetate, diethyl ether, isopropyl ether, dichloromethane, toluene, and N,N-dimethylformamide, may be employed. Temperatures may also range from about 0° C. to about 100° C.

Synthesis of Compound (X-a) from Compound (W-a)

(−)-Pinene (28.0 g, 205.6 mmol, 3 equiv) is added slowly to 100 mL of 1.0 M borane-dimethylsulfide (100 mmol, 1.5 equiv) solution in tetrahydrofuran while maintaining reaction temperature below about −20° C. The resulting mixture is warmed slowly to about 25° C. over about 2.5 hours and stirred for additional 2 hours. The mixture is then cooled to about −30° C. and a solution of 18.8 g of crude Compound (W-a) (66.4 mmol) in 18.8 mL of tetrahydrofuran is added slowly while maintain reaction temperature below about −20° C. The reaction mixture is then warmed to about 0° C. over 1 hour and stirred at this temperature for about 15 hours. Water is added slowly until gas evolution subsides, and then the reaction mixture is diluted with 40 mL of $Na_2PO_4$/NaOH solution (10 g dibasic sodium phosphate and 1 g sodium hydroxide dissolved in 40 mL of water). 35 mL of 30% hydrogen peroxide solution is added while maintaining reaction temperature below about 5° C. The reaction mixture is then warmed to about 25° C. and stirred at this temperature for additional 1 hour. Layers are separated and the aqueous layer is extracted with methyl tert-butyl ether (90 mL). The combined organic phase is washed successively with 20% aqueous sodium sulfite solution (100 mL) and brine (90 mL), dried over anhydrous sodium sulfate. The filtrate is concentrated under vacuum to obtain crude Compound (X-a), which is used directly in the next step.

Alternative reagents and reaction conditions to those disclosed above may also be employed. For example, additional hydroborating reagents, including but not limited to borane-THF complex, borane-amine complex, disiamylborane, monoisopinocamphenylborane, diethylborane, dimesitylborane and 9-BBN, may be used. Various solvents, such as methyl tert-butyl ether, 2-methyltetrahydrofuran, tetrahydrofuran, isopropyl acetate, isobutyl acetate, diethyl ether, isopropyl ether, toluene, and N,N-dimethylformamide may be employed. Temperatures may also range from about 0° C. to about 100° C.

Deprotection of Compound (X-a) to Form Compound (3-2)

Compound (X-a) (48 g) is mixed with 20% methanolic HCl (90 mL) and agitated at about 25° C. for about 15 hours. The mixture is then concentrated by vacuum distillation, mixed with methanol (50 mL), and concentrated again. The residue is mixed with water (100 mL) and methyl tert-butyl ether (50 mL). Layers are separated, and the organic phase is extracted with water (50 mL). The combined aqueous phase is treated with 15% aqueous sodium hydroxide to adjust pH to about 7-8. To this mixture is charged di-tert-butyl dicarbonate (21.7 g, 99.4 mmol, 1.5 equiv) followed by 15% aqueous sodium hydroxide (35.0 g). The mixture is agitated at about 25° C. for 3 hours, and then methyl tert-butyl ether (30 mL) is charged. The layers are separated and sodium chloride (30 g) is charged to the aqueous layer. The aqueous layer is treated with 10% aqueous hydrochloric acid to adjust to pH 2-3 and then extracted twice with ethyl acetate (100 mL and 50 mL). The organic layers are combined, and concentrated to dryness by vacuum distillation. The residue is redissolved in methyl-tert-butyl ether (30 mL) and then concentrated again. This operation is repeated twice to complete solvent replacement from ethyl acetate to methyl tert-butyl ether. The final solution in about 30 mL of methyl tert-butyl ether is stirred at ambient temperature for about 1 hour to obtain a slurry. The solids are isolated by filtration and dried to provide crude Compound (3-2).

Crude Compound (3-2) (11 g) is dissolved at about 45° C. in a mixture of methyl tert-butyl ether (30 mL) and methanol (10 mL). The solution is concentrated and solvent exchanged into methyl tert-butyl ether to cause precipitation of the product. The precipitated product is isolated bt filtration and dried to obtain purified Compound (3-2).

Alternative reagents and reaction conditions to those disclosed above may also be employed. For example, various acids may be employed for hydrolysis, such as sulfuric acid, methanesulfonic acid, hydrobromic acid, camphorsulfonic acid, para-toluene sulfonic acid, and acetic acid, and alternative solvents may include dioxane, chloroform, benzene, and nitrobenzene. Alternatively, hydrolysis may be carried out with palladium in methanol. The reaction may take place at temperatures of about 20° C. to about 60° C.

Other boc-protection reagents, including but not limited to phenyl tert-butyl carbonate, tert-butyl N-succinimidyl carbonate, tert-butyl 4-formylphenyl carbonate, and tert-butyl carbonate azide, also may be used. Alternative bases for use during the boc-protection step may include phosphate bases (such as potassium phosphate monobasic, potassium phosphate dibasic, potassium phosphate tribasic, sodium phosphate monobasic, sodium phosphate dibasic, and sodium phosphate tribasic), carbonate bases (such as potassium carbonate and cesium carbonate), hydroxide bases (such as potassium hydroxide, sodium hydroxide, lithium hydroxide), hydrides (such as sodium hydride), and organic bases (such as amines, including triethyl amine, diisopropyl amine, and diisopropyl ethyl amine).

Various solvents, such as methyl tert-butyl ether, 2-methyltetrahydrofuran, tetrahydrofuran, isopropyl acetate, isobutyl acetate, methyl acetate, diethyl ether, isopropyl ether, dichloromethane, toluene, and N,N-dimethylformamide, may be employed. Temperatures may also range from about 0° C. to about 100° C.

Methylation of Compound (3-2) to Form Compound (Y-a)

Compound (3-2) (7.0 g, 28.5 mmol) is dissolved in tetrahydrofuran (35 mL). The resulting solution is mixed with 50% aqueous sodium hydroxide (13.7 g, 171.3 mmol, 6.0 equiv) and then with methyl iodide (12.2 g, 86.0 mmol, 3.0 equiv). The mixture is agitated at about 25° C. for about 15 hours and then concentrated by vacuum distillation to remove most of the organic solvent. The concentrate is diluted with methyl tert-butyl ether (50 mL) and water (50 mL) and treated with 10% aqueous hydrochloric acid to adjust pH to 2-3. Layers are separated, the aqueous layer is extracted with methyl tert-butyl ether (25 mL). The organic layers are combined and then washed with brine (25 mL), and dried over anhydrous sodium sulfate. The filtered solution is concentrated by vacuum distillation to obtain crude Compound (Y-a).

To a solution of 15.2 g crude Compound (Y-a) (58.6 mmol, 1.0 equiv) in methyl tert-butyl ether (120 mL) is added dicyclohexylamine (9.0 g, 46.9 mmol, 0.85 equiv). The mixture is warmed to about 60° C. and agitated for about 3 hours. The resulting slurry is cooled slowly to about 20° C. over 2 hours, and then agitated for an additional 2 hours. The slurry is filtered and the filter cake rinsed with methyl tert-butyl ether (30 mL) to provide Compound (Y-a) as a dicyclohexylamine salt, which is a white solid.

Alternative reagents and reaction conditions to those disclosed above may also be employed. For example, other reagents and additives may include dimethyl sulfate, methyl p-toluenesulfonate, methyl triflate, and methyl carbonate. Silver triflate may also be added. Various bases, such as potassium hydroxide, 2,6-lutidine, 2,6-di-tert-butyl-methyl pyridine, and potassium tert-butoxide, sodium tert-butoxide, lithium hydroxide, may also be employed. Alternative solvents include but are not limited to dichloromethane, acetonitrile, tetrahydrofuran, water, methanol, dimethyl sulfoxide, and toluene. The reaction may also proceed at temperatures ranging from about 0° C. to about 60° C. or about 15° C. Compound (Y-a) may also be isolated in various forms, such as a sodium salt, potassium salt, or lithium salt.

Synthesis of Compound (J-a) from Compound (Y-a)

The dicyclohexylamine salt of Compound (Y-a) (14.6 g) is mixed with methyl tert-butyl ether (75 mL) and water (75 mL) and the pH adjusted to 10-11 with 15% aqueous sodium hydroxide. Layers are separated, and the organic phase is discarded. To the aqueous phase is added methyl tert-butyl ether (75 mL) and then the pH is adjusted to 2-3 by addition of 10% hydrochloric acid while maintaining temperature below 25° C. Layers are separated, and the aqueous phase is extracted with methyl tert-butyl ether (37.5 mL). The combined organic phase is washed with brine (37.5 mL) and then dried with anhydrous sodium sulfate. The mixture is filtered and the filtrate is concentrated to dryness by vacuum distillation. The residue is mixed with hexane (30 mL) and the resulting mixture is concentrated to dryness by vacuum distillation. The residue is mixed with hexane (75 mL) and dichloromethane (3.75 mL). The mixture is heated to about 60° C. and agitated for about 1 hour. The mixture is then cooled slowly to about 20° C. over about 2 hours and agitated for an additional 1 hour. The precipitated solids are isolated by filtration, rinsed with hexane (30 mL) and dried to obtain Compound (J-a).

Alternative reagents and reaction conditions to those disclosed above may also be employed. For example, alternative bases for use during salt break may include other hydroxide bases (such as potassium hydroxide and lithium hydroxide), phosphate bases (such as potassium phosphate tribasic, potassium phosphate dibasic, sodium phosphate dibasic, and sodium phosphate tribasic), and carbonate bases (such as potassium carbonate, sodium carbonate and cesium carbonate). Various solvents, such as methyl tert-butyl ether, 2-methyltetrahydrofuran, tetrahydrofuran, isopropyl acetate, isobutyl acetate, methyl acetate, diethyl ether, isopropyl ether, dichloromethane, and toluene may be employed.

Example 4

Alternative Synthesis of Compound (J-a)

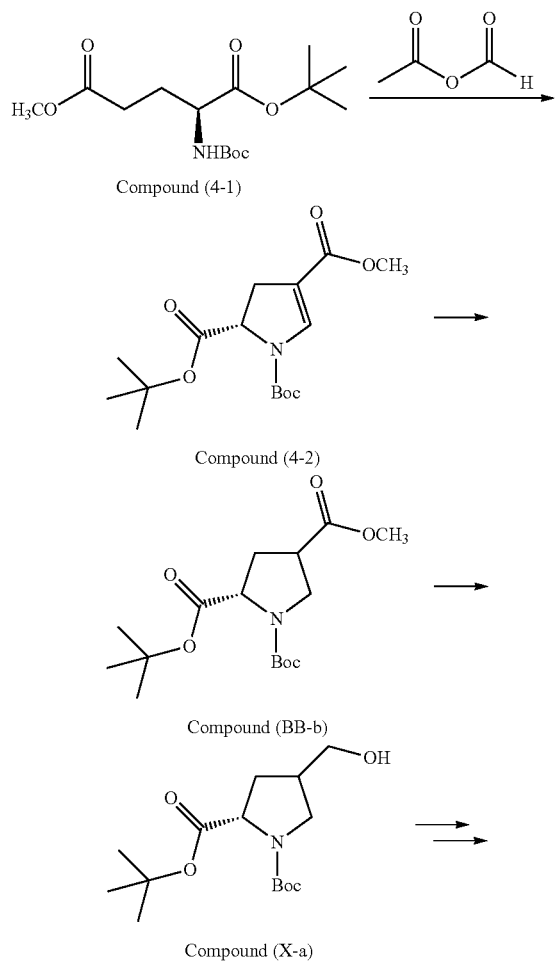

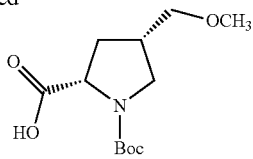

Compound (J-a)

Cyclization of Compound (4-1) to form Compound (4-2)

A mixture of tetrahydrofuran (152 kg, 171 L) and sodium formate (29.8 kg, 425 mol, 3.8 equiv) is cooled to about 0° C. to about 5° C. and agitated for about 1 hour. To this mixture is slowly charged acetyl chloride (26.7 kg, 340 mol, 3.0 equiv) while maintaining the internal temperature at about 0° C. to about 5° C. The mixture is agitated for about 30 minutes, then warmed to about 25° C. and agitated for an additional 14 to 16 hours until the reaction is complete.

A second reactor is charged with tetrahydrofuran (323 kg, 363 L) and lithium amide (12.5 kg, 544 mol, 4.8 equiv). The mixture is heated to about 50° C. to about 60° C. and hexamethyldisilazane (96.9 kg, 600 mol, 5.3 equiv) is added over 3 to 4 hours. The mixture is agitated for an additional 1 to 2 hours, adjusted to about 65° C. to about 75° C., and agitated for 10 to 15 hours. The resulting solution of lithium hexamethyldisilazide is cooled to about −75° C. to −70° C. A solution of Compound (4-1) (36 kg, 113 mol) in tetrahydrofuran (93 L) is added over 1 to 2 hours while maintaining the internal temperature at about −75° C. to −70° C. The solution of acetic formic anhydride is then added to the cold reaction mixture. The resulting reaction mixture is warmed slowly to about −65° C. to about −60° C. over 1 to 2 hours, and then a solution acetic acid (55 kg, 52 L, 916 mol, 8.1 equiv) in tetrahydrofuran (55 kg, 62 L) is charged while maintaining the internal temperature below about −35° C. The temperature of the reaction mixture is adjusted to about −20° C. to about −10° C., and water (183 L) is charged while maintaining the internal temperature below about 10° C. The layers are separated and the aqueous layer is extracted with methyl tert-butyl ether (183 kg, 247 L). The organic layers are combined and washed with brine (209 kg, 175 L), followed by water (190 L). The layers are separated and the organic layer is dried with anhydrous sodium sulfate (30 kg) for 1 hour. The slurry is filtered and the filter is rinsed with dichloromethane (60 kg, 45 L). The filtrate is concentrated by vacuum distillation at 40-50° C. The reactor is charged with dichloromethane (100 kg, 75 L) and the mixture is concentrated by vacuum distillation at 40-50° C. A second portion of dichloromethane (100 kg, 75 L) is charged and the mixture is concentrated by vacuum distillation at 40-50° C. The residue is dissolved in dichloromethane (256 kg, 192 L), cooled to about 0° C. to about 5° C. and trifluoroacetic acid (12.9 kg, 8.7 L, 113 mol, 1 equiv) is added to the mixture while maintaining the internal temperature below 5° C. The mixture is agitated for about 30 minutes, then warmed to about 20° C. to about 25° C. and agitated for an additional 6 to 10 hours. The internal temperature is adjusted to 10° C. to about 20° C. and 10% aqueous sodium carbonate (150 kg, 142 mol, 1.3 equiv) is slowly charged to adjust to pH 6 to 7. The mixture is adjusted to about 30° C. to about 40° C. and distilled under vacuum to remove approximately 160 kg dichloromethane (120 L). The mixture is then adjusted to about 20° C. to about 35° C. and extracted with methyl tert-butyl ether (180 kg, 243 L). The layers are separated and the aqueous layer is extracted with a second portion of methyl tert-butyl ether (180 kg, 243 L). The organic layers are combined and washed with 10% aqueous sodium chloride solution (120 kg, 112 L). The layers are separated and the organic layer is dried with anhydrous sodium sulfate (50 kg). The slurry is passed through silica gel (15 kg), eluting with methyl tert-butyl ether (60 kg, 81 L). The eluent is concentrated to an oil by vacuum distillation at about 35° C. to about 45° C. and the residue is dissolved in methanol (40 kg, 51 L) and used directly in the next step.

Alternative reagents and reaction conditions to those disclosed above may also be employed. For example, alternative bases may include, but are not limited to, lithium diisopropylamide, sodium bis(trimethylsilyl)amide, potassium bis(trimethylsilyl)amide, and the like. Alternative formylation agents, in lieu of acetic formic anhydride, may be phenyl formate, 2,2,2-trifluoroethyl formate, and the like. Various solvents may be used, including but not limited to methyltetrahydrofuran, cyclopentyl methyl ether, and the like.

Hydrogenation of Compound (4-2) to Form Compound (BB-b)

The solution of Compound (4-2) in methanol is charged into a hydrogenation reactor and mixed with 10% palladium on carbon (4.5 kg, 4.2 mol, 0.04 equiv), methanol (120 kg, 152 L), and acetic acid (0.9 kg, 15.0 mol, 0.1 equiv). The reactor is pressurized with hydrogen gas and the mixture is agitated at about 20° C. to about 30° C. until the reaction is deemed complete by TLC analysis (e.g. for about 12 to 16 hours). The mixture is then filtered to remove solids and the filtrate is concentrated by vacuum distillation at 30° C. to about 40° C. to obtain crude Compound (BB-b). The residue is dissolved in tetrahydrofuran (30 kg, 34 L) and used directly in the next step.

Alternative reagents and reaction conditions to those disclosed above may also be employed. For example, other catalysts, such as platinum dioxide, palladium acetate and charcoal mixture, bis(triphenylphosphine)ruthenium(II)dichloride, and the like, may be employed. Alternative reducing agents may be ammonium formate, formic acid, triethylsilane, and the like. Alternative solvents, include but are not limited to, ethanol, ethyl acetate, isopropyl acetate, methyltetrahydrofuran, tetrahydrofuran, and water. The reaction may also proceed at temperatures ranging from about 0° C. to about 60° C.

Reduction of Compound (BB-b) to Form Compound (X-a)

Crude Compound (BB-b) is mixed with tetrahydrofuran (90 kg, 101 L) and water (30 L). The temperature of the mixture is adjusted to about 20° C. to about 25° C., and sodium borohydride (14.4 kg, 381 mol, 4.0 equiv) is added. The resulting mixture is agitated at about 20 to about 25° C. until the reaction is deemed complete by TLC analysis (e.g. for about 2 to 4 hours). The mixture is then cooled to about 0° C. to about 10° C., and 12% aqueous hydrochloric acid (30 kg, 28 L) is charged to adjust pH to 6-7. The mixture is filtered through Celite (10 kg) and the filter is rinsed with methyl tert-butyl ether (30 kg, 41 L). The filtrate is allowed to settle to allow layer separation. Layers are separated and the aqueous layer is extracted twice with methyl tert-butyl ether (150 kg, 203 L). The organic layers are combined and washed with brine (50 kg, 42 L) and concentrated by vacuum distillation at about 35° C. to about 45° C. to an oil. To the residue is mixed with methanol (60 kg, 76 L), and the resulting solution is concentrated by vacuum distillation at about 35-45° C. to obtain crude Compound (X-a) which is used directly in the next step.

Alternative reagents and reaction conditions to those disclosed above may also be employed. For example, other reduction reagents may be used. Non-limiting examples include lithium borohydride, lithium aluminum hydride, diborane, 9-BBN, borane-tetrahydrofuran complex, and the like. Various solvents, such as methanol, ethanol, methyltetrahydrofuran, monoglyme, diglyme, and the like, may be used. The reaction may also take place at temperatures that range from about −20° C. to about 40° C.

Syntheses of Compound (I-a)

The synthesis of Compound (I-a) from Compound (X-a) can be carried out as described in Example 3.

Example 5

Synthesis of Compound (I-a)

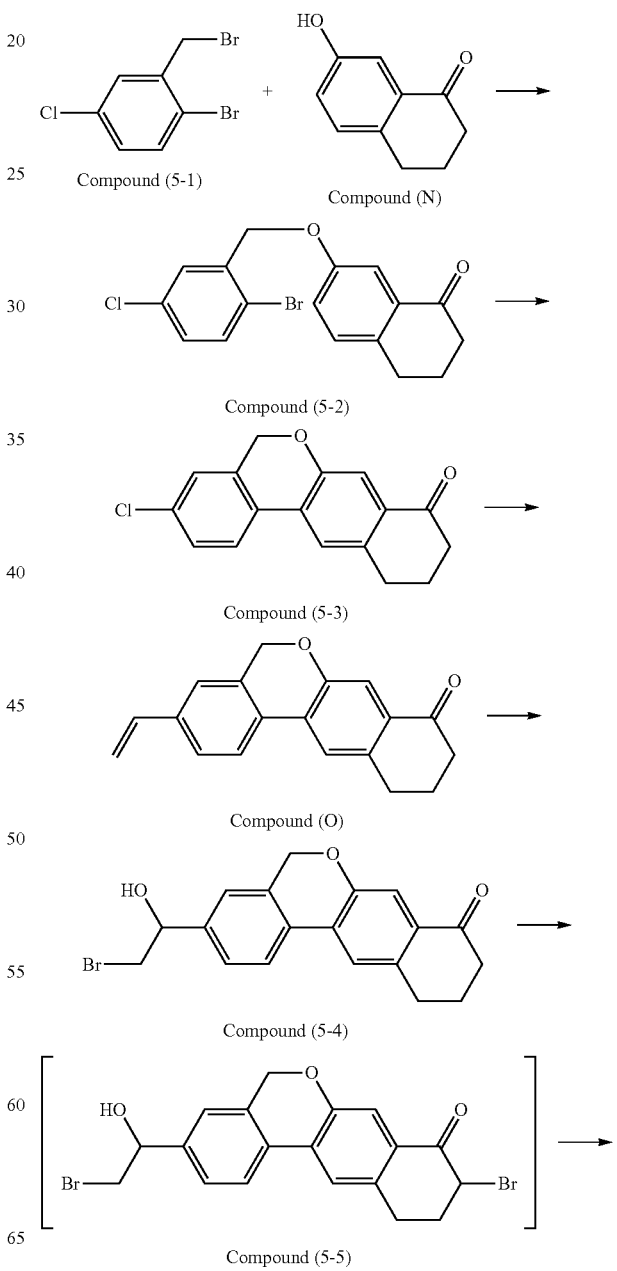

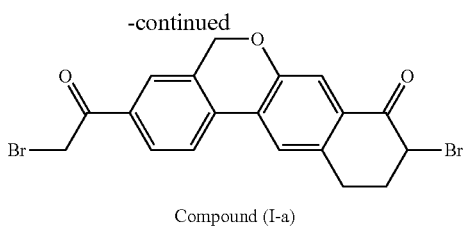

Compound (I-a)

Alkylation of Compound (5-1) with Compound (N) to Compound (5-2)

To a mixture of 7-hydroxy-3,4-dihydronaphthalen-1(2H)-one (Compound (N)) (1.0 g) and 1-bromo-2-(bromomethyl)-4-chlorobenzene (1.75 g) (Compound (5-1)) and N,N-dimethylacetamide (5 mL) at ambient temperature was added potassium carbonate (1.28 g). After complete conversion, the mixture was diluted with water (10 mL) and the mixture was filtered. The filter cake was washed with water and the isolated solids dried under reduced pressure at 50° C. to afford 7-(2-bromo-5-chlorobenzyloxy)-3,4-dihydronaphthalen-1(2H)-one (Compound (5-2)). HRMS (ESI+ MS/MS) Calculated for $C_{17}H_{15}BrClO_2$ m/z (M+H): 364.9944, and 366.9923. Found: 364.9947, and 366.9948. $^1$H NMR (400 MHz, CDCl$_3$) δ 7.62 (d, J=2.0 Hz, 1H), 7.56 (s, 1H), 7.50 (d, J=8.5 Hz, 1H), 7.24-7.11 (m, 3H), 5.10 (s, 2H), 2.98-2.86 (m, 2H), 2.70-2.60 (m, 2H), 2.21-2.06 (m, 2H).

Alternative reagents and reaction conditions to those disclosed above may also be employed. For example, alternative electrophiles include 1-bromo-4-chloro-2-(chloromethyl)benzene, 1-bromo-4-chloro-2-(fluoromethyl)benzene, 1-bromo-4-chloro-2-(iodomethyl)benzene, 2-bromo-5-chlorobenzyl 4-methylbenzenesulfonate, 2-bromo-5-chlorobenzyl benzenesulfonate, (2-bromo-5-chlorophenyl)methanol, 2-bromo-5-chlorobenzyl methanesulfonate, 2-bromo-5-chlorobenzyl trifluoromethanesulfonate, and 2-bromo-5-chlorobenzyl 4-nitrobenzenesulfonate.

Additionally, a variety of bases may be used, including lithium carbonate, sodium carbonate, cesium carbonate, beryllium carbonate, magnesium carbonate, calcium carbonate, strontium carbonate, barium carbonate, lithium hydroxide, sodium hydroxide, potassium hydroxide, cesium hydroxide, beryllium hydroxide, magnesium hydroxide, calcium hydroxide, strontium hydroxide, barium hydroxide, lithium bicarbonate, sodium bicarbonate, potassium bicarbonate, cesium bicarbonate, beryllium bicarbonate, magnesium bicarbonate, calcium bicarbonate, strontium bicarbonate, barium bicarbonate, lithium hydride, sodium hydride, potassium hydride, magnesium hydride, calcium hydride, lithium tert-butoxide, sodium tert-butoxide, potassium tert-butoxide, cesium tert-butoxide, beryllium tert-butoxide, magnesium tert-butoxide, calcium tert-butoxide, strontium tert-butoxide, barium tert-butoxide, aluminum tert-butoxide, titanium tert-butoxide, 2,2,6,6-tetramethylpiperidine, 2,6-ditertbutylpyridine, 4-methyl-2,6-ditertbutylpyridine, trilithium phosphate, trisodium phosphate, tripotassium phosphate, tricesium phosphate, beryllium phosphate, magnesium phosphate, calcium phosphate, strontium phosphate, dilithium hydrogenphosphate, disodium hydorgenphosphate, dipotassium hydrogenphosphate, dicesium hydrogenphosphate, lithium dihydrogenphosphate, sodium dihydrogenphosphate, potassium dihydrogenphosphate, and cesium dihydrogenphosphate.

Various solvents may be employed. Non-limiting examples may be N,N-dimethylformamide, N,N-dimethylacetamide, N-methylpyrolidine, 2-methyltetrahydrofuran, tetrahydrofuran, isopropyl acetate, ethyl acetate, tert-butyl methyl ether, cyclopentyl methyl ether, diethylether, acetone, methylethyl ketone, methylisobutylketone, diisopropyl ether, 1,4-dioxane, 1,2-dimethoxyethane, chloroform, acetonitrile, toluene, dichloromethane, and nitromethane.

The reaction may take place at temperatures that range from about 35° C. or about 0° C. to about 40° C. and at time lengths of about 1 hour to about 48 hours or about 24 hours.

Cyclization of Compound (5-2) to Compound (5-3)

A mixture of 7-(2-bromo-5-chlorobenzyloxy)-3,4-dihydronaphthalen-1(2H)-one (1.00 g) (Compound (5-2)), potassium carbonate (1.19 g), triphenylphosphine (38.3 mg), palladium (II) acetate (32.4 mg), pivalic acid (86.4 mg) and N,N-dimethylacetamide (5 mL) was heated to about 60° C. After complete consumption of the starting material, water (20 mL) was added. The mixture was filtered, and the filter cake washed with water (2×20 mL) and then with hexane (2×5 mL). The filter cake was dried under reduced pressure at ambient temperature to provide 3-chloro-10,11-dihydro-5H-dibenzo[c,g]chromen-8(9H)-one (Compound (5-3)). $^1$H NMR (400 MHz, CDCl$_3$) δ 77.65 (d, J=8.3 Hz, 1H), 7.61 (s, 1H), 7.54 (s, 1H), 7.35 (d, J=8.3 Hz, 1H), 7.17 (s, 1H), 5.06 (s, 2H), 3.02-2.86 (m, 2H), 2.73-2.53 (m, 2H), 2.26-2.00 (m, 2H).

Alternative reagents and reaction conditions to those disclosed above may also be employed. For example, alternative cyclization starting material in lieu of 7-(2-bromo-5-chlorobenzyloxy)-3,4-dihydronaphthalen-1(2H)-one can include 7-(2,5-dichlorobenzyloxy)-3,4-dihydronaphthalen-1(2H)-one, 7-(5-chloro-2-iodobenzyloxy)-3,4-dihydronaphthalen-1(2H)-one, 4-chloro-2-((8-oxo-5,6,7,8-tetrahydronaphthalen-2-yloxy)methyl)phenyl trifluoromethanesulfonate, 7-(5-bromo-2-chlorobenzyloxy)-3,4-dihydronaphthalen-1(2H)-one, 7-(2,5-dibromobenzyloxy)-3,4-dihydronaphthalen-1(2H)-one, 7-(5-bromo-2-iodobenzyloxy)-3,4-dihydronaphthalen-1(2H)-one, and 4-bromo-2-((8-oxo-5,6,7,8-tetrahydronaphthalen-2-yloxy)methyl)phenyl trifluoromethanesulfonate. Other starting materials can include Compound (5-6):

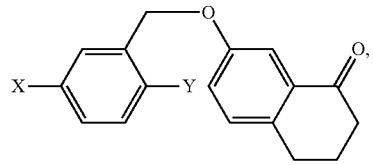

wherein X may be —Cl, —Br, —I, —OH, $R^bCO_2$—, $R^bSO_2$—, and $HSO_2$—. Y may be —Cl, —Br, —I, —OH, $R^bCO_2$—, $R^bSO_2$—, and $HSO_2$—. $R^b$ may be DO—, MeO—, EtO—, PrO—, iPrO— BuO—, PhO—, toluyl-O—, 4-NO$_2$PhO—, CF$_3$CH$_2$O—, CF$_3$O—, CF$_2$HO—, CFHO—, alkoxy, and Aryl-O—.

The metal component of the catalyst can vary. Non-limiting examples include palladium(II) trifluoroacetate, palladium(II) acetylacetonate, allylpalladium(II) chloride dimer, palladium (II) acetate, palladium (II) pivalate, palladium (II) chloride, palladium (II) bromide, tris(dibenzylideneacetone)dipalladium, bis(dibenzylideneacetone)palladium, bis(acetonitrile)dichloropalladium(II), tris(dibenzylideneacetone)dipalladium(0)-chloroform adduct, tetrakis(triphenylphosphine)palladium(0), dichlorobis(tricyclohexylphosphine)palladium(II), bis(triphenylphosphine)palladium(II) dichloride, dichlorobis(tri-o-tolylphosphine)

palladium(II), bis(di-tert-butyl(4-dimethylaminophenyl) phosphine)dichloropalladium(II), [1,1'-bis (diphenylphosphino)ferrocene]dichloropalladium(II), [1,1'-bis(diphenylphosphino)ferrocene]dichloropalladium(II) complex with dichloromethane, [1,1'-bis(di-tert-butylphosphino)ferrocene]dichloropalladium(II), tetrakis(acetonitrile) palladium(II) tetrafluoroborate, (SPhos) palladium(II) phenethylamine chloride, (XPhos) palladium(II) phenethylamine chloride, (RuPhos) palladium(II) phenethylamine chloride, (t-BuXPhos) palladium(II) phenethylamine chloride, and (BrettPhos) palladium(II) phenethylamine chloride.

The ligand component of the catalyst may be any ligands known in the art. For example, the ligand component may be tri-tert-butylphosphine, tri-tert-butylphosphine hydro tetrafluoroborate, methyl-di-tert-butylphosphine, methyl-di-tert-butylphosphine hydro tetrafluoroborate, 4,5-bis(diphenylphosphino)-9,9-dimethylxanthene, tri(p-tolyl)phosphine, tri-(2-furyl)phosphine, 4-(dimethylamino)phenyldiphenylphosphine, tri(4-fluorophenyl)phosphine, tri(4-trifluoromethylphenyl)phosphine, tri(4-methoxyphenyl)phosphine, tri (3-methylphenyl)phosphine, tri(2-methylphenyl)phosphine, tri(cyclohexyl)phosphine, Tri(2-furanyl)phosphine, 1,1'-bis (diphenylphosphino) ferrocene, 1,1'-bis(dicyclohexylphosphino) ferrocene, 1,1'-bis(ditertbutylphosphino) ferrocene, 1,3-bis-(2,6-diisopropylphenyl)imidazolinium chloride, 1,3-bis(2,4,6-trimethylphenyl)imidazolinium chloride, 1,3-diisopropylimidazolium tetrafluoroborate, 1,3-bis(1-adamantyl)imidazolium tetrafluoroborate, 2-(dicyclohexylphosphino)biphenyl, 2-dicyclohexylphosphino-2'-(N,N-dimethylamino)biphenyl, 2-dicyclohexylphosphino-2',4',6'-triisopropylbiphenyl, 2-dicyclohexylphosphino-2',6'-dimethoxybiphenyl, 2-dicyclohexylphosphino-2'-methylbiphenyl, 2-dicyclohexylphosphino-2',6'-diisopropoxybiphenyl, 2-(dicyclohexylphosphino)3,6-dimethoxy-2',4',6'-triisopropyl-1,1'-biphenyl, sodium 2'-dicyclohexylphosphino-2,6-dimethoxy-1,1'-biphenyl-3-sulfonate hydrate, 2-diphenylphosphino-2'-(N, N-dimethylamino)biphenyl, 2-di-tert-butylphosphino-2',4', 6'-triisopropylbiphenyl, (2-biphenyl)di-tert-butylphosphine, 2-di-tert-butylphosphino-3,4,5,6-tetramethyl-2',4',6'-triisopropyl-1,1'-biphenyl, 2-di-tert-butylphosphino-2'-methylbiphenyl, 2-(di-tert-butylphosphino)-2',4',6'-triisopropyl-3,6-dimethoxy-1,1'-biphenyl, 2-di-tert-butylphosphino-2'-(N,N-dimethylamino)biphenyl, 2-{Bis[3,5-bis(trifluoromethyl) phenyl]phosphino}-3,6-dimethoxy-2',4',6'-triisopropyl-1,1'-biphenyl, and the like.

Alternative acids and bases may be employed. Examples of acids may be propanoic acid, butyric acid, pentanoic acid, isobutyric acid, tert-butylcarboxylic acid, adamantylcarboxylic acid, and trifluoroacetic acid. Examples of bases may be lithium carbonate, sodium carbonate, cesium carbonate, beryllium carbonate, magnesium carbonate, calcium carbonate, strontium carbonate, barium carbonate, lithium hydroxide, sodium hydroxide, potassium hydroxide, cesium hydroxide, beryllium hydroxide, magnesium hydroxide, calcium hydroxide, strontium hydroxide, barium hydroxide, lithium bicarbonate, sodium bicarbonate, potassium bicarbonate, cesium bicarbonate, beryllium bicarbonate, magnesium bicarbonate, calcium bicarbonate, strontium bicarbonate, barium bicarbonate, lithium hydride, sodium hydride, potassium hydride, magnesium hydride, calcium hydride, lithium tert-butoxide, sodium tert-butoxide, potassium tert-butoxide, cesium tert-butoxide, beryllium tert-butoxide, magnesium tert-butoxide, calcium tert-butoxide, strontium tert-butoxide, barium tert-butoxide, aluminum tert-butoxide, titanium tert-butoxide, 2,2,6,6-tetramethylpiperidine, 2,6-ditertbutylpyridine, 4-methyl-2,6-ditertbutylpyridine, tri-lithium phosphate, trisodium phosphate, tripotassium phosphate, tricesium phosphate, beryllium phosphate, magnesium phosphate, calcium phosphate, strontium phosphate, dilithium hydrogenphosphate, disodium hydrogenphosphate, dipotassium hydrogenphosphate, dicesium hydrogenphosphate, lithium dihydrogenphosphate, sodium dihydrogenphosphate, potassium dihydrogenphosphate, cesium dihydrogenphosphate, lithium tert-butylcarboxylate, sodium tert-butylcarboxylate, potassium tert-butylcarboxylate, cesium tert-butylcarboxylate, lithium acetate, sodium acetate, potassium acetate, cesium acetate, lithium propanoate, sodium propanoate, potassium propanoate, cesium propanoate, lithium isobutyrate, sodium isobutyrate, potassium isobutyrate, cesium isobutyrate, lithium adamantylcarboxylate, sodium adamantylcarboxylate, potassium adamantylcarboxylate, cesium adamantylcarboxylate, lithium trifluoroaceate, sodium trifluoroaceate, potassium trifluoroaceate, and cesium trifluoroaceate.

Exemplary solvents can include N,N-dimethylformamide, N,N-dimethylacetamide, N-methylpyrolidine, 2-methyltetrahydrofuran, tetrahydrofuran, isopropyl acetate, ethyl acetate, tert-butyl methyl ether, cyclopentyl methyl ether, diethylether, acetone, methylethyl ketone, methylisobutylketone, diisopropyl ether, 1,4-dioxane, 1,2-dimethoxyethane, chloroform, acetonitrile, toluene, dichloromethane, dimethylsulfoxide, and diisopropylether.

Alternative palladium scavengers may be employed, such as N-acetyl cysteine, activated charcoal, charcoal, ethylenediaminetetraacetic acid, 1,2-ethylenediamine, 1,2-diaminopropane, diethylenetriamine, triethylenetetramine, and tris (2-aminoethyl)amine.

The reaction can take place at temperatures ranging from about 60° C. to about 70° C. or about 20° C. to about 100° C., and at time length of about 5 hours to 6 hours of about 1 hour to about 48 hours.

Suzuki Reaction of Compound (5-3) to Compound (O)

3-Chloro-10,11-dihydro-5H-dibenzo[c,g]chromen-8 (9H)-one (5.00 g) (Compound (5-3)) was combined with palladium (II) acetate (0.20 g), 2-dicyclohexylphosphino-2', 6'-dimethoxybiphenyl (0.72 g) 2-methyltetrahydrofuran (50 mL). A solution of potassium hydroxide (3.94 g) and water (29 mL) was added followed by potassium vinyltrifluoroborate (3.53 g). The mixture was heated to about 70° C. After complete conversion, the temperature was adjusted to about 50° C. and N-acetyl cysteine (0.72 g) was added followed by celite (2.5 g). After 3 h, the mixture was filtered and the organic phase was washed with a 5% aqueous potassium hydroxide solution (15 mL) and 1M aqueous hydrochloric acid (1×75 mL and 1×50 mL). The organic phase was concentrated under reduced pressure and the temperature adjusted to about 50° C. Heptane (10 mL) was added, the temperature adjusted to about 23° C. and the mixture was filtered. The filter cake was washed with heptane (5 mL) and dried under reduced pressure at about 40° C. to provide 3-vinyl-10,11-dihydro-5H-dibenzo[c,g]chromen-8(9H)-one (Compound (O)). HRMS (ESI$^+$ MS/MS) Calculated for $C_{19}H_{17}O_2$ m/z (M+H): 277.1229; Found: 277.1238; $^1$H NMR (400 MHz, CDCl$_3$) δ 7.69 (d, J=8.0 Hz, 1H), 7.62 (s, 1H), 7.58 (s, 1H), 7.43 (d, J=8.0 Hz, 1H), 7.21 (s, 1H), 6.72 (dd, J=17.5, 10.9 Hz, 1H), 5.81 (d, J=17.6 Hz, 1H), 5.32 (d, J=10.8 Hz, 1H), 5.11 (s, 2H), 3.03-2.89 (m, 2H), 2.70-2.58 (m, 2H), 2.21-2.06 (m, 2H).

Alternative reagents and reaction conditions to those disclosed above may also be employed. For example, alternative starting materials may include 3-bromo-10,11-dihydro-5H-dibenzo[c,g]chromen-8(9H)-one, 3-iodo-10,11-dihydro-5H-dibenzo[c,g]chromen-8(9H)-one, 8-oxo-8,9,10, 11-tetrahydro-5H-dibenzo[c,g]chromen-3-yl trifluoromethanesulfonate, 8-oxo-8,9,10,11-tetrahydro-5H-dibenzo[c,g]chromen-3-yl benzenesulfonate, 8-oxo-8,9,10,11-tetrahydro-5H-dibenzo[c,g]chromen-3-yl 4-methylbenzenesulfonate, 8-oxo-8,9,10,11-tetrahydro-5H-dibenzo[c,g]chromen-3-yl 4-fluorobenzenesulfonate, 8-oxo-8,9,10,11-tetrahydro-5H-dibenzo[c,g]chromen-3-yl 4-(trifluoromethyl)benzenesulfonate, 8-oxo-8,9,10,11-tetrahydro-5H-dibenzo[c,g]chromene-3-carboxylic acid, lithium 8-oxo-8,9,10,11-tetrahydro-5H-dibenzo[c,g]chromene-3-carboxylate, sodium 8-oxo-8,9,10,11-tetrahydro-5H-dibenzo[c,g]chromene-3-carboxylate, potassium 8-oxo-8,9,10,11-tetrahydro-5H-dibenzo[c,g]chromene-3-carboxylate, cesium 8-oxo-8,9,10,11-tetrahydro-5H-dibenzo[c,g]chromene-3-carboxylate, methyl 8-oxo-8,9,10,11-tetrahydro-5H-dibenzo[c,g]chromene-3-carboxylate, ethyl 8-oxo-8,9,10,11-tetrahydro-5H-dibenzo[c,g]chromene-3-carboxylate, propyl 8-oxo-8,9,10,11-tetrahydro-5H-dibenzo[c,g]chromene-3-carboxylate, isopropyl 8-oxo-8,9,10,11-tetrahydro-5H-dibenzo[c,g]chromene-3-carboxylate, butyl 8-oxo-8,9,10,11-tetrahydro-5H-dibenzo[c,g]chromene-3-carboxylate, isobutyl 8-oxo-8,9,10,11-tetrahydro-5H-dibenzo[c,g]chromene-3-carboxylate, 2,2,2-trifluoroethyl 8-oxo-8,9,10,11-tetrahydro-5H-dibenzo[c,g]chromene-3-carboxylate, phenyl 8-oxo-8,9,10,11-tetrahydro-5H-dibenzo[c,g]chromene-3-carboxylate, p-tolyl 8-oxo-8,9,10,11-tetrahydro-5H-dibenzo[c,g]chromene-3-carboxylate, 4-nitrophenyl 8-oxo-8,9,10,11-tetrahydro-5H-dibenzo[c,g]chromene-3-carboxylate, 4-fluorophenyl 8-oxo-8,9,10,11-tetrahydro-5H-dibenzo[c,g]chromene-3-carboxylate, 4-(trifluoromethyl)phenyl 8-oxo-8,9,10,11-tetrahydro-5H-dibenzo[c,g]chromene-3-carboxylate, 4-methoxyphenyl 8-oxo-8,9,10,11-tetrahydro-5H-dibenzo[c,g]chromene-3-carboxylate, trifluoromethyl 8-oxo-8,9,10,11-tetrahydro-5H-dibenzo[c,g]chromene-3-carboxylate, difluoromethyl 8-oxo-8,9,10,11-tetrahydro-5H-dibenzo[c,g]chromene-3-carboxylate, and fluoromethyl 8-oxo-8,9,10,11-tetrahydro-5H-dibenzo[c,g]chromene-3-carboxylate. Additional alternative starting material can include Compound (5-7), Compound (5-8), Compound (5-8), and Compound (5-10):

Compound (5-7)

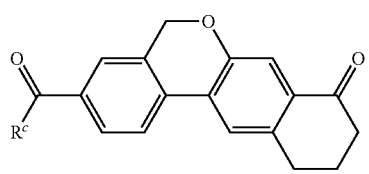

Compound (5-8)

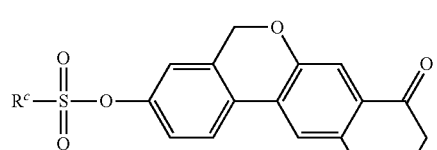

Compound (5-9)

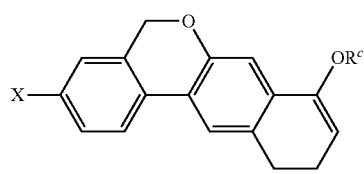

Compound (5-10)

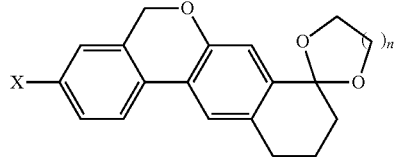

wherein $R^c$ may be alkoxy, aryloxy, heteroaryloxy, and X may be halo, $-OSO_2R^h$, and wherein $R^h$ may be alkyl, haloalkyl, aryl or substituted aryl. In some embodiments, the substituted aryl may be an aryl having one or more substituents, such as alkyl, alkoxy, hydroxyl, nitro, halogen, and others as discussed above.

Alternative vinyl components may also be employed. Non-limiting examples of such components can include compounds of the following structures:

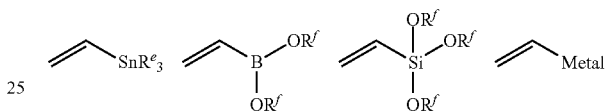

wherein $R^e$ can include alkyl or ethylene, $R^f$ can include alkyl or aryl, and metal may be zinc (e.g. when used in combination with Compound (5-7) or Compound (5-10)), magnesium, lithium, or aluminum.

Additional examples of the vinyl components can be vinylboronic acid, dimethyl vinylboronate, diethyl vinylboronate, dipropyl vinylboronate, diisopropyl vinylboronate, dibutyl vinylboronate, 4,4,5,5-tetramethyl-2-vinyl-1,3,2-dioxaborolane, 4,4,6-trimethyl-2-vinyl-1,3,2-dioxaborinane, 6-methyl-2-vinyl-1,3,6,2-dioxazaborocane-4,8-dione, vinylboronic anhydride pyridine complex, (+)-vinylboronic acid pinanediol ester, 6-[(1R,2R,3S,5S)-2,6,6-trimethylbicyclo[3.1.1]hept-3-yl]-2-Vinyl-1,3,6,2-dioxazaborocane-4,8-dione, vinyltrimethylsilane, vinyltriethylsilane, dimethyldivinylsilane, tetravinylsilane, chloro(dimethyl)vinylsilane, trichlorovinylsilane, vinyltrimethoxysilane, triisopropoxy(vinyl)silane, triethoxyvinylsilane, tris(trimethylsiloxy)(vinyl)silane, triacetoxy(vinyl)silane, tris(allyloxy)(vinyl)silane, vinyltriisopropenoxysilane, tris(2-methoxyethoxy)(vinyl)silane, 1,3,5,7,9,11,13,15-octavinylpentacyclo[9.5.1.1~3,9~.1~5,15~.1~7,13~]octasiloxan, triphenoxy(vinyl)silane, 1,3,5,7,9,11,13-heptaisobutyl-15-vinylpentacyclo[9.5.1.1~3,9~.1~5,15~.1~7,13~]octasiloxane, 1-vinyl-2,8,9-trioxa-5-aza-1-silabicyclo[3.3.3]undecane, vinylzinc Chloride, vinylzinc bromide, vinyl lithium, vinyl magnesium chloride, vinyl magnesium bromide, and vinyl aluminum.

Any metal components and ligand components of the catalyst known in the art can also be employed. Metal components can include palladium(II) trifluoroacetate, palladium(II) acetylacetonate, allylpalladium(II) chloride dimer, palladium(II) acetate, palladium(II) pivalate, palladium(II) chloride, palladium(II) bromide, tris(dibenzylideneacetone)dipalladium, bis(dibenzylideneacetone)palladium, bis(acetonitrile)dichloropalladium(II), tris(dibenzylideneacetone)dipalladium(0)-chloroform adduct, tetrakis(triphenylphosphine)palladium(0), dichlorobis(tricyclohexylphosphine)palladium(II), bis(triphenylphosphine)palladium(II) dichloride, dichlorobis(tri-o-tolylphosphine)palladium(II), bis(di-tert-butyl(4-dimethylaminophenyl)

phosphine)dichloropalladium(II), [1,1'-bis(diphenylphosphino)ferrocene]dichloropalladium(II), [1,1'-bis(diphenylphosphino)ferrocene]dichloropalladium(II) complex with dichloromethane, [1,1'-bis(di-tert-butylphosphino)ferrocene]dichloropalladium(II), tetrakis(acetonitrile) palladium(II) tetrafluoroborate, (SPhos) palladium(II) phenethylamine chloride, (XPhos) palladium(II) phenethylamine chloride, (RuPhos) palladium(II) phenethylamine chloride, (t-BuXPhos) palladium(II) phenethylamine chloride, and (BrettPhos) palladium(II) phenethylamine chloride.

Non-limiting examples of ligand components may be tri-(2-furyl)phosphine, tri-tert-butylphosphine, tri-tert-butylphosphine hydro tetrafluoroborate, methyl-di-tert-butylphosphine, methyl-di-tert-butylphosphine hydro tetrafluoroborate, 4,5-bis(dicyclohexylphosphino)-9,9-dimethylxanthene, tri(cyclohexyl)phosphine, tri(2-furanyl)phosphine, 1,1'-bis(diphenylphosphino) ferrocene, 1,1'-bis(dicyclohexylphosphino) ferrocene, 1,1'-bis(ditertbutylphosphino) ferrocene, 1,3-bis-(2,6-diisopropylphenyl)imidazolinium chloride, 1,3-bis(2,4,6-trimethylphenyl)imidazolinium chloride, 1,3-diisopropylimidazolium tetrafluoroborate, 1,3-bis(1-adamantyl)imidazolium tetrafluoroborate, 2-(dicyclohexylphosphino)biphenyl, 2-dicyclohexylphosphino-2'-(N,N-dimethylamino)biphenyl, 2-dicyclohexylphosphino-2',4',6'-triisopropylbiphenyl, 2-dicyclohexylphosphino-2'-methylbiphenyl, 2-dicyclohexylphosphino-2',6'-diisopropoxybiphenyl, 2-(dicyclohexylphosphino)3,6-dimethoxy-2',4',6'-triisopropyl-1,1'-biphenyl, sodium 2'-dicyclohexylphosphino-2,6-dimethoxy-1,1'-biphenyl-3-sulfonate hydrate, 2-diphenylphosphino-2'-(N,N-dimethylamino)biphenyl, 2-di-tert-butylphosphino-2',4',6'-triisopropylbiphenyl, (2-biphenyl)di-tert-butylphosphine, 2-di-tert-butylphosphino-3,4,5,6-tetramethyl-2',4',6'-triisopropyl-1,1'-biphenyl, 2-di-tert-butylphosphino-2'-methylbiphenyl, 2-(di-tert-butylphosphino)-2',4',6'-triisopropyl-3,6-dimethoxy-1,1'-biphenyl, 2-di-tert-butylphosphino-2'-(N,N-dimethylamino)biphenyl, 2-{bis[3,5-bis(trifluoromethyl)phenyl]phosphino}-3,6-dimethoxy-2',4',6'-triisopropyl-1,1'-biphenyl, and the like.

Various bases may also be employed. Non-limiting examples may be lithium carbonate, sodium carbonate, cesium carbonate, beryllium carbonate, magnesium carbonate, calcium carbonate, strontium carbonate, barium carbonate, lithium hydroxide, sodium hydroxide potassium hydroxide, cesium hydroxide, beryllium hydroxide, magnesium hydroxide, calcium hydroxide, strontium hydroxide, barium hydroxide, lithium bicarbonate, sodium bicarbonate, potassium bicarbonate, cesium bicarbonate, beryllium bicarbonate, magnesium bicarbonate, calcium bicarbonate, strontium bicarbonate, barium bicarbonate, lithium hydride, sodium hydride, potassium hydride, magnesium hydride, calcium hydride, lithium tert-butoxide, sodium tert-butoxide, potassium tert-butoxide, cesium tert-butoxide, beryllium tert-butoxide, magnesium tert-butoxide, calcium tert-butoxide, strontium tert-butoxide, barium tert-butoxide, aluminum tert-butoxide, titanium tert-butoxide, 2,2,6,6-tetramethylpiperidine, 2,6-ditertbutylpyridine, 4-methyl-2,6-ditertbutylpyridine, trilithium phosphate, trisodium phosphate, tripotassium phosphate, tricesium phosphate, beryllium phosphate, magnesium phosphate, calcium phosphate, strontium phosphate, dilithium hydrogenphosphate, disodium hydrogenphosphate, dipotassium hydrogenphosphate, dicesium hydrogenphosphate, lithium dihydrogenphosphate, sodium dihydrogenphosphate, potassium dihydrogenphosphate, cesium dihydrogenphosphate, lithium tert-butylcarboxylate, sodium tert-butylcarboxylate, potassium tert-butylcarboxylate, cesium tert-butylcarboxylate, lithium acetate, sodium acetate, potassium acetate, cesium acetate, lithium propanoate, sodium propanoate, potassium propanoate, cesium propanoate, lithium isobutyrate, sodium isobutyrate, potassium isobutyrate, cesium isobutyrate, lithium adamantylcarboxylate, sodium adamantylcarboxylate, potassium adamantylcarboxylate, cesium adamantylcarboxylate, lithium trifluoroaceate, sodium trifluoroaceate, potassium trifluoroaceate, cesium trifluoroaceate, triethylamine, trimethylamine, tripropylamine, tributylamine, diisopropylethylamine, dicyclohexylmethylamine, lithium methoxide, lithium ethoxide, lithium isopropoxide, lithium propoxide, lithium butoxide, lithium phenoxide, sodium methoxide, sodium ethoxide, sodium isopropoxide, sodium butoxide, sodium phenoxide, potassium methoxide, potassium ethoxide, potassium isopropoxide, potassium propoxide, potassium butoxide, potassium phenoxide, cesium methoxide, cesium ethoxide, cesium isopropoxide, cesium propoxide, cesium butoxide, and cesium phenoxide.

Alternative solvents can be N,N-dimethylformamide, N,N-dimethylacetamide, N-methylpyrolidine, 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, dimethylsulfoxide, methanol, ethanol, n-propanol, 2-propanol, butanol, tert-butanol, benzene, and nitromethane.

Various additives may be employed, such as butylated hydroxytoluene, ascorbic acid, sodium ascorbate. Alternative palladium scavengers may be N-acetyl cysteine, activated charcoal, charcoal, ethylenediaminetetraacetic acid, 1,2-ethylenediamine, 1,2-diaminopropane, diethylenetriamine, triethylenetetramine, and tris(2-aminoethyl)amine.

The reaction may take place at temperatures ranging from about 70° C. or about 20° C. to about 100° C., and the reaction may take place in about 2 hours to about 6 hours or about 1 hour to about 48 hours.

Reaction of Compound (O) to Compound (5-4)

3-Vinyl-10,11-dihydro-5H-dibenzo[c,g]chromen-8(9H)-one (30 g) (Compound (O)) was combined with dichloromethane (60 mL), dimethylsulfoxide (150 mL) and water (11 mL) and cooled to about 15° C. N-Bromosuccinimide (21.3 g) was added in portions. After complete conversion, dichloromethane was added (135 mL). The mixture was washed with a 13% aqueous sodium thiosulfate solution (135 mL) followed by addition of dichloromethane (225 mL). The organic phase was washed with water (120 mL) and then concentrated under reduced pressure. Methylcyclohexane was added. The mixture was cooled to about 5° C. and filtered. The filter cake was washed with methylcyclohexane (100 mL) and then dried under reduced pressure at about 40° C. to provide 3-(2-bromo-1-hydroxyethyl)-10,11-dihydro-5H-dibenzo[c,g]chromen-8(9H)-one (Compound (5-4)). HRMS (ESI+ MS/MS) Calculated for $C_{19}H_{18}BrO_3$ m/z (M+H): 373.0439, and 375.0419; Found: 373.0450, and 375.0432; $^1$H NMR (400 MHz, CDCl$_3$) δ 7.74 (d, J=8.0 Hz, 1H), 7.62 (s, 1H), 7.58 (s, 1H), 7.41 (d, J=7.9 Hz, 1H), 7.23 (s, 1H), 5.11 (s, 2H), 5.03-4.85 (m, 1H), 3.74-3.62 (m, 1H), 3.60-3.46 (m, 1H), 3.05-2.86 (m, 2H), 2.75 (s, 1H), 2.68-2.56 (m, 2H), 2.23-2.06 (m, 2H).

Alternative reagents and reaction conditions to those disclosed above may also be employed. For example, various brominating agents may be employed, such as bromine, bromine monochloride, 5,5-dimethyl-1,3-dibromohydantoin, pyridinium tribromide, 2,4,4,6-tetrabromo-2,5-cyclohexadienone, dibromoisocyanuric Acid, tribromoisocyanuric Acid, N-bromoisocyanuric acid monosodium salt, N-bromo phthalimide, N-bromo acetamide, N,N'-dibromo-4-methylbenzenesulphonamide, sodium bromate, lithium bromate, potassium bromate, tetra-n-butylammonium tribromide, trimethylphenylammonium tribromide, trimethylammonium tribromide, triethylammonium tribromide, bromine on polymer support, 4-(dimethylamino)pyridine tribromide, pyridinium tribromide polymer bound, bromotrichloromethane, sodium hypobromite, lithium hypobromite, potassium hypobromite, beryllium hypobromite, magnesium hypobromite, calcium hypobromite, N,N-dibromobenzenesulfonamide, sodium bromite, lithium bromite, potassium bromite, N-bromo glutarimide, 1,3-dibromo-2,4-imidazolidinedione, 3-bromo-1-chloro-5,5-dimethylhydantoin, 1-bromo-5-ethyl-3,5-dimethyl-2,4-imidazolidinedione, 1,3-dibromo-5-ethyl-5-methylhydantoin, 1,3-dibromo-5-isopropyl-5-methylhydantoin, 3-bromo-5-methyl-5-phenyl-imidazolidine-2,4-dione, dibromo(triphenyl)phosphorane, carbon tetrabromide, bromoform, dibromomethane, hexabromoacetone, lithium bromide, sodium bromide, potassium bromide, cesium bromide, beryllium bromide, magnesium bromide, calcium bromide, aluminum bromide, indium bromide, titanium bromide, ferrous bromide, ferric bromide, tin bromide, and hydrobromic acid.

Alternative oxygenating agents may be employed. Non-limiting examples may include lithium carbonate, sodium carbonate, potassium carbonate, cesium carbonate, beryllium carbonate, magnesium carbonate, calcium carbonate, cerium carbonate, lithium bicarbonate, sodium bicarbonate, potassium bicarbonate, cesium bicarbonate, beryllium bicarbonate, magnesium bicarbonate, calcium bicarbonate, barium bicarbonate, lithium hydroxide, sodium hydroxide, potassium hydroxide, cesium hydroxide, beryllium hydroxide, magnesium hydroxide, calcium hydroxide, strontium hydroxide, barium hydroxide, formic acid, lithium formate, sodium formate, potassium formate, cesium formate, beryllium formate, magnesium formate, calcium formate, tert-butylcarboxylic acid, lithium tert-butylcarboxylate, sodium tert-butylcarboxylate, potassium tert-butylcarboxylate, cesium tert-tutylcarboxylate, acetic acid, lithium acetate, sodium acetate, potassium acetate, cesium acetate, propanoic acid, lithium propanoate, sodium propanoate, potassium propanoate, cesium propanoate, butyric acid, lithium butyrate, sodium butyrate, potassium butyrate, cesium butyrate, beryllium butyrate, magnesium butyrate, calcium butyrate, barium butyrate, isobutyric acid, lithium isobutyrate, sodium isobutyrate, potassium isobutyrate, cesium isobutyrate, adamantylcarboxylic acid, lithium adamantylcarboxylate, sodium adamantylcarboxylate, potassium adamantylcarboxylate, cesium adamantylcarboxylate, lithium trifluoroaceate, sodium trifluoroaceate, potassium trifluoroaceate, cesium trifluoroaceate, benzoic acid, lithium benzoate, sodium benzoate, potassium benzoate, cesium benzoate, beryllium benzoate, magnesium benzoate, calcium benzoate, 4-nitrobenzoic acid, lithium 4-nitrobenzoate, sodium 4-nitrobenzoate, potassium 4-nitrobenzoate, cesium 4-nitrobenzoate, beryllium 4-nitrobenzoate, magnesium 4-nitrobenzoate, calcium 4-nitrobenzoate, 4-fluorobenzoic acid, lithium 4-fluorobenzoate, sodium 4-fluorobenzoate, potassium 4-fluorobenzoate, cesium 4-fluorobenzoate, beryllium 4-fluorobenzoate, magnesium 4-fluorobenzoate, and calcium 4-fluorobenzoate.

Alternative solvents can be dimethylsulfoxide, N,N-dimethylformamide, N,N-dimethylacetamide, N-methylpyrolidine, 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, methanol, ethanol, n-propanol, 2-propanol, butanol, tert-butanol, benzene, and nitromethane.

Temperatures can range from about 0° C. to about 5° C. or about −10° C. to about 100° C., and reaction times may range from about 30 minutes to about 24 hours or about 30 minutes to about 4 hours.

Reaction of Compound (5-4) to Compound (5-5)

To 3-(2-bromo-1-hydroxyethyl)-10,11-dihydro-5H-dibenzo[c,g]chromen-8(9H)-one (Compound (5-4)) (8.0 g) in dichloromethane (181 mL) at about 2° C. was added a solution of pyridinium tribromide (7.7 g) in MeOH (8.1 mL). After complete conversion, the reaction mixture was extracted with water (23 mL) and aqueous hydrochloric acid (3.4% wt., 2×25 mL) to yield a solution containing the product, 9-bromo-3-(2-bromo-1-hydroxyethyl)-10,11-dihydro-5H-dibenzo[c,g]chromen-8(9H)-one (Compound (5-5)). HRMS (ESI$^+$ MS/MS) Calculated for $C_{19}H_{17}Br_2O_3$ m/z (M+H): 450.9544 and 452.9524; Found: 450.9524, and 452.9534; $^1$H NMR (400 MHz, CDCl$_3$) δ 7.75 (d, J=8.1 Hz, 1H), 7.68 (s, 1H), 7.61 (s, 1H), 7.42 (d, J=7.5 Hz, 1H), 7.24 (s, 1H), 5.13 (s, 2H), 4.99-4.96 (m, 1H), 4.73 (dd, J=4.1, 4.1 Hz, 1H), 3.69-3.66 (m, 1H), 3.58-3.53 (m, 1H), 3.35-3.27 (m, 1H), 2.96-2.90 (m, 1H), 2.58-2.44 (m, 2H), C—OH not observed.

Alternative reagents and reaction conditions to those disclosed above may also be employed. For example, various brominating agents may be employed, such as bromine, bromine monochloride, N-bromosuccinimide, 5,5-dimethyl-1,3-dibromohydantoin, 2,4,4,6-tetrabromo-2,5-cyclohexadienone, dibromoisocyanuric acid, tribromoisocyanuric acid, N-bromoisocyanuric acid monosodium salt, N-bromo phthalimide, N-bromo acetamide, N,N'-dibromo-4-methylbenzenesulphonamide, sodium bromate, lithium bromate, potassium bromate, tetra-n-butylammonium tribromide, trimethylphenylammonium tribromide, trimethylammonium tribromide, triethylammonium tribromide, bromine on polymer support, 4-(dimethylamino)pyridine tribromide, pyridinium tribromide polymer bound, bromotrichloromethane, sodium hypobromite, lithium hypobromite, potassium hypobromite, beryllium hypobromite, magnesium hypobromite, calcium hypobromite, N,N-dibromobenzenesulfonamide, sodium bromite, lithium bromite, potassium bromite, N-bromo glutarimide, 1,3-dibromo-2,4-imidazolidinedione, 3-bromo-1-chloro-5,5-dimethylhydantoin, 1-bromo-5-ethyl-3,5-dimethyl-2,4-imidazolidinedione, 1,3-dibromo-5-ethyl-5-methylhydantoin, 1,3-dibromo-5-isopropyl-5-methylhydantoin, 3-bromo-5-methyl-5-phenyl-imidazolidine-2,4-dione, dibromo(triphenyl)phosphorane, carbon tetrabromide, bromoform, dibromomethane, hexabromoacetone, lithium bromide, sodium bromide, potassium bromide, cesium bromide, beryllium bromide, magnesium bromide, calcium bromide, aluminum bromide, indium bromide, titanium bromide, ferrous bromide, ferric bromide, tin bromide, and hydrobromic acid.

Alternative solvents can include 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, ethanol, n-propanol, 2-propanol, butanol, tert-butanol, benzene, and nitromethane.

The reaction may take place at temperatures that range from about 0° C. to about 5° C. or about −10° C. to about 100° C. and at time lengths of about 30 minutes to about 4 hours or about 30 minutes to about 24 hours.

Reaction of Compound (5-5) to Compound (I-a)

A solution of 9-bromo-3-(2-bromo-1-hydroxyethyl)-10,11-dihydro-5H-dibenzo[c,g]chromen-8(9H)-one (approx. 3.2 g) (Compound (5-5)) in dichloromethane (60 mL) at about 20° C. was combined with sodium bicarbonate (0.8 g), sodium bromide (0.8 g), TEMPO (56 mg) and water (18 mL). The mixture was combined with an aqueous solution of sodium hypochlorite (10.3% wt., 9.4 mL). After completion of the reaction, isopropyl alcohol (9.1 mL) was added followed by an aqueous solution of hydrochloric acid (10% wt., 4.3 mL). The mixture was filtered and the cake washed with water (29 mL) and a 1:5 mixture of isopropyl alcohol and dichloromethane at about 5° C. The solids were collected and dried under vacuum to obtain 9-bromo-3-(2-bromoacetyl)-10,11-dihydro-5H-dibenzo[c,g]chromen-8(9H)-one (Compound (I-a)). HRMS (ESI$^+$ MS/MS) Calculated for Chemical Formula: $C_{19}H_{15}Br_2O_3$ m/z (M+H): 448.9388 and 450.9367; Found: 448.9396, and 450.9380. $^1$H NMR (400 MHz, CDCl$_3$) δ 8.03-8.01 (m, 1H), 7.85 (d, J=8.2 Hz, 1H), 7.82 (s, 1H), 7.71 (s, 1H), 7.67 (s, 1H), 5.19 (s, 2H), 4.74 (dd, J=4.1, 4.1 Hz, 1H), 4.45 (s, 2H), 3.37-3.29 (m, 1H), 2.99-2.92 (m, 1H), 2.59-2.46 (m, 2H); $^{13}$C NMR (100 MHz, CDCl$_3$) δ 190.4, 189.6, 154.2, 136.6, 134.1, 133.9, 132.9, 131.8, 129.3, 127.2, 125.6, 124.2, 123.3, 117.0, 68.1, 49.9, 31.8, 30.4, 25.5.

Alternative reagents and reaction conditions to those disclosed above may also be employed. For example, alternative catalysts, in lieu of TEMPO, may include tetrapropylammonium perruthenate, 2-azaadamantane-N-oxyl, 1-methyl-2-azaadamantane-N-oxyl, 1,3-dimethyl-2-azaadamantane-N-oxyl, and 4-acetamido-2,2,6,6-tetramethylpiperidine-1-oxoammonium tetrafluoroborate.

Various oxidizing agents may be employed. Examples of oxidizing agents can include diacetoxy iodobenzene, di(trifluoxoacetoxy) iodobenzene, dichloro iodobenzene, potassium persulfate, sodium perborate, sodium bromate, sodium iodate, sodium periodate, urea hydrogen peroxide, tert-butylhydroperoxide, N-methylmorpholine-N-oxide, trimethylammonium-N-oxide, sodium dichloroisocyanuric acid, iodosobenzene, N-bromo succinimide, N-bromoacetamide, N-bromophthalimide, sodium bromite, sodium hypobromite, m-chloroperbenzoic acid, 2-iodoxybenzoic acid, ruthenium trichloride, rhodium(I) tris-(triphenylphosphine) chloride, palladium(II) acetate, titanium tetraisopropoxide, ferric bromide, copper(I) chloride, copper(II) chloride, copper(I) bromide, copper(II) bromide, tetrapropylammonium perruthenate, N-chloro succinimide, 1,1,1-triacetoxy-1,1-dihydro-1,2-benziodoxol-3(1H)-one, trimethyl aluminium, aluminum triisopropoxide, dimethylsulfoxide, potassium peroxymonosulfate, cericammonium nitrate, oxygen, trichloroisicyanuric acid, cromine, iodine, chlorine, bromine, bromine monochloride, 5,5-dimethyl-1,3-dibromohydantoin, pyridinium tribromide, 2,4,4,6-tetrabromo-2,5-cyclohexadienone, dibromoisocyanuric acid, tribromoisocyanuric acid, N-bromoisocyanuric acid monosodium salt, N-bromo phthalimide, N-bromo acetamide, N,N'-dibromo-4-methylbenzenesulphonamide, sodium bromate, lithium bromate, potassium bromate, tetra-n-butylammonium tribromide, trimethylphenylammonium tribromide, trimethylammonium tribromide, triethylammonium tribromide, bromine on polymer support, 4-(dimethylamino)pyridine tribromide, pyridinium tribromide polymer bound, bromotrichloromethane, sodium hypobromite, lithium hypobromite, potassium hypobromite, beryllium hypobromite, magnesium hypobromite, calcium hypobromite, N,N-dibromobenzenesulfonamide, sodium bromite, lithium bromite, potassium bromite, N-bromo glutarimide, 1,3-dibromo-2,4-imidazolidinedione, 3-bromo-1-chloro-5,5-dimethylhydantoin, 1-bromo-5-ethyl-3,5-dimethyl-2,4-imidazolidinedione, 1,3-dibromo-5-ethyl-5-methylhydantoin, 1,3-dibromo-5-isopropyl-5-methylhydantoin, and 3-bromo-5-methyl-5-phenyl-imidazolidine-2,4-dione, dibromo(triphenyl)phosphorane.

Alternative additives can include hydrobromic acid, lithium bromide, sodium bromide, potassium bromide, cesium bromide, beryllium bromide, magnesium bromide, calcium bromide, tetrabutylammonium bromide, tetraethylammonium bromide, tetramethyl bromide, pyridinium bromide, aluminum bromide, titanium bromide, indium bromide, ferric bromide, ferrous bromide, copper(I) bromide, copper(II) bromide, hydroiodic acid, lithium iodide, sodium iodide, potassium iodide, cesium iodide, beryllium iodide, magnesium iodide, calcium iodide, tetrabutylammonium iodide, tetraethylammonium iodide, tetramethyl iodide, pyridinium iodide, aluminum iodide, titanium iodide, indium iodide, ferric iodide, ferrous iodide, copper(I) iodide, and copper(II) iodide.

Various bases may be employed, such as lithium carbonate, sodium carbonate, cesium carbonate, beryllium carbonate, magnesium carbonate, calcium carbonate, strontium carbonate, barium carbonate, lithium hydroxide, sodium hydroxide, potassium hydroxide, cesium hydroxide, beryllium hydroxide, magnesium hydroxide, calcium hydroxide, strontium hydroxide, barium hydroxide, lithium bicarbonate, sodium bicarbonate, potassium bicarbonate, cesium bicarbonate, beryllium bicarbonate, magnesium bicarbonate, calcium bicarbonate, strontium bicarbonate, barium bicarbonate, lithium tert-butoxide, sodium tert-butoxide, potassium tert-butoxide, cesium tert-butoxide, beryllium tert-butoxide, magnesium tert-butoxide, calcium tert-butoxide, strontium tert-butoxide, barium tert-butoxide, trilithium phosphate, trisodium phosphate, tripotassium phosphate, tricesium phosphate, beryllium phosphate, magnesium phosphate, calcium phosphate, strontium phosphate, dilithium hydrogenphosphate, disodium hydrogenphosphate, dipotassium hydrogenphosphate, dicesium hydrogenphosphate, lithium dihydrogenphosphate, sodium dihydrogenphosphate, potassium dihydrogenphosphate, and cesium dihydrogenphosphate.

Alternative solvents can include 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, tert-butanol, benzene, and nitromethane.

The reaction may take place at temperatures that range from about 20° C. to about 25° C. or about 0° C. to about 40° C. and at time lengths of about 30 minutes to about 2 hours or about 0.2 hours to about 24 hours.

Example 6

Alternative Synthesis of Compound (I-a)

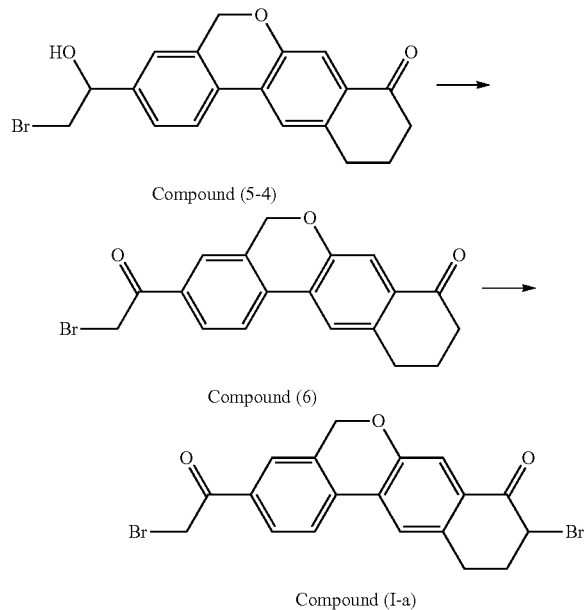

Compound (5-4)

Compound (6)

Compound (I-a)

Reaction of Compound (5-4) to Compound (6)

To a 1 L reactor was charged 3-(2-bromo-1-hydroxyethyl)-10,11-dihydro-5H-dibenzo[c,g]chromen-8(9H)-one (25 g), (Compound (5-4)) dichloromethane (370 mL), and TEMPO (0.2 g). The mixture was cooled to about 2° C. A solution of sodium bicarbonate (7.4 g), sodium bromide (7.4 g) and water (130 mL) was charged and the mixture agitated. The mixture was combined with an aqueous solution of sodium hypochlorite (11.9% wt., 80 mL). After completion of the reaction, 2-propanol (40 mL) was charged and the mixture warmed to about 25° C. A volume of about two-thirds of dichloromethane was removed under reduced pressure, the mixture cooled to about 5° C. and then filtered through a fritted funnel. The filter cake was washed twice with water (75 mL) and with dichloromethane (30 mL) and then dried at about 40° C. under reduced pressure to provide 3-(2-bromoacetyl)-10,11-dihydro-5H-dibenzo[c,g]chromen-8(9H)-one (Compound (6)). $^1$H NMR (400 MHz, CDCl3) δ 8.01 (d, J=8.1 Hz, 1H), 8.01 (d, J=8.1 Hz, 1H), 7.84 (d, J=8.2 Hz, 1H), 7.84 (d, J=8.2 Hz, 1H), 7.81 (s, 1H), 7.81 (s, 1H), 7.65 (s, 2H), 7.65 (s, 2H), 5.18 (s, 2H), 4.45 (s, 2H), 3.08-2.91 (m, 2H), 2.75-2.59 (m, 2H), 2.26-2.07 (m, 2H).

Alternative reagents and reaction conditions to those disclosed above may also be employed. For example, alternative catalysts can include tetrapropylammonium perruthenate, 2-azaadamantane-N-oxyl, 1-methyl-2-azaadamantane-N-oxyl, 1,3-dimethyl-2-azaadamantane-N-oxyl, and 4-acetamido-2,2,6,6-tetramethylpiperidine-1-oxoammonium tetrafluoroborate.

Various oxidizing agents may be employed. Non-limiting examples include diacetoxy iodobenzene, di(trifluoroacetoxy) iodobenzene, dichloro iodobenzene, potassium persulfate, sodium perborate, sodium bromate, sodium iodate, sodium periodate, urea hydrogen peroxide, tert-butylhydroperoxide, N-methylmorpholine-N-oxide, trimethylammonium-N-oxide, sodium dichloroisocyanuric acid, iodosobenzene, N-bromo succinimide, N-bromoacetamide, N-bromophthalimide, sodium bromite, sodium hypobromite, m-chloroperbenzoic acid, 2-iodoxybenzoic acid, ruthenium trichloride, rhodium(I) tris-(triphenylphosphine) chloride, palladium(II) acetate, titanium tetraisopropoxide, ferric bromide, copper(I) chloride, copper(II) chloride, copper(I) bromide, copper(II) bromide, tetrapropylammonium perruthenate, N-chloro succinimide, 1,1,1-triacetoxy-1,1-dihydro-1,2-benziodoxol-3(1H)-one, trimethyl aluminium, aluminum triisopropoxide, dimethylsulfoxide, potassium peroxymonosulfate, cericammonium nitrate, oxygen, trichloroisicyanuric acid, cromine, iodine, chlorine, bromine, bromine monochloride, 5,5-dimethyl-1,3-dibromohydantoin, pyridinium tribromide, 2,4,4,6-tetrabromo-2,5-cyclohexadienone, dibromoisocyanuric acid, tribromoisocyanuric Acid, N-bromoisocyanuric acid monosodium salt, N-bromo phthalimide, N-bromo acetamide, N,N'-dibromo-4-methylbenzenesulphonamide, sodium bromate, lithium bromate, potassium bromate, tetra-n-butylammonium tribromide, trimethylphenylammonium tribromide, trimethylammonium tribromide, triethylammonium tribromide, bromine on polymer support, 4-(dimethylamino)pyridine tribromide, pyridinium tribromide polymer bound, bromotrichloromethane, sodium hypobromite, lithium hypobromite, potassium hypobromite, beryllium hypobromite, magnesium hypobromite, calcium hypobromite, N,N-dibromobenzenesulfonamide, sodium bromite, lithium bromite, potassium bromite, N-bromo glutarimide, 1,3-dibromo-2,4-imidazolidinedione, 3-bromo-1-chloro-5,5-dimethylhydantoin, 1-bromo-5-ethyl-3,5-dimethyl-2,4-imidazolidinedione, 1,3-dibromo-5-ethyl-5-methylhydantoin, 1,3-dibromo-5-isopropyl-5-methylhydantoin, and 3-bromo-5-methyl-5-phenyl-imidazolidine-2,4-dione, and dibromo(triphenyl)phosphorane.

Alternative additives may be employed, such as hydrobromic acid, lithium bromide, sodium bromide, potassium bromide, cesium bromide, beryllium bromide, magnesium bromide, calcium bromide, tetrabutylammonium bromide, tetraethylammonium bromide, tetramethyl bromide, pyridinium bromide, aluminum bromide, titanium bromide, indium bromide, ferric bromide, ferrous bromide, copper(I) bromide, copper(II) bromide, hydroiodic acid, lithium iodide, sodium iodide, potassium iodide, cesium iodide, beryllium iodide, magnesium iodide, calcium iodide, tetrabutylammonium iodide, tetraethylammonium iodide, tetramethyl iodide, pyridinium iodide, aluminum iodide, titanium iodide, indium iodide, ferric iodide, ferrous iodide, copper (I) iodide, and copper (II) iodide.

Various bases may be employed, such as lithium carbonate, sodium carbonate, cesium carbonate, beryllium carbonate, magnesium carbonate, calcium carbonate, strontium carbonate, barium carbonate, lithium hydroxide, sodium hydroxide, potassium hydroxide, cesium hydroxide, beryllium hydroxide, magnesium hydroxide, calcium hydroxide, strontium hydroxide, barium hydroxide, lithium bicarbonate, sodium bicarbonate, potassium bicarbonate, cesium bicarbonate, beryllium bicarbonate, magnesium bicarbonate, calcium bicarbonate, strontium bicarbonate, barium bicarbonate, lithium tert-butoxide, sodium tert-butoxide, potassium tert-butoxide, cesium tert-butoxide, beryllium tert-butoxide, magnesium tert-butoxide, calcium tert-butoxide, strontium tert-butoxide, barium tert-butoxide, trilithium phosphate, trisodium phosphate, tripotassium phosphate, tricesium phosphate, beryllium phosphate, magnesium phosphate, calcium phosphate, strontium phosphate, dilithium hydrogenphosphate, disodium hydrogenphosphate, dipotassium hydrogenphosphate, dicesium hydrogenphosphate, lithium dihydrogenphosphate, sodium dihydrogenphosphate, potassium dihydrogenphosphate, and cesium dihydrogenphosphate.

Alternative solvents can be employed. Non-limiting examples can include 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl Ether, 1,4-dioxane, 1,2-dimethoxyethane, chloroform, acetonitrile, toluene, dichloromethane, 1,2-dichloroethane, tert-butanol, benzene, and nitromethane.

The reaction may take place at temperatures that range from about 20° C. to about 25° C. or about 0° C. to about 40° C. and at time lengths of about 30 minutes to about 2 hours or about 0.2 hours to about 6 hours.

Reaction of Compound (6) to Compound (I-a)

A mixture of 3-(2-bromoacetyl)-10,11-dihydro-5H-dibenzo[c,g]chromen-8(9H)-one (2.58 g) (Compound (6)), pyridinium tribromide (2.56 g), dichloromethane (22 mL) and methanol (2.5 mL) was stirred at ambient temperature for 3 hours. The mixture was filtered, the filter cake washed with dichloromethane (10 mL) and then dried under reduced pressure at 40° C. to give 9-bromo-3-(2-bromoacetyl)-10,11-dihydro-5H-dibenzo[c,g]chromen-8(9H)-one (Compound (I-a)). HRMS (ESI+ MS/MS) Calculated for Chemical Formula: $C_{19}H_{15}Br_2O_3$ m/z (M+H): 448.9388 and 450.9367; Found: 448.9396, and 450.9380. $^1$H NMR (400 MHz, CDCl$_3$) δ 8.03-8.01 (m, 1H), 7.85 (d, J=8.2 Hz, 1H), 7.82 (s, 1H), 7.71 (s, 1H), 7.67 (s, 1H), 5.19 (s, 2H), 4.74 (dd, J=4.1, 4.1 Hz, 1H), 4.45 (s, 2H), 3.37-3.29 (m, 1H), 2.99-2.92 (m, 1H), 2.59-2.46 (m, 2H).

Alternative reagents and reaction conditions to those disclosed above may also be employed. For example, additional starting material in lieu of Compound (6) may be 3-acetyl-10,11-dihydro-5H-dibenzo[c,g]chromen-8(9H)-one and 3-acetyl-9-bromo-10,11-dihydro-5H-dibenzo[c,g]chromen-8(9H)-one.

Various brominating agents may be employed. Non-limiting examples can include bromine, bromine monochloride, N-bromosuccinimide, 5,5-dimethyl-1,3-dibromohydantoin, 2,4,4,6-tetrabromo-2,5-cyclohexadienone, dibromoisocyanuric acid, tribromoisocyanuric acid, N-bromoisocyanuric acid monosodium salt, N-bromo phthalimide, N-bromo acetamide, N,N'-dibromo-4-methylbenzenesulphonamide, sodium bromate, lithium bromate, potassium bromate, tetra-n-butylammonium tribromide, trimethylphenylammonium tribromide, trimethylammonium tribromide, triethylammonium tribromide, bromine on polymer support, 4-(dimethylamino)pyridine tribromide, pyridinium tribromide polymer bound, bromotrichloromethane, sodium hypobromite, lithium hypobromite, potassium hypobromite, beryllium hypobromite, magnesium hypobromite, calcium hypobromite, N,N-dibromobenzenesulfonamide, sodium bromite, lithium bromite, potassium bromite, N-bromo glutarimide, 1,3-dibromo-2,4-imidazolidinedione, 3-bromo-1-chloro-5,5-dimethylhydantoin, 1-bromo-5-ethyl-3,5-dimethyl-2,4-imidazolidinedione, 1,3-dibromo-5-ethyl-5-methylhydantoin, 1,3-dibromo-5-isopropyl-5-methylhydantoin, 3-bromo-5-methyl-5-phenyl-imidazolidine-2,4-dione, dibromo(triphenyl)phosphorane, carbon tetrabromide, bromoform, dibromomethane, hexabromoacetone, lithium bromide, sodium bromide, potassium bromide, cesium bromide, beryllium bromide, magnesium bromide, calcium bromide, aluminum bromide, indium bromide, titanium bromide, ferrous bromide, ferric bromide, tin bromide, and hydrobromic acid.

Alternative solvents may be 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, ethanol, n-propanol, 2-propanol, butanol, tert-butanol, benzene, and nitromethane.

The reaction may take place at temperatures that range from about 0° C. to about 5° C. or about −10° C. to about 100° C. and at time lengths of about 30 minutes to about 4 hours or about 30 minutes to about 24 hours.

Example 7

Alternative Synthesis of Compound (I-a)

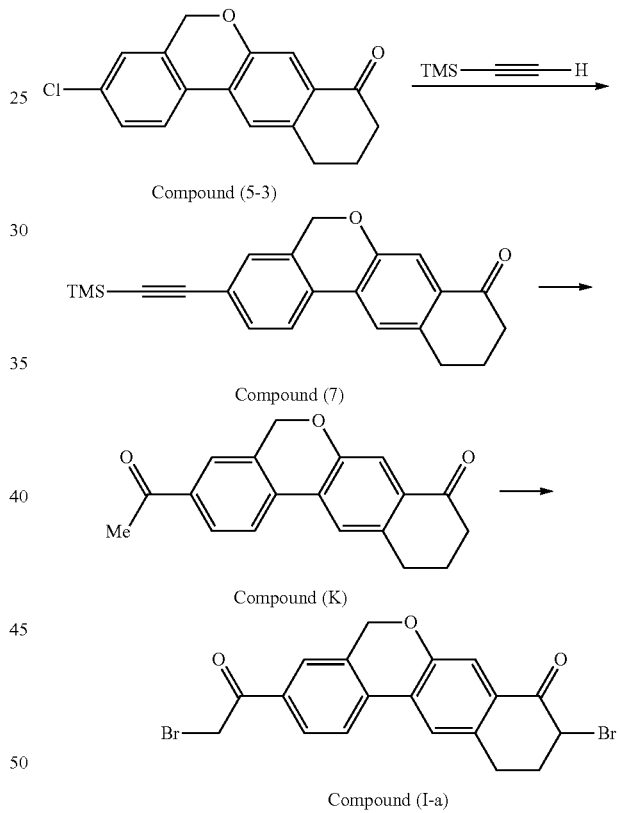

Reaction of Compound (5-3) to Compound (7)

A reaction flask at ambient temperature was charged with 3-chloro-10,11-dihydro-5H-dibenzo[c,g]chromen-8(9H)-one (10.0 g) (Compound (5-3)), powdered anhydrous tripotassium phosphate (22.4 g), 2-dicyclohexylphosphino-2',4',6'-triisopropylbiphenyl ("XPhos") (1.34 g), and PdCl$_2$(MeCN)$_2$ (364 mg). Acetonitrile (140 mL) was added followed by trimethylsilylacetylene (18 mL). The mixture was heated to about 65° C. After about 6 h, the reaction was judged complete, and the mixture was cooled to about 20° C. The mixture was drained and filtered through a fritted funnel, and the filter cake was washed with MeCN. The filtrate was concentrated to about 150 mL under reduced pressure and extracted with heptane (50 mL, then 3×100 mL). N-Acetyl cysteine (15 g) was added to the MeCN phase, and the mixture was agitated for about 5 h at about 45° C. The mixture was cooled to about 23° C., filtered through a fritted funnel, and the filter cake was washed with MeCN. The filtrate was concentrated to about 120 mL under reduced pressure. Water (120 mL) was added and the mixture was agitated for about 40 minutes at about 45° C. and then cooled to ambient temperature. After about 30 minutes the mixture was filtered through a fritted funnel to provide 3-((trimethylsilyl)ethynyl)-10,11-dihydro-5H-dibenzo[c,g]chromen-8(9H)-one (Compound (7)). MS (ESI$^+$ MS/MS) Calculated for Chemical Formula: $C_{22}H_{23}O_2Si$ m/z (M+H): 347.1467; Found: 347.1486. $^1$H NMR (400 MHz, CDCl$_3$) δ 7.65 (d, J=8.1 Hz, 1H), 7.60 (s, 1H), 7.55 (s, 1H), 7.47 (dd, J=8.1, 1.4 Hz, 1H), 7.27 (s, 1H), 5.06 (s, 2H), 2.95 (t, J=6.1 Hz, 2H), 2.67-2.59 (m, 2H), 2.18-2.08 (m, 2H), 0.26 (s, 9H).

Alternative reagents and reaction conditions to those disclosed above may also be employed. For example, alternative starting material, in lieu of 3-chloro-10,11-dihydro-5H-dibenzo[c,g]chromen-8(9H)-one, may be compounds of the following structures:

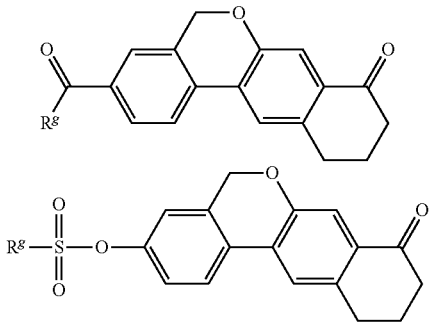

wherein R$^g$ may be alkoxy, aryloxy, or heterocyclooxy. Other alternative starting material can include 3-chloro-10,11-dihydro-5H-dibenzo[c,g]chromen-8(9H)-one, 3-bromo-10,11-dihydro-5H-dibenzo[c,g]chromen-8(9H)-one, 3-iodo-10,11-dihydro-5H-dibenzo[c,g]chromen-8(9H)-one, 8-oxo-8,9,10,11-tetrahydro-5H-dibenzo[c,g]chromen-3-yltrifluoromethanesulfonate, 8-oxo-8,9,10,11-tetrahydro-5H-dibenzo[c,g]chromen-3-yl benzenesulfonate, 8-oxo-8,9,10,11-tetrahydro-5H-dibenzo[c,g]chromen-3-yl 4-methylbenzenesulfonate, 8-oxo-8,9,10,11-tetrahydro-5H-dibenzo[c,g]chromen-3-yl 4-fluorobenzenesulfonate, 8-oxo-8,9,10,11-tetrahydro-5H-dibenzo[c,g]chromen-3-yl 4-(trifluoromethyl)benzenesulfonate, 8-oxo-8,9,10,11-tetrahydro-5H-dibenzo[c,g]chromene-3-carboxylic acid, lithium 8-oxo-8,9,10,11-tetrahydro-5H-dibenzo[c,g]chromene-3-carboxylate, sodium 8-oxo-8,9,10,11-tetrahydro-5H-dibenzo[c,g]chromene-3-carboxylate, potassium 8-oxo-8,9,10,11-tetrahydro-5H-dibenzo[c,g]chromene-3-carboxylate, cesium 8-oxo-8,9,10,11-tetrahydro-5H-dibenzo[c,g]chromene-3-carboxylate, methyl 8-oxo-8,9,10,11-tetrahydro-5H-dibenzo[c,g]chromene-3-carboxylate, ethyl 8-oxo-8,9,10,11-tetrahydro-5H-dibenzo[c,g]chromene-3-carboxylate, propyl 8-oxo-8,9,10,11-tetrahydro-5H-dibenzo[c,g]chromene-3-carboxylate, isopropyl 8-oxo-8,9,10,11-tetrahydro-5H-dibenzo[c,g]chromene-3-carboxylate, butyl 8-oxo-8,9,10,11-tetrahydro-5H-dibenzo[c,g]chromene-3-carboxylate, isobutyl 8-oxo-8,9,10,11-tetrahydro-5H-dibenzo[c,g]chromene-3-carboxylate, 2,2,2-trifluoroethyl 8-oxo-8,9,10,11-tetrahydro-5H-dibenzo[c,g]chromene-3-carboxylate, phenyl 8-oxo-8,9,10,11-tetrahydro-5H-dibenzo[c,g]chromene-3-carboxylate, p-tolyl 8-oxo-8,9,10,11-tetrahydro-5H-dibenzo[c,g]chromene-3-carboxylate, 4-nitrophenyl 8-oxo-8,9,10,11-tetrahydro-5H-dibenzo[c,g]chromene-3-carboxylate, 4-fluorophenyl 8-oxo-8,9,10,11-tetrahydro-5H-dibenzo[c,g]chromene-3-carboxylate, 4-(trifluoromethyl)phenyl 8-oxo-8,9,10,11-tetrahydro-5H-dibenzo[c,g]chromene-3-carboxylate, 4-methoxyphenyl 8-oxo-8,9,10,11-tetrahydro-5H-dibenzo[c,g]chromene-3-carboxylate, trifluoromethyl 8-oxo-8,9,10,11-tetrahydro-5H-dibenzo[c,g]chromene-3-carboxylate, difluoromethyl 8-oxo-8,9,10,11-tetrahydro-5H-dibenzo[c,g]chromene-3-carboxylate, and fluoromethyl 8-oxo-8,9,10,11-tetrahydro-5H-dibenzo[c,g]chromene-3-carboxylate.

Alternative metal components and ligand components of the catalyst may be employed. Non-limiting examples of metal components can include palladium(II) trifluoroacetate, palladium (II) acetylacetonate, allylpalladium(II) chloride dimer, palladium(II) acetate, palladium (II) pivalate, palladium(II) chloride, palladium (II) bromide, tris(dibenzylideneacetone)dipalladium, bis(dibenzylideneacetone)palladium, bis(acetonitrile)dichloropalladium(II), tris(dibenzylideneacetone)dipalladium(0)-chloroform adduct, tetrakis(triphenylphosphine)palladium(0), dichlorobis(tricyclohexylphosphine)palladium(II), bis(triphenylphosphine)palladium(II) dichloride, dichlorobis(tri-o-tolylphosphine)palladium(II), bis(di-tert-butyl(4-dimethylaminophenyl)phosphine)dichloropalladium(II), [1,1'-bis(diphenylphosphino)ferrocene]dichloropalladium(II), [1,1'-bis(diphenylphosphino)ferrocene]dichloropalladium(II) complex with dichloromethane, [1,1'-bis(di-tert-butylphosphino)ferrocene]dichloropalladium(II), tetrakis(acetonitrile)palladium(II) tetrafluoroborate, (SPhos) palladium(II) phenethylamine chloride, (XPhos) palladium(II) phenethylamine chloride, (RuPhos) palladium(II) phenethylamine chloride, (t-BuXPhos) palladium(II) phenethylamine chloride, and (BrettPhos) palladium(II) phenethylamine chloride.

Ligand components may be phosphines with at least one alkyl substituent. Non-limiting examples of ligand components may be tri-(2-furyl)phosphine, tri-tert-butylphosphine, tri-tert-butylphosphine hydro tetrafluoroborate, methyl-di-tert-butylphosphine, methyl-di-tert-butylphosphine hydro tetrafluoroborate, 4,5-bis(dicyclohexylphosphino)-9,9-dimethylxanthene, tri(cyclohexyl)phosphine, tri(2-furanyl)phosphine, 1,1'-bis(diphenylphosphino) ferrocene, 1,1'-bis(dicyclohexylphosphino) ferrocene, 1,1'-bis(ditertbutylphosphino) ferrocene, 1,3-bis-(2,6-diisopropylphenyl)imidazolinium chloride, 1,3-bis(2,4,6-trimethylphenyl)imidazolinium chloride, 1,3-diisopropylimidazolium tetrafluoroborate, 1,3-bis(1-adamantyl)imidazolium tetrafluoroborate, 2-(dicyclohexylphosphino)biphenyl, 2-dicyclohexylphosphino-2'-(N,N-dimethylamino)biphenyl, 2-dicyclohexylphosphino-2',4',6'-triisopropylbiphenyl, 2-Dicyclohexylphosphino-2'-methylbiphenyl, 2-dicyclohexylphosphino-2',6'-diisopropoxybiphenyl, 2-(dicyclohexylphosphino)3,6-dimethoxy-2',4',6'-triisopropyl-1,1'-biphenyl, sodium 2'-dicyclohexylphosphino-2,6-dimethoxy-1,1'-biphenyl-3-sulfonate hydrate, 2-diphenylphosphino-2'-(N,N-dimethylamino)biphenyl, 2-di-tert-butylphosphino-2',4',6'-triisopropylbiphenyl, (2-biphenyl)di-tert-butylphosphine, 2-di-tert-butylphosphino-3,4,5,6-tetramethyl-2',4',6'-triisopropyl-1,1'-biphenyl, 2-di-tert-butylphosphino-2'-methylbiphenyl, 2-(di-tert-butylphosphino)-2',4',6'-triisopropyl-3,6-dimethoxy-1,1'-biphenyl, 2-Di-tert-butylphosphino-2'-(N,N-dimethylamino)biphenyl, 2-{bis[3,5-bis(trifluoromethyl)phenyl]phosphino}-3,6-dimethoxy-2',4',6'-triisopropyl-1,1'- biphenyl, bis(diphenylphosphino)methane, 1,2-bis(diphenylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, bis(dicyclohexylphosphino)methane, 1,2-bis(dicyclohexylphosphino)ethane, 1,3-bis(dicyclohexylphosphino)propane, 1,3-bis(dicyclohexylphosphino)propane, 1,5-bis(dicyclohexylphosphino)pentane, 1,6-bis(dicyclohexylphosphino)hexane, bis(diisopropylphosphino)methane, 1,2-bis(diisopropylphosphino)ethane, 1,3-bis(diisopropylphosphino)propane, 1,3-bis(dicyclohexylphosphino)propane, 1,5-bis(diisopropylphosphino)pentane, 1,6-bis(diisopropylphosphino)hexane, bis(di-tert-butylphosphino)methane, 1,2-bis(di-tert-butylphosphino)ethane, 1,3-bis(di-tert-butylphosphino)propane, 1,3-bis(dicyclohexylphosphino)propane, 1,5-bis(di-tert-butylphosphino)pentane, 1,6-bis(di-tert-butylphosphino)hexane, bis(dicyclopentylphosphino)methane, 1,2-bis(dicyclopentylphosphino)ethane, 1,3-bis(dicyclopentylphosphino)propane, 1,3-bis(dicyclohexylphosphino)propane, 1,5-bis(dicyclopentylphosphino)pentane, 1,6-bis(dicyclopentylphosphino)hexane, and the like.

Various bases may also be employed, such as lithium carbonate, sodium carbonate, cesium carbonate, beryllium carbonate, magnesium carbonate, calcium carbonate, strontium carbonate, barium carbonate, lithium hydroxide, sodium hydroxide, potassium hydroxide, cesium hydroxide, beryllium hydroxide, magnesium hydroxide, calcium hydroxide, strontium hydroxide, barium hydroxide, lithium bicarbonate, sodium bicarbonate, potassium bicarbonate, cesium bicarbonate, beryllium bicarbonate, magnesium bicarbonate, calcium bicarbonate, strontium bicarbonate, barium bicarbonate, lithium hydride, sodium hydride, potassium hydride, magnesium hydride, calcium hydride, lithium tert-butoxide, sodium tert-butoxide, potassium tert-butoxide, cesium tert-butoxide, beryllium tert-butoxide, magnesium tert-butoxide, calcium tert-butoxide, strontium tert-butoxide, barium tert-butoxide, aluminum tert-butoxide, titanium tert-butoxide, 2,2,6,6-tetramethylpiperidine, 2,6-ditertbutylpyridine, 4-methyl-2,6-ditertbutylpyridine, trilithium phosphate, trisodium phosphate, tripotassium phosphate, tricesium phosphate, beryllium phosphate, magnesium phosphate, calcium phosphate, strontium phosphate, dilithium hydrogenphosphate, disodium hydorgenphosphate, dipotassium hydrogenphosphate, dicesium hydrogenphosphate, lithium dihydrogenphosphate, sodium dihydrogenphosphate, potassium dihydrogenphosphate, cesium dihydrogenphosphate, lithium tert-butylcarboxylate, sodium tert-butylcarboxylate, potassium tert-butylcarboxylate, cesium tert-butylcarboxylate, lithium acetate, sodium acetate, potassium acetate, cesium acetate, lithium propanoate, sodium propanoate, potassium propanoate, cesium propanoate, lithium isobutyrate, sodium isobutyrate, potassium isobutyrate, cesium isobutyrate, lithium adamantylcarboxylate, sodium adamantylcarboxylate, potassium adamantylcarboxylate, cesium adamantylcarboxylate, lithium trifluoroaceate, sodium trifluoroaceate, potassium trifluoroaceate, cesium trifluoroaceate, triethylamine, trimethylamine, tripropylamine, tributylamine, diisopropylethylamine, dicyclohexylmethylamine, lithium methoxide, lithium ethoxide, lithium isopropoxide, lithium propoxide, lithium butoxide, lithium phenoxide, sodium methoxide, sodium ethoxide, sodium isopropoxide, sodium butoxide, sodium phenoxide, potassium methoxide, potassium ethoxide, potassium isopropoxide, potassium propoxide, potassium butoxide, potassium phenoxide, cesium methoxide, cesium ethoxide, cesium isopropoxide, cesium propoxide, cesium butoxide, and cesium phenoxide.

Alternative solvents can include N,N-dimethylformamide, N,N-dimethylacetamide, N-methylpyrolidine, 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane dimethylsulfoxide, methanol, ethanol, n-propanol, 2-propanol, butanol, tert-butanol, benzene, and nitromethane.

The reaction may take place at temperatures that range from about 5° C. to about 100° C. and at time lengths of about 1 hour to about 48 hours.

Reaction of Compound (7) to Compound (K)

3-((Trimethylsilyl)ethynyl)-10,11-dihydro-5H-dibenzo[c,g]chromen-8(9H)-one (850 mg) was combined with formic acid (9.8 mL) at about 23° C. The mixture was heated to about 65° C. After about 3 h, the reaction was judged complete. The mixture was concentrated under reduced pressure; the resulting residue was purified by chromatography on a silica gel column eluting with a solvent gradient from 5% to 85% EtOAc/hexanes. The product containing fractions were combined and concentrated to provide 3-acetyl-10,11-dihydro-5H-dibenzo[c,g]chromen-8(9H)-one (Compound (K)): $^1$H NMR (400 MHz, CDCl$_3$) δ 8.00-7.94 (m, 1H), 7.81 (d, J=8.2 Hz, 1H), 7.77 (s, 1H), 7.64 (s, 2H), 5.16 (s, 2H), 2.98 (t, J=6.1 Hz, 2H), 2.69-2.64 (m, 2H), 2.63 (s, 3H), 2.21-2.09 (m, 2H).

Alternative reagents and reaction conditions to those disclosed above may also be employed. For example, alternative starting material, in lieu of Compound (K), may be 3-((triisopropylsilyl)ethynyl)-10,11-dihydro-5H-dibenzo[c,g]chromen-8(9H)-one, 3-((triethylsilyl)ethynyl)-10,11-dihydro-5H-dibenzo[c,g]chromen-8(9H)-one, 3-((tert-butyldiphenylsilyl)ethynyl)-10,11-dihydro-5H-dibenzo[c,g]chromen-8(9H)-one, 3-((methyldiphenylsilyl)ethynyl)-10,11-dihydro-5H-dibenzo[c,g]chromen-8(9H)-one, 3-(3-hydroxy-3-methylbut-1-ynyl)-10,11-dihydro-5H-dibenzo[c,g]chromen-8(9H)-one, 3-ethynyl-10,11-dihydro-5H-dibenzo[c,g]chromen-8(9H)-one, 3-(1-methoxyvinyl)-10,11-dihydro-5H-dibenzo[c,g]chromen-8(9H)-one, 3-(1-ethoxyvinyl)-10,11-dihydro-5H-dibenzo[c,g]chromen-8(9H)-one, 3-(1-(2-hydroxyethoxy)vinyl)-10,11-dihydro-5H-dibenzo[c,g]chromen-8(9H)-one, 3-(1-isopropoxyvinyl)-10,11-dihydro-5H-dibenzo[c,g]chromen-8(9H)-one, 3-(1-propoxyvinyl)-10,11-dihydro-5H-dibenzo[c,g]chromen-8(9H)-one, 3-(1-butoxyvinyl)-10,11-dihydro-5H-dibenzo[c,g]chromen-8(9H)-one, 3-(1-bromovinyl)-10,11-dihydro-5H-dibenzo[c,g]chromen-8(9H)-one, 3-(1-chlorovinyl)-10,11-dihydro-5H-dibenzo[c,g]chromen-8(9H)-one, 3-(2-methyl-1,3-dioxolan-2-yl)-10,11-dihydro-5H-dibenzo[c,g]chromen-8(9H)-one, 3-(2-methyl-1,3-dioxan-2-yl)-10,11-dihydro-5H-dibenzo[c,g]chromen-8(9H)-one, 3-(2-methyl-1,3-dioxepan-2-yl)-10,11-dihydro-5H-dibenzo[c,g]chromen-8(9H)-one, and 3-(2-methyl-1,3-dioxocan-2-yl)-10,11-dihydro-5H-dibenzo[c,g]chromen-8(9H)-one.

Alternative acids may include formic acid, acetic acid, propanoic acid, butyric acid, isobutyric acid, pentanoic acid, pivalic acid, trifluoroacetic acid, difluoroacetic acid, fluoroacetic acid, trichloroacetic acid, dichloroacetic acid, chloroacetic acid, benzoic acid, 4-nitrobenzoic acid, 4-fluorobenzoic acid, 4-chlorobenzoic acid, 4-fromobenzoic acid, 4-iodobenzoic acid, 4-methylbenzoic acid, 4-trifluoromethylbenzoic acid, phenol, 4-nitrophenol, 4-fluorophenol, 4-chlorophenol, 4-bromophenol, 4-iodophenol, 4-trifluoromethylphenol, 4-methylphenol, methylsulfonic acid, trifluoromethylsulfonic acid, benzenesulfonic acid, toluenesulfonic acid, 4-nitrobenzenesulfonic acid, 4-fluorobenzenesulfonic acid, 4-chlorobenzenesulfonic acid, 4-bromobenzenesulfonic acid, 4-iodobenzenesulfonic acid, 4-trifluoromethylbenzenesulfonic acid, tetrafluoroboric acid, fluoroantimonic acid, hydrofluoric acid, hydrochloric acid, hydrobromic acid, hydroiodic acid, phosphoric acid, and sulfuric acid.

Various solvents may be employed. Non-limiting examples include N,N-dimethylformamide, N-methylpyrolidine, 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane dimethylsulfoxide, methanol, ethanol, n-propanol, 2-propanol, butanol, tert-butanol, benzene, and nitromethane.

The reaction may take place at temperatures that range from about 0° C. to about 100° C. and at time lengths of about 12 minutes to about 48 hours.

Reaction of Compound (K) to Compound (I-a)

A reaction vessel at ambient temperature was charged with 3-acetyl-10,11-dihydro-5H-dibenzo[c,g]chromen-8(9H)-one (100 mg) (Compound (K)), 9:1 CH$_2$Cl$_2$/MeOH (3.4 mL) and pyridinium tribromide (246 mg). The solution was heated to about 35° C. After about 30 minutes, the reaction was judged complete. The mixture was cooled to about 23° C., diluted with EtOAc (50 mL) and sequentially washed with saturated aqueous Na$_2$S$_2$O$_3$ (20 mL), 2% aqueous NaHCO$_3$ (20 mL), water (20 mL), and brine (10 mL). The organic phase was dried over MgSO$_4$, filtered and concentrated under reduced pressure resulting in 9-bromo-3-(2-bromoacetyl)-10,11-dihydro-5H-dibenzo[c,g]chromen-8(9H)-one (Compound (I-a)): $^1$H NMR (400 MHz, CDCl$_3$) δ 8.03-8.01 (m, 1H), 7.85 (d, J=8.2 Hz, 1H), 7.82 (s, 1H), 7.71 (s, 1H), 7.67 (s, 1H), 5.19 (s, 2H), 4.74 (dd, J=4.1, 4.1 Hz, 1H), 4.45 (s, 2H), 3.37-3.29 (m, 1H), 2.99-2.92 (m, 1H), 2.59-2.46 (m, 2H).

Alternative reagents and reaction conditions to those disclosed above may also be employed. For example, in lieu of Compound (K), alternative starting material may be 3-(2-bromoacetyl)-10,11-dihydro-5H-dibenzo[c,g]chromen-8(9H)-one (Compound (6)) or 3-acetyl-9-bromo-10,11-dihydro-5H-dibenzo[c,g]chromen-8(9H)-one.

Various brominating agents may be used. Non-limiting examples can include bromine, bromine monochloride, N-bromosuccinimide, 5,5-dimethyl-1,3-dibromohydantoin, 2,4,4,6-tetrabromo-2,5-cyclohexadienone, dibromoisocyanuric acid, tribromoisocyanuric acid, N-bromoisocyanuric acid monosodium salt, N-bromo phthalimide, N-bromo acetamide, N,N'-dibromo-4-methylbenzenesulphonamide, sodium bromate, lithium bromate, potassium bromate, tetra-n-butylammonium tribromide, trimethylphenylammonium tribromide, trimethylammonium tribromide, triethylammonium tribromide, bromine on polymer support, 4-(dimethylamino)pyridine tribromide, pyridinium tribromide polymer bound, bromotrichloromethane, sodium hypobromite, lithium hypobromite, potassium hypobromite, beryllium hypobromite, magnesium hypobromite, calcium hypobromite, N,N-dibromobenzenesulfonamide, sodium bromite, lithium bromite, potassium bromite, N-bromo glutarimide, 1,3-dibromo-2,4-imidazolidinedione, 3-bromo-1-chloro-5,5-dimethylhydantoin, 1-bromo-5-ethyl-3,5-dimethyl-2,4-imidazolidinedione, 1,3-dibromo-5-ethyl-5-methylhydantoin, 1,3-dibromo-5-isopropyl-5-methylhydantoin, 3-bromo-5-methyl-5-phenyl-imidazolidine-2,4-dione, dibromo(triphenyl)phosphorane, carbon tetrabromide, bromoform, dibromomethane, hexabromoacetone, lithium bromide, sodium bromide, potassium bromide, cesium bromide, beryllium bromide, magnesium bromide, calcium bromide, aluminum bromide, indium bromide, titanium bromide, ferrous bromide, ferric bromide, tin bromide, and hydrobromic acid.

Alternative solvents may be employed, such as dimethylsulfoxide, N,N-dimethylformamide, N-methylpyrolidine, 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, ethanol, n-propanol, 2-propanol, butanol, tert-butanol, benzene, and nitromethane.

The reaction may take place at temperatures that range from about 0° C. to about 60° C. and at time lengths of about 2 hours to about 5 hours or about 12 minutes to about 24 hours.

Example 8

Alternative Synthesis of Compound (I-a)

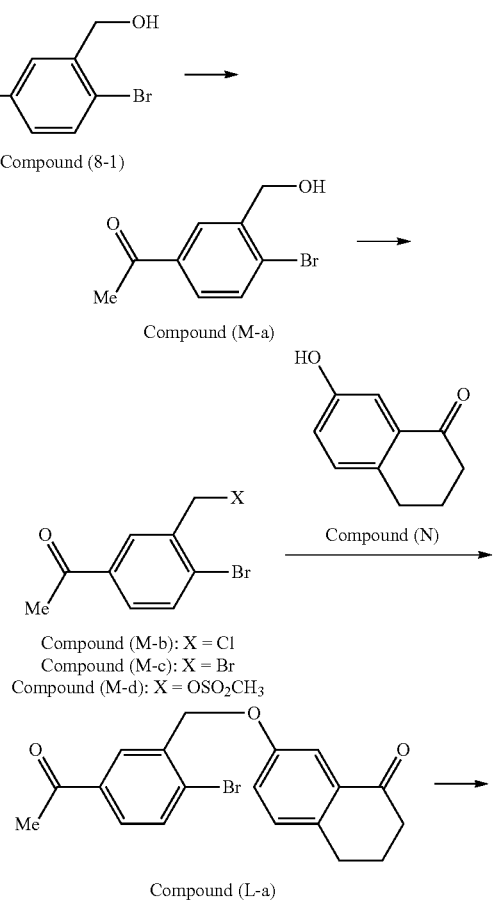

Compound (8-1)

Compound (M-a)

Compound (N)

Compound (M-b): X = Cl
Compound (M-c): X = Br
Compound (M-d): X = OSO$_2$CH$_3$

Compound (L-a)

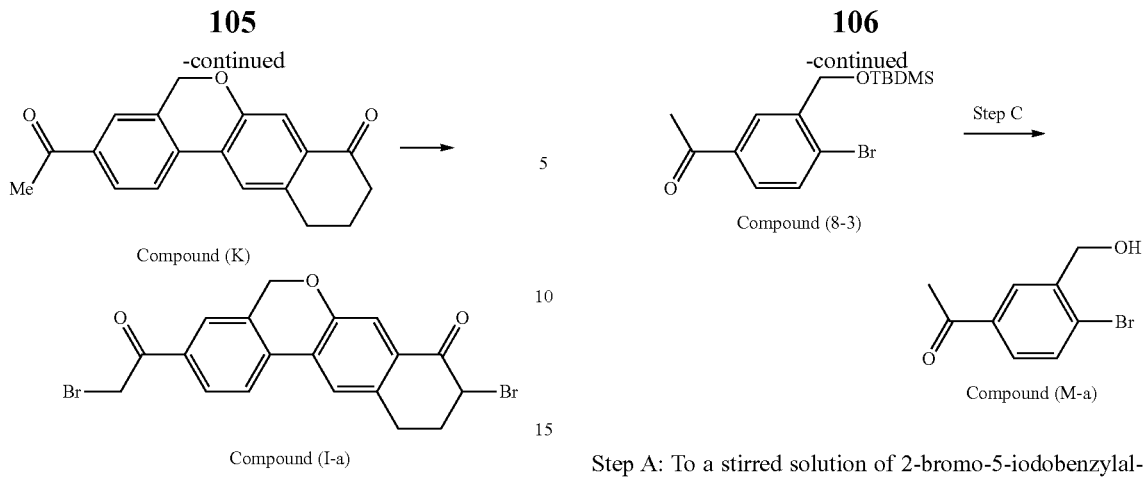

Compound (K)

Compound (I-a)

Preparation of Compound (M-a) from Compound (8-1)

To a stirred solution of 2-bromo-5-iodobenzyl alcohol (5.0 g, 16.0 mmol) (Compound (8-1)) in dry THF (40 mL) was added a 2 M solution of isopropylmagnesium chloride in THF (17.6 mL, 35.2 mmol) while maintaining the internal temperature below about −10° C. A white suspension was formed after 5 min. The mixture was stirred for about 1 h at or below about −10° C. and then was added N-methoxy-N-methylacetamide (3.73 mL, 35.2 mmol) dropwise over a period of about 3 min. The reaction mixture was allowed to warm to about 20° C. over 1 h. The reaction mixture was cooled to about 0° C., quenched with 3N HCl (25 mL), and diluted with tert-butylmethyl ether (50 mL). The resulting biphasic mixture was stirred and the layers separated. The organic layer was washed with 1M HCl (50 mL) followed by water (50 mL) and concentrated under reduced pressure to afford Compound (M-a) as a crude product mixture which was used in next step without further purification. $^1$H NMR (400 MHz, CDCl$_3$) δ 8.07 (s, 1H), 7.72 (d, J=8.4 Hz, 1H), 7.63 (d, J=8.4 Hz, 1H), 4.79 (s, 2H), 2.59 (s, 3H).

Alternative reagents and reaction conditions to those disclosed above may also be employed. For example, alternative metalation reagents, in lieu of isopropylmagnesium chloride, can be magnesium metal, alkyllithium, or lithium metal, and alternative acylating reagents, in lieu of N-methoxy-N-methylacetamide, may be acetonitrile, acetyl chloride or acetic anhydride. Various additives may be employed, such as hexamethylphosphoramide, N,N,N',N'-tetramethylethylenediamine, and chlorotrimethylsilane. Various solvents, such as tetrahydrofuran, 2-methyltetrahydrofuran, or mixtures of toluene and tetrahydrofuran may be employed, and the reaction may proceed at temperatures of about −15° C. to about 20° C.

Alternative Preparation of Compound (M-a) Via Tert-Butyldimethylsilyl Ether Protection

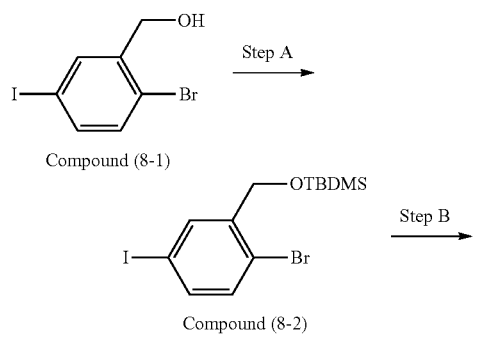

Step A: To a stirred solution of 2-bromo-5-iodobenzylalcohol (10 g, 32 mmol) (Compound (8-1)) in dichloromethane (200 mL) was added imidazole followed by TBDMS-Cl at room temperature. The mixture was stirred at room temperature for about 2 h and partitioned between dichloromethane (additional 100 mL) and water (200 mL). The combined organic layers were dried over anhydrous sodium sulfate, filtered and concentrated under reduced pressure to give (2-bromo-5-iodobenzyloxy)(tert-butyl)dimethylsilane, Compound (8-2), which was used in next step without further purification.

Step B: To a stirred solution of Compound (8-2) (12.5 g, 29.3 mmol) in dry THF (37.5 mL) was added a 2M solution of isopropylmagnesium chloride in THF (16.1 mL, 32.2 mmol) while maintaining the internal temperature below −20° C. The mixture was stirred for about 45 min at or below −20° C. and then was added with N-methoxy-N-methylacetamide (3.73 mL, 35.2 mmol) dropwise over a period of about 3 min. The resulting mixture was allowed to warm to about 20° C. over about 1 h. The reaction mixture was cooled to about 0° C., quenched with saturated NH$_4$Cl (10 mL), diluted with tert-butylmethyl ether (100 mL), and washed with water (2×50 mL). The organic layer was dried over anhydrous sodium sulfate and concentrated under reduced pressure to give 1-(4-bromo-3-((tert-butyldimethylsilyloxy) methyl)phenyl)ethanone, Compound (8-3). The crude product was used in next step without further purification.

Step C: To a stirred solution of Compound (8-3) (11.42 g, 33.3 mmol) in THF (55 L) was added a 2 M solution of HCl in water (33.3 mL) at room temperature and the mixture was stirred for about 3 h. The reaction mixture was partitioned between ethyl acetate and, sequentially, saturated sodium bicarbonate and water. The organic layer was dried over anhydrous sodium sulfate, filtered and concentrated under reduced pressure to give Compound (M-a).

Alternative reagents and reaction conditions to those disclosed above may also be employed. For example, in Step B, alternative metalation reagents, in lieu of isopropylmagnesium chloride, may be magnesium metal, alkyl lithium, or lithium metal, and alternative acylating reagents, in lieu of N-methoxy-N-methylacetamide, may be acetonitrile, acetyl chloride or acetic anhydride. Various additives may be employed, such as hexamethylphosphoramide, N,N,N',N'-tetramethylethylenediamine, and chlorotrimethylsilane. Various solvents, such as tetrahydrofuran or 2-methyltetrahydrofuran, may be employed, and the reaction may proceed at temperatures of about −15° C. to about 20° C. The reaction may proceed at time lengths of about 1 hour to about 5 hours.

In Step A, alternative protecting groups, such as trimethylsilyl, triethylsilyl, tert-butyldiphenylsilyl, tetrahydropyranyl, etc may be used. Depending on the protecting group used in Step A, an appropriate deprotection conditions should be employed in Step C. Strategies for protection/deprotection are well known in the art. See e.g., Protective Groups in Organic Chemistry, Theodora W. Greene, John Wiley & Sons, Inc., New York, 1991. The reactions in Steps A and C can proceed at about 20° C. and at time lengths of about 2 hours to about 3 hours.

Preparation of Compound (M-b), 1-(4-bromo-3-(chloromethyl)phenyl)ethanone

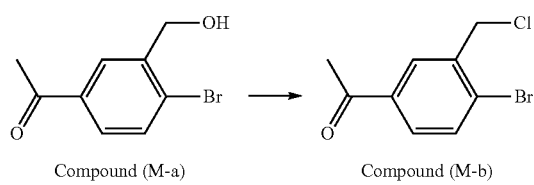

Compound (M-a)   Compound (M-b)

To a stirred solution of 1-(4-bromo-3-(hydroxymethyl)phenyl)ethanone (3.1 g, 13.5 mmol) in dry THF (30 mL) was added triethylamine (2.82 mL, 20.25 mmol) and the mixture was cooled to about 0° C. Methanesulfonyl chloride (1.15 mL, 14.9 mmol) was added to the cold mixture dropwise over a period of about 3 min. The resultant mixture was stirred at about 0° C. for about 30 min and then lithium chloride (2.9 g, 67.5 mmol) was added. The mixture was allowed to warm to room temperature and stirred for about an additional 2 h. The reaction mixture was partitioned between tert-butylmethyl ether (30 mL) and water (2×15 mL). The organic layer was dried over anhydrous sodium sulfate, filtered and concentrated under reduced pressure to a minimum volume. Heptane (15 mL) was added to the residue and the mixture was gently stirred for about 2 h to give a suspension. The solids were collected by filtration, washed with heptane (5 mL) and dried under vacuum to give Compound (M-b). $^1$H NMR (400 MHz, CDCl$_3$) δ 8.05 (s, 1H), 7.75 (d, J=8.4 Hz, 1H), 7.69 (d, J=8.4 Hz, 1H), 4.73 (s, 2H), 2.60 (s, 3H).

Alternative reagents and reaction conditions to those disclosed above may also be employed. For example, alternative reagents in lieu of methanesulfonyl chloride may be methanesulfonic anhydride. Alternative reagents for chlorination may be tosyl chloride/lithium chloride, thionyl chloride, and triphenylphosphine/N-chlorosuccinimide. Residual triethylamine hydrochloride salt generated during mesylation reaction may also be used as chlorinating agent without using lithium chloride. Various solvents may be employed, such as tetrahydrofuran and 2-methyltetrahydrofuran. The reaction may take place at temperatures that range from about 0° C. to about 20° C. and at time lengths of about 5 hours to about 7 hours.

Preparation of Compound (M-c), 1-(4-bromo-3-(bromomethyl)phenyl)ethanone

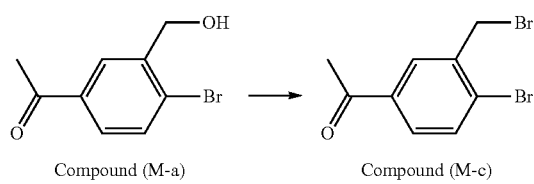

Compound (M-a)   Compound (M-c)

To a stirred solution of 1-(4-bromo-3-(hydroxymethyl)phenyl)ethanone (458 mg, 2 mmol) in dichloromethane (5 mL) was added triethylamine (0.417 mL, 3 mmol) and the mixture was cooled to about 0° C. Methanesulfonyl chloride (0.107 mL, 2.2 mmol) was added to the mixture dropwise and the stirred for about 1 h at about 0° C. The reaction mixture was partitioned between MTBE (25 mL) and water (2×10 mL). The organic layer was dried over anhydrous sodium sulfate, filtered and concentrated under reduced pressure to give the mesylate. To the mesylate was added THF (5 mL) and lithium bromide (695 mg, 8 mmol) and the mixture was stirred at room temperature for about 2 h. The reaction mixture was partitioned between MTBE (25 mL) and water (2×10 mL). The organic layer was dried over anhydrous sodium sulfate, filtered and concentrated under reduced pressure to give Compound (M-c). $^1$H NMR (400 MHz, CDCl$_3$) δ 8.02 (d, J=2.0 Hz, 1H), 7.74-7.68 (m, 2H), 4.63 (s, 2H), 2.60 (s, 3H).

Alternative reagents and reaction conditions to those disclosed above may also be employed. For example, alternative reagents in lieu of methanesulfonyl chloride may be methanesulfonic anhydride. Alternative reagents for bromination may include tosyl chloride/lithium bromide, thionyl bromide, triphenylphosphine/N-bromosuccinimide, phosphorous tribromide, triphenylphosphine/carbon tetrabromide, and hydrobromic acid. Various solvents may be employed, such as tetrahydrofuran and 2-methyltetrahydrofuran. The reaction may take place at temperatures that range from about 0° C. to about 20° C. and at time lengths of about 30 minutes to about 3 hours or about 30 minutes to about 1 hour.

Preparation of Compound (L-a), 7-(5-acetyl-2-bromobenzyloxy)-3,4-dihydronaphthalen-1(2H)-one

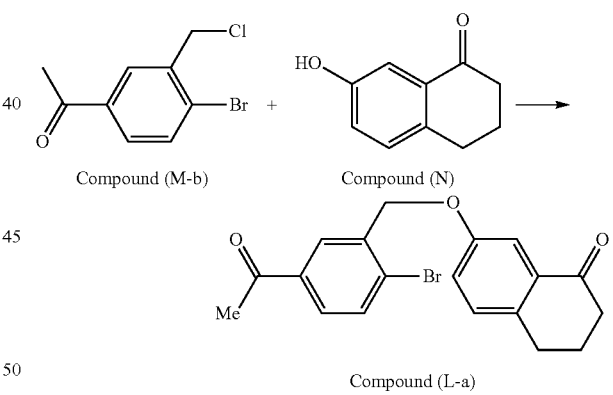

Compound (M-b)   Compound (N)

Compound (L-a)

A mixture of 1-(4-bromo-3-(chloromethyl)phenyl)ethanone (600 mg, 2.42 mmol), 7-hydroxytetralone (393 mg, 2.42 mmol), potassium carbonate (668 mg, 4.84 mmol) and tetrabutylammonium bromide (78 mg, 0.242 mmol) in DMAc (3 mL) was stirred at room temperature for about 20 h. The reaction mixture was partitioned between ethyl acetate (18 mL) and water (2×6 mL). The organic layer was dried over anhydrous sodium sulfate and concentrated to an approximate volume of 5 mL. Product precipitate was filtered, washed with ethyl acetate (2 mL) and dried under vacuum to give Compound (L-a). $^1$H NMR (400 MHz, CDCl$_3$) δ 8.14 (d, J=2.4 Hz, 1H), 7.7 (dd, J=8.4, 2.4 Hz, 1H), 7.70 (d, J=8.4 Hz, 1H), 7.64 (d, J=2.4 Hz, 1H), 7.23-7.16 (m, 2H), 5.17 (s, 2H), 2.92 (t, J=6.4 Hz, 2H), 2.65 (dd, J=13.2, 6.0 Hz, 2H), 2.60 (s, 3H), 2.16-2.10 (m, 2H).

Alternative reagents and reaction conditions to those disclosed above may also be employed. For example, an alternative reagent may be sodium iodide. Various solvents, such as tetrahydrofuran, 2-methyltetrahydrofuran, N,N-dimethylformamide, and acetonitrile, may be employed. The reaction may take place at a temperature of about 20° C. or at temperatures that range from about 20° C. to about 65° C. and may take place at time lengths of about 6 hours to about 20 hours.

Alternative Preparation of Compound (L-a)

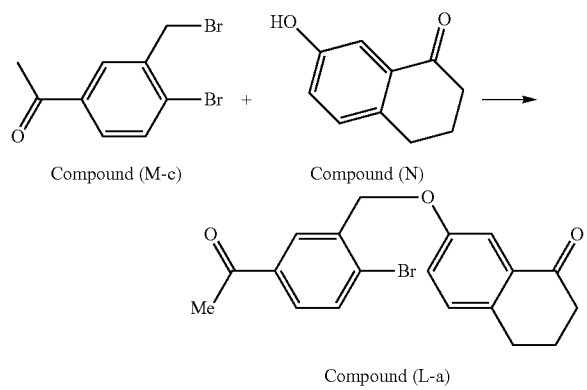

Compound (L-a)

A mixture of 1-(4-bromo-3-(bromomethyl)phenyl)ethanone (500 mg, 1.71 mmol), 7-hydroxytetralone (291 mg, 1.79 mmol), potassium carbonate (472 mg, 3.42 mmol) and acetonitrile (5 mL) was heated at about 70° C. for about 2 h. The mixture was partitioned between MTBE (20 mL) and water (2×10 mL). The organic layer was dried over anhydrous sodium sulfate, filtered and concentrated under reduced pressure to give crude product. Column chromatography of the crude mixture on silica gel using 15-50% ethyl acetate hexanes gradient followed by recrystallization from methanol (3.5 mL) gave Compound (L-a).

Alternative reagents and reaction conditions to those disclosed above may also be employed. For example, an alternative reagent may be sodium iodide. Various solvents, such as tetrahydrofuran, 2-methyltetrahydrofuran, N,N-dimethylformamide, N,N-dimethylacetamide, and acetonitrile, may be employed. The reaction may take place at temperatures that range from about 20° C. to about 70° C.

Preparation of Compound (K), 3-acetyl-10,11-dihydro-5H-dibenzo[c,g]chromen-8(9H)-one

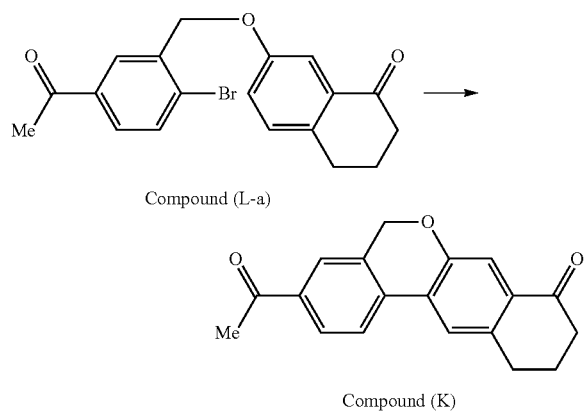

A reaction vessel was charged with 7-(5-acetyl-2-bromobenzyloxy)-3,4-dihydronaphthalen-1(2H)-one (2.5 g, 6.7 mmol) (Compound (L-a)), palladium (II) acetate (150 mg, 0.67 mmol), triphenylphosphine (175.5 mg, 0.67 mmol), pivalic acid (205 mg, 2.01 mmol), potassium carbonate (1.02 g, 7.37 mmol) and DMAc (50 mL). The reaction vessel was evacuated and back filled with nitrogen. The reaction mixture was then heated at about 80° C. under nitrogen atmosphere for about 5 h. After completion of the reaction the mixture was cooled to room temperature and charged with ethyl acetate (50 mL) followed by water (75 mL). The biphasic mixture was stirred at room temperature for about 20 min and filtered through a pad of celite and partitioned. The organic layer was washed with water (25 mL), dried over sodium sulfate, filtered and concentrated under reduced pressure to an approximate final volume of 10 mL. The product precipitated was collected by filtration, washed with ice cold ethyl acetate (5 mL) and dried under vacuum to give Compound (K). $^1$H NMR (400 MHz, DMSO-d6) δ 8.05 (d, J=8.0 Hz, 1H), 7.98 (d, J=8.0 Hz, 1H), 7.96 (s, 1H), 7.90 (s, 1H), 7.36 (s, 1H), 5.21 (s, 2H), 2.95 (t, J=5.6 Hz, 1H), 2.61-2.56 (m, 3H), 2.59 (s, 3H), 2.05-2.02 (m, 2H).

Alternative reagents and reaction conditions to those disclosed above may also be employed. For example, alternative reagents may include tetrabutyl ammonium bromide, Pd(dba)$_2$, P(4-FPh)$_3$, KHCO$_3$, and DMF. Various solvents may be used, such as DMF and acetonitrile. In addition, the reaction may be performed in the absence of triphenylphosphine. The reaction may also take place at temperatures that range from about 20° C. to about 80° C. and at time lengths of about 5 hours to about 7 hours.

Preparation of Compound (I-a)

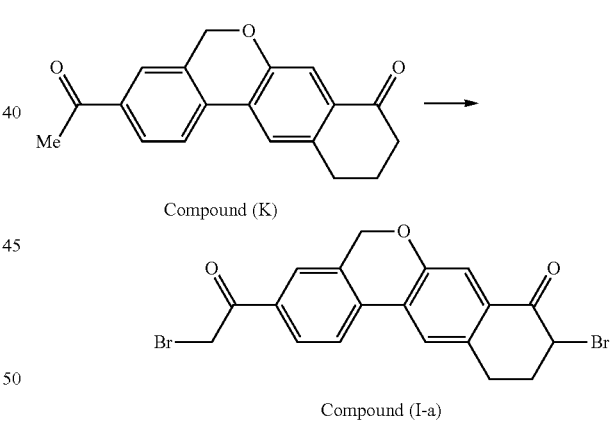

To a stirred solution of Compound (K) (100 mg, 0.342 mmol) in 9:1 dichloromethane/methanol mixture (2 mL) was added pyridinium tribromide (250 mg, 90% technical grade, 0.718 mmol) at room temperature and the mixture was stirred for about 5 h. Product precipitated was filtered, washed with methanol (1 mL) and dried under vacuum to give Compound (I-a). $^1$H NMR (400 MHz, DMSO-d6) δ 8.17-8.01 (m, 3H), 8.01-7.92 (m, 1H), 7.43 (s, 1H), 5.24 (s, 2H), 5.05 (dd, J=8.0 and 4.0 Hz, 1H), 4.94 (s, 2H), 3.15-3.00 (m, 2H), 2.63-2.55 (m, 1H), 2.41-2.35 (m, 1H).

Alternative reagents and reaction conditions may also be employed as described in Example 7. Catalytic HBr can be used for the early initiation of bromination reaction.

Example 9

Synthesis to Compound (I-b)

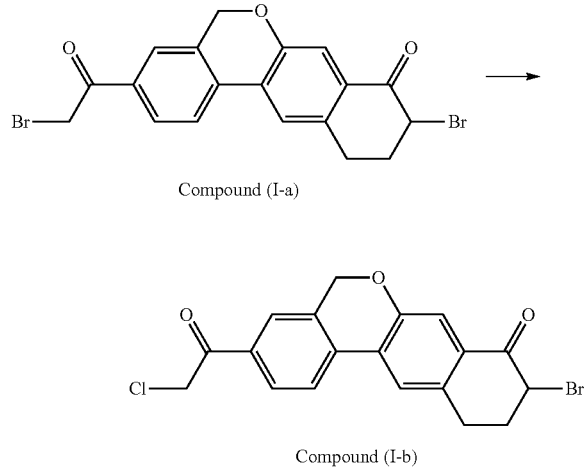

Compound (I-a)

Compound (I-b)

To a reaction vessel was charged Compound (I-a) (10 g) and a solution of tetrahydrofuran and water (10 vol:1 vol; 500 mL). The reactor contents were agitated and sodium chloride (26 g) was added. The internal temperature was adjusted to about 40° C. After complete conversion, the reaction mixture was concentrated under reduced pressure and the residue filtered. The filter cake was washed with water (200 mL) and suspended in dichloromethane (120 mL) at about 30° C. After about 12 h, the mixture was cooled to about 2° C. and filtered. The filter cake was washed with water (300 mL) and dried under reduced pressure at about 40° C. to Compound (I-b). $^1$H NMR (400 MHz, CDCl$_3$) δ 8.00 (m, 1H), 7.86 (m, 1H), 7.80 (s, 1H), 7.72 (s, 1H), 7.68 (s, 1H), 5.20 (s, 2H), 4.74 (m, 1H), 4.70 (s, 2H), 3.40-3.27 (m, 1H), 2.96 (m, 1H), 2.60-2.44 (m, 2H).

Alternative reagents and reaction conditions to those disclosed above may also be employed. For example, alternative reagents, in lieu of sodium chloride, may be lithium chloride, potassium chloride, cesium chloride, beryllium chloride, magnesium chloride, calcium chloride, and barium chloride. various solvents may be employed. non-limiting examples may include dimethylsulfoxide, N,N-dimethylformamide, N-methylpyrolidine, 2-methyltetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, ethanol, n-propanol, 2-propanol, butanol, tert-butanol, benzene, and nitromethane. The reaction may proceed at temperatures ranging from about 0° C. to about 60° C. and for time lengths of about 16 hours or about 30 minutes to about 48 hours.

Example 10

Alternative Synthesis to Compound (I-a)

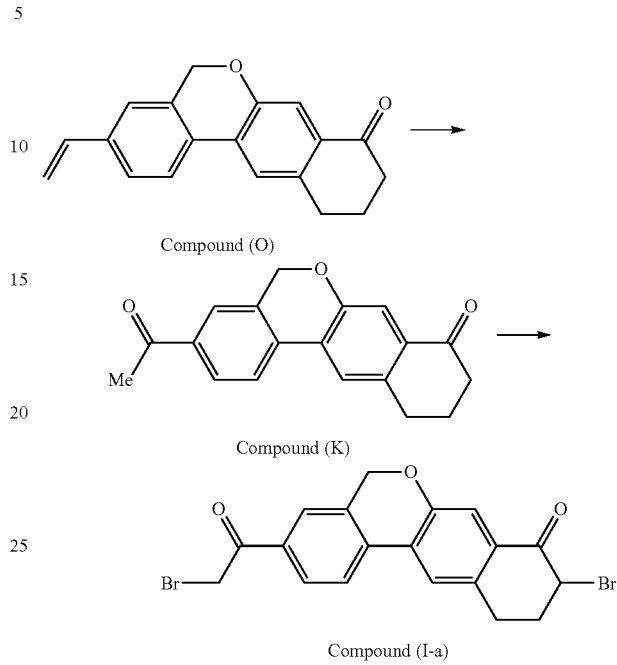

Compound (O)

Compound (K)

Compound (I-a)

Preparation of Compound (K) from Compound (O)

Conversion of Compound (O) to Compound (K) may be carried out in the presence of palladium (such as dichloro [2-(4,5-dihydro-2-oxazolyl)quinoline]palladium(II)) with tert-butylhydroperoxide as an oxidizing agent, silver tetrafluoroborate as an additive, and a mixture of DMF and water as a solvent. The reaction may take place at about 20° C. to about 70° C. and for time lengths of about 30 minutes to about 24 hours.

Alternatively, the conversion of Compound (O) to Compound (K) may be carried out in the presence of palladium catalyst (such as bis(acetonitrile)dichloropalladium(II) or palladium(II)chloride) with oxygen as an oxidizing agent, and a mixture of DMAc and water as a solvent. The reaction may take place at about 20° C. to about 80° C. and for time lengths of about 30 minutes to about 24 hours.

Alternative reagents and reaction conditions to those disclosed above may also be contemplated. Alternative palladium catalysts may be palladium(II) trifluoroacetate, palladium (II) acetylacetonate, allylpalladium(II) chloride dimer, palladium (II) acetate, palladium(II) pivalate, palladium (II) chloride, palladium (II) bromide, tris(dibenzylideneacetone)dipalladium, bis(dibenzylideneacetone)palladium, bis(acetonitrile)dichloropalladium(II), tris (dibenzylideneacetone)dipalladium(0)-chloroform adduct, tetrakis(triphenylphosphine)palladium(0), dichlorobis(tricyclohexylphosphine)palladium(II), bis(triphenylphosphine) palladium(II) dichloride, dichlorobis(tri-o-tolylphosphine) palladium(II), bis(di-tert-butyl(4-dimethylaminophenyl) phosphine)dichloropalladium(II), [1,1'-bis (diphenylphosphino)ferrocene]dichloropalladium(II), [1,1'-bis(diphenylphosphino)ferrocene]dichloropalladium(II) complex with dichloromethane, [1,1'-bis(di-tert-butylphosphino)ferrocene]dichloropalladium(II), tetrakis(acetonitrile) palladium(II) tetrafluoroborate, copper(I) chloride, copper (II) chloride, copper(I) bromide, copper(II) bromide, copper (I) iodide, copper(II) iodide, copper(I) triflate, copper(II) triflate, copper(I) oxide, copper(II) oxide, copper(I) tetrafluoroborate, copper(II) tetrafluoroborate, copper(I) hexafluoroantimonate, and copper(II) hexafluoroantimonate.

Various ligands may be employed, including but not limited to (S)-2-(4,5-dihydro-4-isopropyl-2-oxazolyl)quinoline, 2-(4,4-dimethyl-4,5-dihydro-2-oxazolyl)quinoline, 1,3-Bis-(2,6-diisopropylphenyl)imidazolinium chloride, 1,3-bis(2,4,6-trimethylphenyl)imidazolinium chloride, 1,3-diisopropylimidazolium tetrafluoroborate, 1,3-bis(1-adamantyl)imidazolium tetrafluoroborate, 1,3-bis(2,6-diisopropylphenyl)imidazolium chloride, sparteine, ethylenediamine, tetramethylethylenediamine, and Tröger's base.

Alternative oxidizing agents may include oxygen, hydrogenperoxide, urea hydrogen peroxide, palladium(II) reagents, copper(I) iodide, copper(II) iodide, copper(I) triflate, copper(II) triflate, copper(I) oxide, copper(II) oxide, copper(I) tetrafluoroborate, copper(II) tetrafluoroborate, copper(I) hexafluoroantimonate, copper(II) hexafluoroantimonate, diacetoxy iodobenzene, di(trifluoxoacetoxy) iodobenzene, dichloro iodobenzene, potassium persulfate, sodium perborate, sodium bromate, sodium iodate, sodium periodate, urea hydrogen peroxide, tert-butylhydroperoxide, N-methylmorpholine-N-oxide, trimethylammonium-N-oxide, sodium dichloroisocyanuric acid, iodosobenzene, N-bromo succinimide, N-bromoacetamide, N-bromophthalimide, sodium bromite, sodium hypobromite, m-chloroperbenzoic acid, 2-iodoxybenzoic acid, ruthenium trichloride, rhodium(I) tris-(triphenylphosphine) chloride, palladium(II) acetate, titanium tetraisopropoxide, ferric bromide, copper (I) chloride, copper(II) chloride, copper(I) bromide, copper (II) bromide, tetrapropylammonium perruthenate, N-chloro succinimide, 1,1,1-triacetoxy-1,1-dihydro-1,2-benziodoxol-3(1H)-one, trimethyl aluminium, aluminum triisopropoxide, dimethylsulfoxide, potassium peroxymonosulfate, cericammonium nitrate, oxygen, trichloroisicyanuric acid, cromine, iodine, chlorine, bromine, bromine monochloride, 5,5-dimethyl-1,3-dibromohydantoin, pyridinium tribromide, 2,4,4,6-tetrabromo-2,5-cyclohexadienone, dibromoisocyanuric Acid, tribromoisocyanuric Acid, N-bromoisocyanuric acid monosodium salt, N-bromo phthalimide, N-bromo acetamide, N,N'-dibromo-4-methylbenzenesulphonamide, sodium bromate, lithium bromate, potassium bromate, tetra-n-butylammonium tribromide, trimethylphenylammonium tribromide, trimethylammonium tribromide, triethylammonium tribromide, bromine on polymer support, 4-(dimethylamino)pyridine tribromide, pyridinium tribromide polymer bound, bromotrichloromethane, sodium hypobromite, lithium hypobromite, potassium hypobromite, beryllium hypobromite, magnesium hypobromite, calcium hypobromite, N,N-dibromobenzenesulfonamide, sodium bromite, lithium bromite, potassium bromite, N-bromo glutarimide, 1,3-dibromo-2,4-imidazolidinedione, 3-bromo-1-chloro-5,5-dimethylhydantoin, 1-bromo-5-ethyl-3,5-dimethyl-2,4-imidazolidinedione, 1,3-dibromo-5-ethyl-5-methylhydantoin, 1,3-dibromo-5-isopropyl-5-methylhydantoin, 3-bromo-5-methyl-5-phenyl-imidazolidine-2,4-dione, and dibromo(triphenyl)phosphorane.

Alternative additives may be employed. Non-limiting examples may be silver nitrate, silver hexafluoroantimonate, copper(I) triflate, copper(II) triflate, copper(I) oxide, copper (II) oxide, copper(I) tetrafluoroborate, copper(II) tetrafluoroborate, copper(I) hexafluoroantimonate, and copper(II) hexafluoroantimonate.

The reaction can take place in various solvents, such as dimethylsulfoxide, N,N-dimethylformamide, N-methylpyrolidine, 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, methanol, ethanol, n-propanol, 2-propanol, butanol, tert-butanol, benzene, nitromethane, and water.

The reaction may proceed at temperatures ranging from about 0° C. to 100° C. and at time lengths of about 30 minutes to about 48 hours.

Preparation of Compound (I-a) from Compound (K)

A reaction vessel at ambient temperature was charged with 3-acetyl-10,11-dihydro-5H-dibenzo[c,g]chromen-8 (9H)-one (100 mg), 9:1 $CH_2Cl_2$/MeOH (3.4 mL) and pyridinium tribromide (246 mg). The solution was heated to about 35° C. After about 30 minutes, the reaction was judged complete. The mixture was cooled to about 23° C., diluted with EtOAc (50 mL) and sequentially washed with saturated aqueous $Na_2S_2O_3$ (20 mL), 2% aqueous $NaHCO_3$ (20 mL), water (20 mL), and brine (10 mL). The organic phase was dried over $MgSO_4$, filtered and concentrated under reduced pressure to afford 9-bromo-3-(2-bromoacetyl)-10,11-dihydro-5H-dibenzo[c,g]chromen-8(9H)-one (Compound (I-a)). $^1H$ NMR (400 MHz, $CDCl_3$) δ 8.03-8.01 (m, 1H), 7.85 (d, J=8.2 Hz, 1H), 7.82 (s, 1H), 7.71 (s, 1H), 7.67 (s, 1H), 5.19 (s, 2H), 4.74 (dd, J=4.1, 4.1 Hz, 1H), 4.45 (s, 2H), 3.37-3.29 (m, 1H), 2.99-2.92 (m, 1H), 2.59-2.46 (m, 2H).

Alternative reagents and reaction conditions to those disclosed above may also be employed. For example, alternative starting material may be 3-(2-bromoacetyl)-10,11-dihydro-5H-dibenzo[c,g]chromen-8(9H)-one or 3-acetyl-9-bromo-10,11-dihydro-5H-dibenzo[c,g]chromen-8(9H)-one.

Various brominating agents may be used. Non-limiting examples can include bromine, bromine monochloride, N-bromosuccinimide, 5,5-dimethyl-1,3-dibromohydantoin, 2,4,4,6-tetrabromo-2,5-cyclohexadienone, dibromoisocyanuric acid, tribromoisocyanuric acid, n-bromoisocyanuric acid monosodium salt, N-bromo phthalimide, N-bromo acetamide, N,N'-dibromo-4-methylbenzenesulphonamide, sodium bromate, lithium bromate, potassium bromate, tetra-N-butylammonium tribromide, trimethylphenylammonium tribromide, trimethylammonium tribromide, triethylammonium tribromide, bromine on polymer support, 4-(dimethylamino)pyridine tribromide, pyridinium tribromide polymer bound, bromotrichloromethane, sodium hypobromite, lithium hypobromite, potassium hypobromite, beryllium hypobromite, magnesium hypobromite, calcium hypobromite, N,N-dibromobenzenesulfonamide, sodium bromite, lithium bromite, potassium bromite, n-bromo glutarimide, 1,3-dibromo-2,4-imidazolidinedione, 3-bromo-1-chloro-5,5-dimethylhydantoin, 1-bromo-5-ethyl-3,5-dimethyl-2,4-imidazolidinedione, 1,3-dibromo-5-ethyl-5-methylhydantoin, 1,3-dibromo-5-isopropyl-5-methylhydantoin, 3-bromo-5-methyl-5-phenyl-imidazolidine-2,4-dione, dibromo(triphenyl)phosphorane, carbon tetrabromide, bromoform, dibromomethane, hexabromoacetone, lithium bromide, sodium bromide, potassium bromide, cesium bromide, beryllium bromide, magnesium bromide, calcium bromide, aluminum bromide, indium bromide, titanium bromide, ferrous bromide, ferric bromide, tin bromide, and hydrobromic acid.

Various solvents may be employed, such as dimethylsulfoxide, N,N-dimethylformamide, N-methylpyrolidine, 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, ethanol, n-propanol, 2-propanol, butanol, tert-butanol, benzene, and nitromethane.

The reaction may proceed at temperatures ranging from about 0° C. to 60° C. and at time lengths of about 12 minutes to about 24 hours.

Example 11

Alternative Synthesis to Compound (I-a)

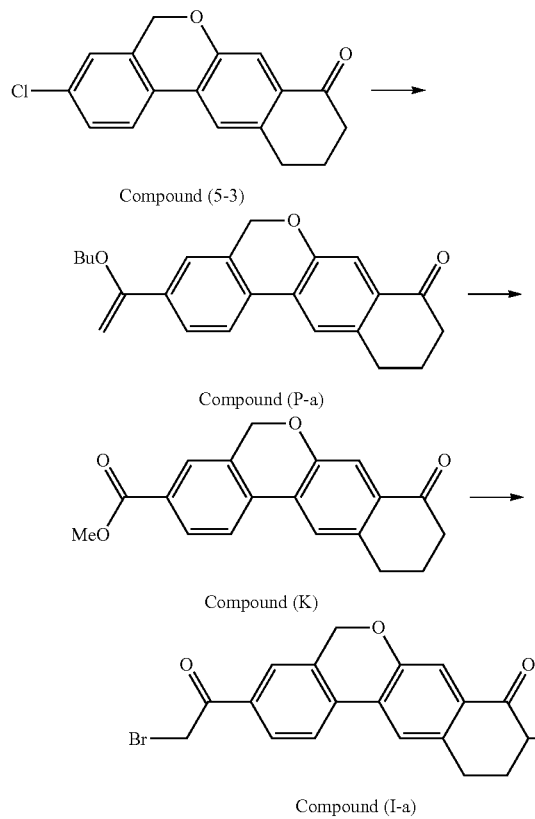

Compound (5-3)

Compound (P-a)

Compound (K)

Compound (I-a)

Preparation of Compound (P-a) from Compound (5-3)

To synthesize Compound (P-a) from Compound (5-3), Compound (5-3) can be reacted in the presence of a catalyst, such as Pd(OAc)$_2$, a ligand such as 1,3-diisopropylphosphinopropane, and a base such as triethylamine. The solvent for the reaction may be N,N-dimethylacetamide. The reaction temperature may be from about 20° C. to about 80° C., and the reaction time may range from about 20 minutes to about 2 hours. The reaction may be conducted in the presence of a stabilizer such as 3,5-di-tert-butyl-4-hydroxytoluene.

Alternative reagents and reaction conditions to those disclosed above may also be contemplated. For example, alternative catalysts may include palladium(II) trifluoroacetate, palladium(II) acetylacetonate, allylpalladium(II) chloride dimer, palladium(II) acetate, palladium(II) pivalate, palladium(II) chloride, palladium(II) bromide, tris(dibenzylideneacetone)dipalladium, bis(dibenzylideneacetone) palladium, bis(acetonitrile)dichloropalladium(II), tris (dibenzylideneacetone)dipalladium(0)-chloroform adduct, tetrakis(triphenylphosphine)palladium(0), dichlorobis(tricyclohexylphosphine)palladium(II), bis(triphenylphosphine) palladium(II) dichloride, dichlorobis(tri-o-tolylphosphine) palladium(II), bis(di-tert-butyl(4-dimethylaminophenyl) phosphine)dichloropalladium(II), [1,1'-bis(diphenylphosphino)ferrocene]dichloropalladium(II), [1,1'-bis(diphenylphosphino)ferrocene]dichloropalladium(II) complex with dichloromethane, [1,1'-bis(di-tert-butylphosphino)ferrocene]dichloropalladium(II), tetrakis(acetonitrile) palladium(II) tetrafluoroborate, (SPhos) palladium(II) phenethylamine chloride, (XPhos) palladium(II) phenethylamine chloride, (RuPhos) palladium(II) phenethylamine chloride, (t-BuXPhos) palladium(II) phenethylamine chloride, and (BrettPhos) palladium(II) phenethylamine chloride.

Alternative ligands, in lieu of 1,3-diisopropylphosphinopropane, may be any ligands known in the art. Non-limiting examples may be triphenylphosphine, tri-(2-furyl)phosphine, Tri-tert-butylphosphine, tri-tert-butylphosphine hydro tetrafluoroborate, methyl-di-tert-butylphosphine, methyl-di-tert-butylphosphine hydro tetrafluoroborate, 4,5-bis(diphenylphosphino)-9,9-dimethylxanthene, tri(p-tolyl) phosphine, 4-(methoxy)phenyldiphenylphosphine, 4-(dimethylamino)phenyldiphenylphosphine, tri(4-fluorophenyl) phosphine, tri(4-trifluoromethylphenyl)phosphine, tri(4-methoxyphenyl)phosphine, tri(3-methylphenyl)phosphine, tri(2-methylphenyl)phosphine, tri(cyclohexyl)phosphine, tri (2-furanyl)phosphine, 1,1'-bis(diphenylphosphino) ferrocene, 1,1'-bis(dicyclohexylphosphino) ferrocene, 1,1'-bis (ditertbutylphosphino) ferrocene, 1,3-bis-(2,6-diisopropylphenyl)imidazolinium chloride, 1,3-bis(2,4,6-trimethylphenyl)imidazolinium chloride, 1,3-diisopropylimidazolium tetrafluoroborate, 1,3-bis(1-adamantyl)imidazolium tetrafluoroborate, 2-(dicyclohexylphosphino)biphenyl, 2-dicyclohexylphosphino-2'-(N,N-dimethylamino)biphenyl, 2-dicyclohexylphosphino-2',4',6'-triisopropylbiphenyl, 2-dicyclohexylphosphino-2'-methylbiphenyl, 2-dicyclohexylphosphino-2', 6'-diisopropoxybiphenyl, 2-(dicyclohexylphosphino)3,6-dimethoxy-2',4',6'-triisopropyl-1,1'-biphenyl, sodium 2'-dicyclohexylphosphino-2,6-dimethoxy-1,1'-biphenyl-3-sulfonate hydrate, 2-diphenylphosphino-2'-(N,N-dimethylamino)biphenyl, 2-di-tert-butylphosphino-2',4',6'-triisopropylbiphenyl, (2-biphenyl)di-tert-butylphosphine, 2-di-tert-butylphosphino-3,4,5,6-tetramethyl-2',4',6'-triisopropyl-1, 1'-biphenyl, 2-di-tert-butylphosphino-2'-methylbiphenyl, 2-(di-tert-butylphosphino)-2',4',6'-triisopropyl-3,6-dimethoxy-1,1'-biphenyl, 2-di-tert-butylphosphino-2'-(N,N-dimethylamino)biphenyl, 2-{bis[3,5-bis(trifluoromethyl)phenyl]phosphino}-3,6-dimethoxy-2',4',6'-triisopropyl-1,1'-biphenyl, bis(diphenylphosphino)methane, 1,2-bis (diphenylphosphino)ethane, 1,3-bis(diphenylphosphino) propane, 1,4-bis(diphenylphosphino)butane, 1,5-bis (diphenylphosphino)pentane, 1,6-bis(diphenylphosphino) hexane, bis(dicyclohexylphosphino)methane, 1,2-bis (dicyclohexylphosphino)ethane, 1,3-bis(dicyclohexylphosphino)propane, 1,3-bis(dicyclohexylphosphino)propane, 1,5-bis(dicyclohexylphosphino)pentane, 1,6-bis(dicyclohexylphosphino)hexane, bis(diisopropylphosphino) methane, 1,2-bis(diisopropylphosphino)ethane, 1,3-bis (diisopropylphosphino)propane, 1,3-bis(dicyclohexylphosphino)propane, 1,5-bis(diisopropylphosphino)pentane, 1,6-bis(diisopropylphosphino)hexane, bis(di-tert-butylphosphino)methane, 1,2-bis(di-tert-butylphosphino)ethane, 1,3-bis(di-tert-butylphosphino)propane, 1,3-bis(dicyclohexylphosphino)propane, 1,5-bis(di-tert-butylphosphino)pentane, 1,6-bis(di-tert-butylphosphino)hexane, bis(dicyclopentylphosphino)methane, 1,2-bis(dicyclopentylphosphino)ethane, 1,3-bis(dicyclopentylphosphino)propane, 1,3-bis(dicyclohexylphosphino)propane, 1,5-bis(dicyclopentylphosphino)pentane, 1,6-bis(dicyclopentylphosphino)hexane, and the like.

Alternative alkenes may be 1-(vinyloxy)methane, 1-(vinyloxy)ethane, 1-(vinyloxy)propane, 1-(vinyloxy)-2-propane, tert-butyl vinyl ether, ethylene glycol vinyl ether, isobutyl vinyl ether, vinyl acetate, tri(ethylene glycol) divinyl ether, 1,4-butanediol vinyl ether, di(ethylene glycol) vinyl ether, di(ethylene glycol) divinyl ether, isooctyl vinyl ether, 2-ethylhexyl vinyl ether, N,N-dimethyl-2-(vinyloxy) ethanamine, vinyl propionate, vinyl pivalate, cyclohexyl vinyl ether, 2,2,2-trifluoroethyl vinyl ether, vinyl butyrate, and vinyl trifluoroacetate.

Various bases may be employed. Non-limiting examples may include lithium carbonate, sodium carbonate, cesium carbonate, beryllium carbonate, magnesium carbonate, calcium carbonate, strontium carbonate, barium carbonate, lithium hydroxide, sodium hydroxide, potassium hydroxide, cesium hydroxide, beryllium hydroxide, magnesium hydroxide, Calcium hydroxide, strontium hydroxide, barium hydroxide, lithium bicarbonate, sodium bicarbonate, potassium bicarbonate, cesium bicarbonate, beryllium bicarbonate, magnesium bicarbonate, calcium bicarbonate, strontium bicarbonate, barium bicarbonate, lithium hydride, sodium hydride, potassium hydride, magnesium hydride, calcium hydride, lithium tert-butoxide, sodium tert-butoxide, potassium tert-butoxide, cesium tert-butoxide, beryllium tert-butoxide, magnesium tert-butoxide, calcium tert-butoxide, strontium tert-butoxide, barium tert-butoxide, aluminum tert-butoxide, titanium tert-butoxide, 2,2,6,6-tetramethylpiperidine, 2,6-ditertbutylpyridine, 4-methyl-2,6-ditertbutylpyridine, trilithium phosphate, trisodium phosphate, tripotassium phosphate, tricesium phosphate, beryllium phosphate, magnesium phosphate, calcium phosphate, strontium phosphate, dilithium hydrogenphosphate, disodium hydorgenphosphate, dipotassium hydrogenphosphate, dicesium hydrogenphosphate, lithium dihydrogenphosphate, sodium dihydrogenphosphate, potassium dihydrogenphosphate, cesium dihydrogenphosphate, lithium tert-butylcarboxylate, sodium tert-butylcarboxylate, potassium tert-butylcarboxylate, cesium tert-butylcarboxylate, lithium acetate, sodium acetate, potassium acetate, cesium acetate, lithium propanoate, sodium propanoate, potassium propanoate, cesium propanoate, lithium isobutyrate, sodium isobutyrate, potassium isobutyrate, cesium isobutyrate, lithium adamantylcarboxylate, sodium adamantylcarboxylate, potassium adamantylcarboxylate, cesium adamantylcarboxylate, lithium trifluoroaceate, sodium trifluoroaceate, potassium trifluoroaceate, cesium trifluoroaceate, triethylamine, trimethylamine, tripropylamine, tributylamine, diisopropylethylamine, dicyclohexylmethylamine, lithium methoxide, lithium ethoxide, lithium isopropoxide, lithium propoxide, lithium butoxide, lithium phenoxide, sodium methoxide, sodium ethoxide, sodium isopropoxide, sodium butoxide, sodium phenoxide, potassium methoxide, potassium ethoxide, potassium isopropoxide, potassium propoxide, potassium butoxide, potassium phenoxide, cesium methoxide, cesium ethoxide, cesium isopropoxide, cesium propoxide, cesium butoxide, and cesium phenoxide.

Various solvents may be employed, such as N,N-dimethylformamide, N-methylpyrolidine, 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, dimethylsulfoxide, methanol, ethanol, n-propanol, 2-propanol, butanol, tert-butanol, benzene, and nitromethane.

The reaction temperature may range from about 20° C. to about 100° C., and the reaction time may range from about 30 minutes to about 48 hours.

Preparation of Compound (K) from Compound (P-a)

To synthesize Compound (K) from Compound (P-a), Compound (P-a) may be reacted with trifluoroacetic acid in a solvent of a mixture of dichloromethane and water. The reaction may take place at about 5° C. to about 40° C., and the reaction time may range from about 30 minutes to about 12 hours.

Alternative reagents and reaction conditions to those disclosed above may also be employed. For example, alternative acids may be employed. Non-limiting examples may include formic acid, acetic acid, propanoic acid, butanoic acid, pivalic acid, pentanoic acid, benzoic acid, hydrochloric acid, hydrobromic acid, hydroiodic acid, hydrofluoric acid, sulfuric acid, sulfurous acid, phosphoric acid, citric acid, nitric acid, oxalic acid, and the like. various solvents may be employed, including but not limited to N,N-dimethylformamide, N-methylpyrolidine, 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane dimethylsulfoxide, methanol, ethanol, n-propanol, 2-propanol, butanol, tert-butanol, benzene, nitromethane, and water.

The reaction temperature may range from about 0° C. to about 100° C., and the reaction time may range from about 30 minutes to about 48 hours.

Preparation of Compound (I-a) from Compound (K)

Compound (I-a) may be synthesized from Compound (K) as described in Examples 7 and 8.

Example 12

Alternative Synthesis to Compound (I-a)

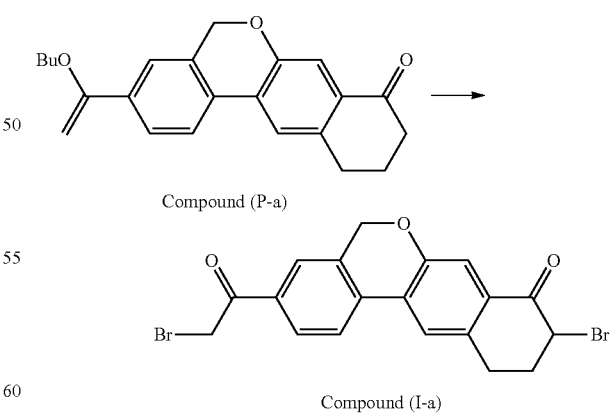

Compound (P-a)

Compound (I-a)

Preparation of Compound (I-a) from Compound (P-a)

Compound (I-a) may be synthesized from Compound (P-a) in the presence of a brominating agent, such as pyridinium tribromide, and in a solvent, such as a mixture of dichloromethane and methanol. The reaction may take place from about 0° C. to about 40° C., and the reaction time may be from about 20 minutes to about 2 hours.

Alternative reagents and reaction conditions to those disclosed above may also be employed. For example, alternative starting material may be Compound (6) or 3-acetyl-9-bromo-10,11-dihydro-5H-dibenzo[c,g]chromen-8(9H)-one.

Various brominating agents may be employed. Non-limiting examples can include bromine, bromine monochloride, N-bromosuccinimide, 5,5-dimethyl-1,3-dibromohydantoin, 2,4,4,6-tetrabromo-2,5-cyclohexadienone, dibromoisocyanuric acid, tribromoisocyanuric acid, N-bromoisocyanuric acid monosodium salt, N-bromo phthalimide, N-bromo acetamide, N,N-dibromo-4-methylbenzenesulfonamide, sodium bromate, lithium bromate, potassium bromate, tetra-n-butylammonium tribromide, trimethylphenylammonium tribromide, trimethylammonium tribromide, triethylammonium tribromide, bromine on polymer support, 4-(dimethylamino)pyridine tribromide, pyridinium tribromide polymer bound, bromotrichloromethane, sodium hypobromite, lithium hypobromite, potassium hypobromite, beryllium hypobromite, magnesium hypobromite, calcium hypobromite, N,N-dibromobenzenesulfonamide, sodium bromite, lithium bromite, potassium bromite, N-bromo glutarimide, 1,3-dibromo-2,4-imidazolidinedione, 3-bromo-1-chloro-5,5-dimethylhydantoin, 1-bromo-5-ethyl-3,5-dimethyl-2,4-imidazolidinedione, 1,3-dibromo-5-ethyl-5-methylhydantoin, 1,3-dibromo-5-isopropyl-5-methylhydantoin, 3-bromo-5-methyl-5-phenyl-imidazolidine-2,4-dione, dibromo(triphenyl)phosphorane, carbon tetrabromide, bromoform, dibromomethane, hexabromoacetone, lithium bromide, sodium bromide, potassium bromide, cesium bromide, beryllium bromide, magnesium bromide, calcium bromide, aluminum bromide, indium bromide, titanium bromide, ferrous bromide, ferric bromide, tin bromide, and hydrobromic acid.

Alternative solvents may be dimethylsulfoxide, N,N-dimethylformamide, N-methylpyrolidine, 2-methyltetrahydrofuran, tetrahydrofuran, isopropyl acetate, ethyl acetate, tert-butyl methyl ether, cyclopentyl methyl ether, diethylether, diisopropylether, acetone, methylethyl ketone, methylisobutylketone, diisopropyl ether, 1,4-dioxane, 1,2-dimethoxyethane, chloroform, acetonitrile, toluene, dichloromethane, 1,2-dichloroethane, ethanol, n-propanol, 2-propanol, butanol, tert-butanol, benzene, and nitromethane.

The reaction temperature may range from about 0° C. to about 60° C., and the reaction time may range from about 12 minutes to about 24 hours.

Example 13

Synthesis of Compound (A)

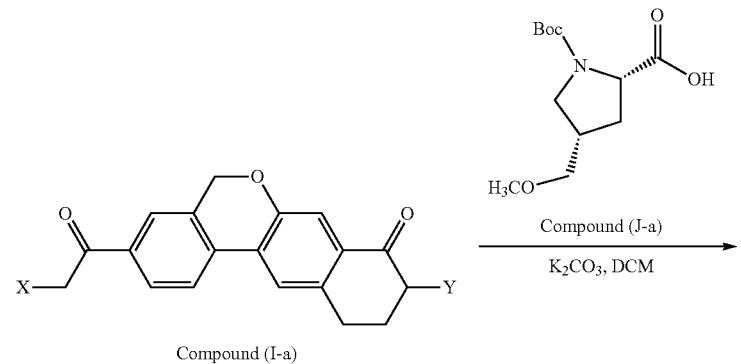

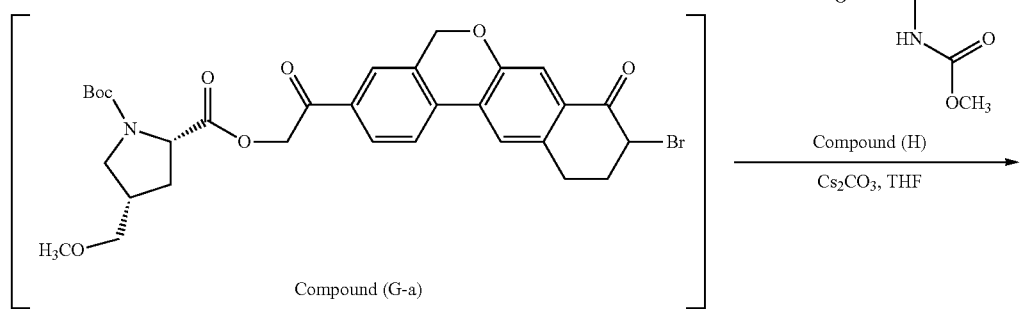

121 122
-continued
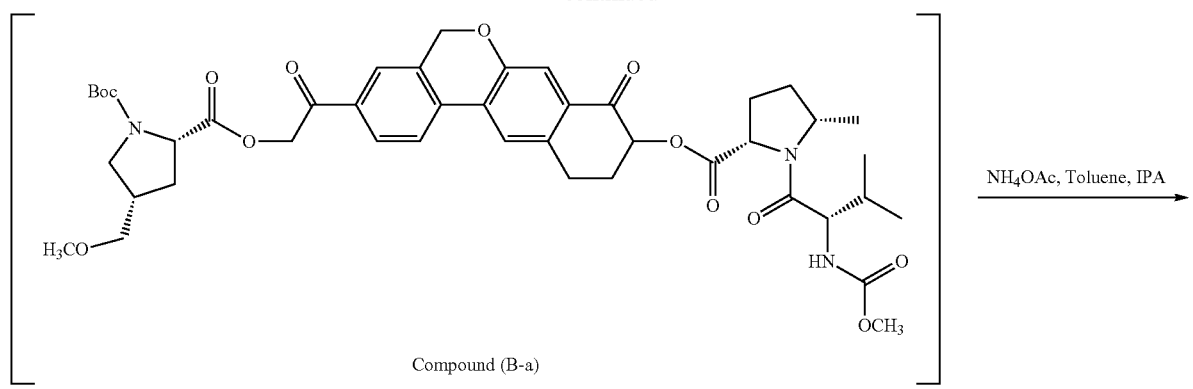
Compound (B-a) →NH4OAc, Toluene, IPA
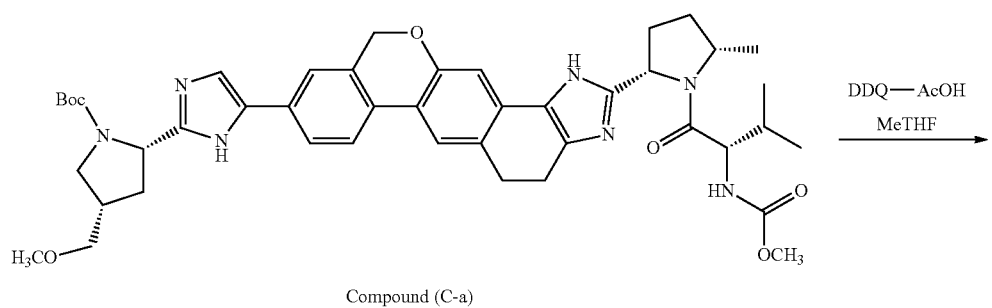
Compound (C-a) →DDQ—AcOH, MeTHF
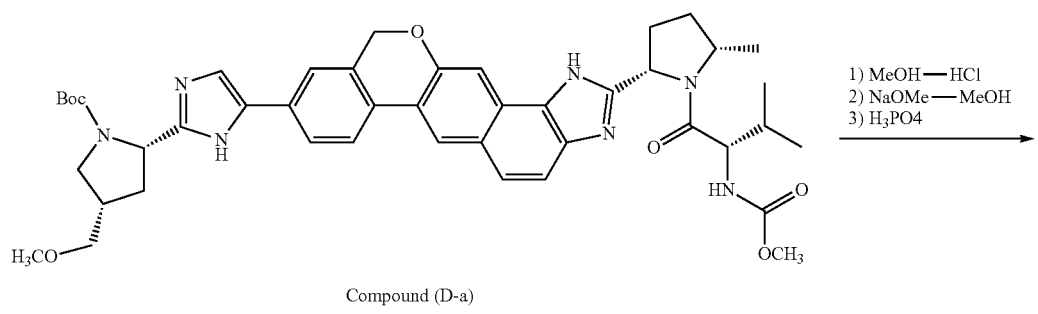
Compound (D-a) →1) MeOH—HCl 2) NaOMe—MeOH 3) H3PO4
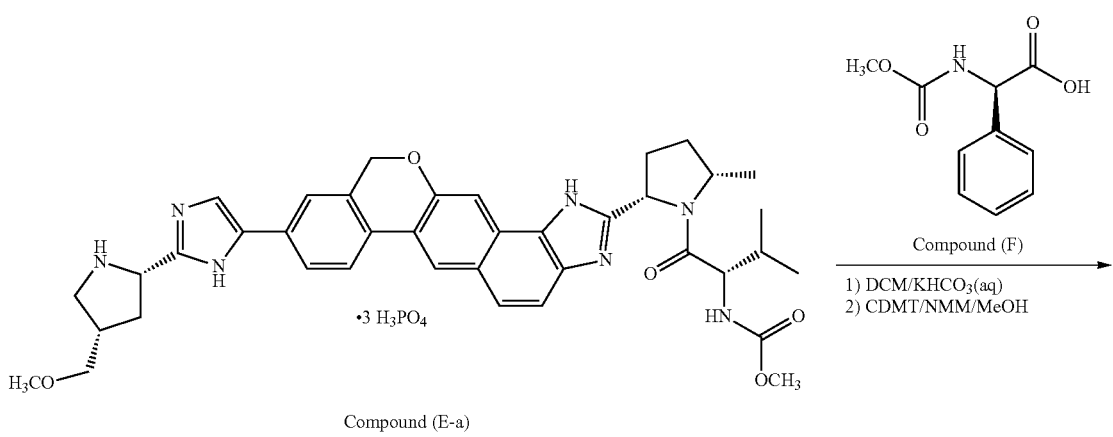
Compound (E-a) · 3 H3PO4
Compound (F) →1) DCM/KHCO3(aq) 2) CDMT/NMM/MeOH

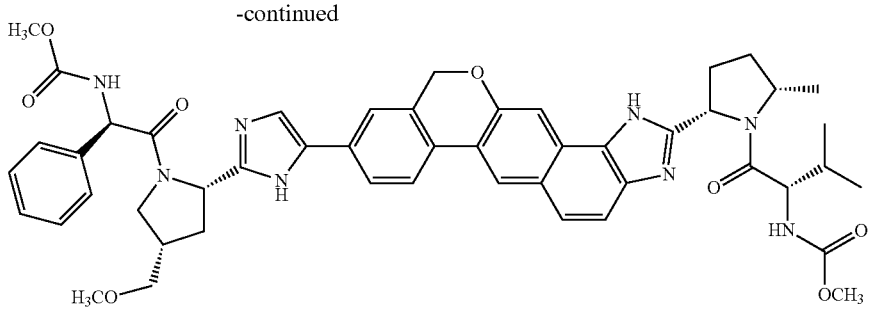

Compound (A)

X, Y = Br

1st Alkylation: Conversion of Compound (I-a) to Compound (G-a)

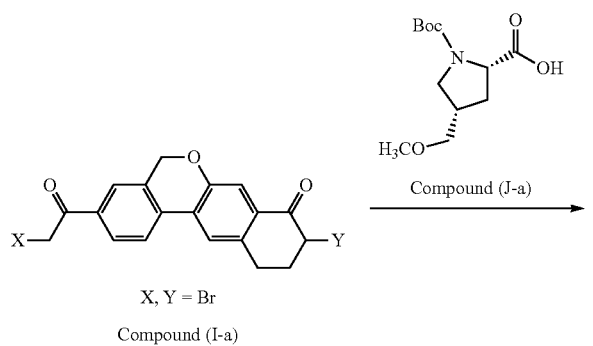

Compound (I-a)

X, Y = Br

Compound (J-a)

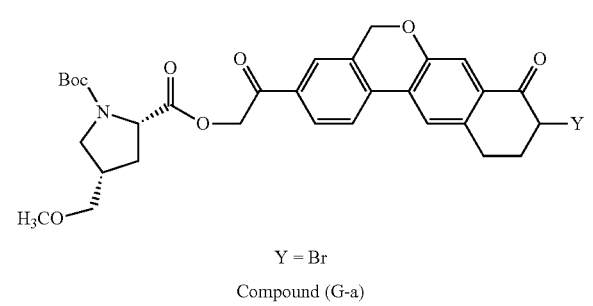

Y = Br

Compound (G-a)

Compound (I-a) (45 g, 1.0 equiv.), Compound (J-a) (26.7 g, 1.03 equiv.) and potassium carbonate (20.7 g, 1.5 equiv.) in dichloromethane (450 mL) were stirred at about 20° C. for approximately 3-4 hours. After the completion of the reaction, water (450 mL) was charged into the reactor and the mixture was stirred. Layers were separated, and the aqueous layer was extracted with dichloromethane (200 mL). The combined organic layers were washed with 2 wt % $NaH_2PO_4$/10 wt % NaCl solution (450 mL). The organic layer was then concentrated and the solvent was swapped from dichloromethane into tetrahydrofuran. A purified sample of Compound (G-a) has the following spectrum: $^1$H NMR (400 MHz, $CDCl_3$) δ 7.90-7.94 (m, 1H), 7.81-7.85 (m, 1H), 7.72 (s, 1H), 7.69 (s, 1H), 7.66 (s, 1H), 5.19-5.56 (2dd, 2H), 5.17 (s, 2H), 4.73 (t, 1H), 4.39-4.48 (m, 1H), 3.70-3.77 (m, 1H), 3.37-3.45 (m, 2H), 3.33-3.35 (d, 3H), 3.28-3.32 (m, 1H), 3.20-3.25 (dd, 1H), 2.92-2.96 (dt, 1H), 2.44-2.59 (m, 4H), 1.97-2.09 (m, 1H), 1.44 (d, 9H).

Alternative reagents and reaction conditions to those disclosed above may also be employed. For example, alternative starting material may be Compound (I) where X may be —Cl, —Br, —OTs, —$OSO_2Ph$, —$OSO_2Me$, —$OSO_2CF_3$, —$OSO_2R$, and —$OP(O)(OR)_2$ and Y may be —Cl, —Br, —OTs, —$OSO_2Ph$, —$OSO_2Me$, —$OSO_2CF_3$, —$OSO_2R$, and —$OP(O)(OR)_2$. R may be alkyl, haloalkyl, or an optionally substituted aryl.

Various bases may also be employed, such as phosphate salts (including but not limited to $KH_2PO_4$, $K_3PO_4$, $Na_2HPO_4$, and $Na_3PO_4$) and carbonate salts (including but not limited to $Na_2CO_3$, $Cs_2CO_3$, and $NaHCO_3$). Where the starting material is Compound (J), $KHCO_3$ or preformed potassium, sodium, and cesium salts of Compound (J) may also be used.

Alternative solvents can include 2-methyltetrahydrofuran, tetrahydrofuran, isopropyl acetate, ethyl acetate, tert-butyl methyl ether, cyclopentyl methyl ether, dimethylformamide, acetone, MEK, and MIBK.

The reaction temperature may range from about 10° C. to about 60° C.

2nd Alkylation: Conversion of Compound (G-a) to Compound (B-a):

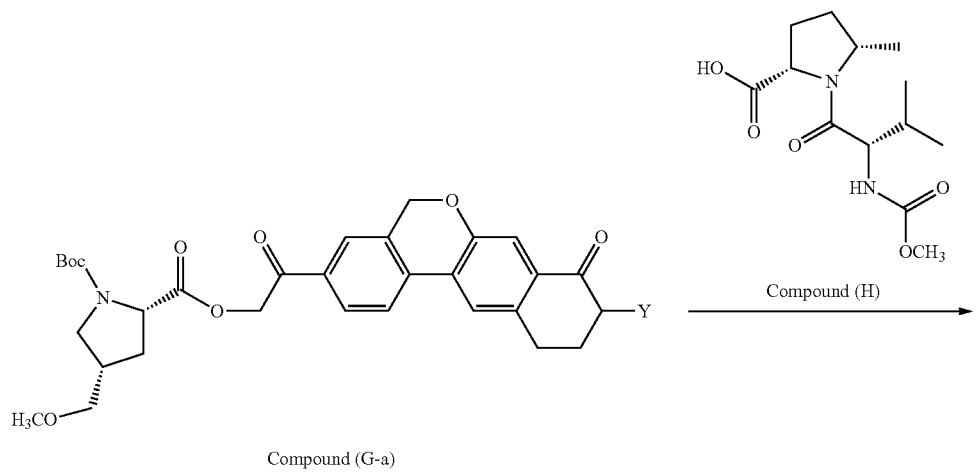

Compound (G-a)

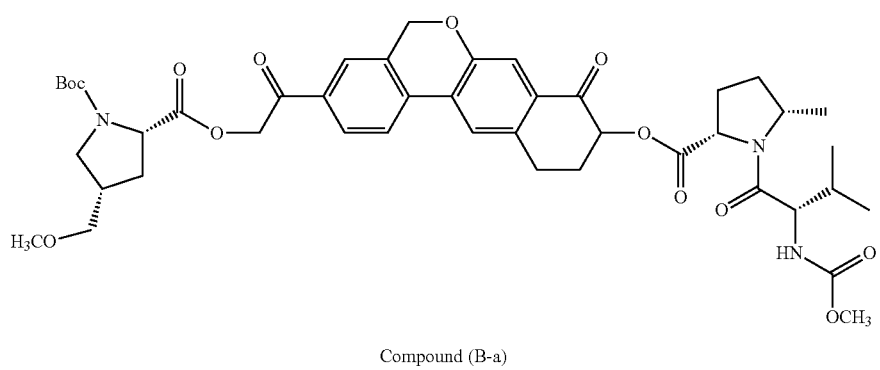

Compound (B-a)

Y = Br

A solution of Compound (G-a) (prepared as described earlier starting from 45 g of Compound (I-a)) was mixed with Compound (H) (42.9 g, 1.5 equiv.), and cesium carbonate (26.1 g, 0.8 equiv.). The reaction mixture was stirred at about 40-45° C. until reaction was complete and then cooled to about 20° C. Water (450 mL) and ethyl acetate (225 mL) were added and the mixture was agitated. Layers were separated, and the aqueous layer was extracted with ethyl acetate (150 mL). Combined organic phase was concentrated and solvent was swapped to toluene. A purified sample of Compound (B-a) has the following spectrum: $^1$H NMR (400 MHz, CDCl$_3$) δ7.90-7.93 (m, 1H), 7.81-7.83 (m, 1H), 7.73 (s, 1H), 7.63-7.64 (d, 1H), 7.59-7.60 (d, 1H), 5.52-5.63 (m, 1H), 5.30-5.43 (q, 1H), 5.13-5.23 (s+m, 3H), 4.56-4.64 (m, 2H), 4.39-4.48 (m, 1H), 4.20-4.27 (m, 1H), 3.62-3.79 (m, 2H), 3.66 (s, 2H), 3.36-3.45 (m, 2H), 3.34-3.35 (d, 3H), 3.07-3.25 (m, 3H), 2.59-2.37 (m, 5H), 1.97-2.16 (m, 3H), 1.60 (s, 3H), 1.38-1.45 (m, 12H), 0.91-1.03 (m, 6H).

Alternative reagents and reaction conditions to those disclosed above may also be employed. For example, alternative starting material may include Compound (G) where Y may be —Cl, —Br, —OTs, —OSO$_2$Ph, —OSO$_2$Me, —OSO$_2$CF$_3$, —OSO$_2$R, or —OP(O)(OR)$_2$. where R is alkyl, aryl, or substituted aryl. In some embodiments, the substituted aryl may be an aryl having one or more substituents, such as alkyl, alkoxy, hydroxyl, nitro, halogen, and others as discussed above.

Various bases may be employed. Non-limiting examples can include phosphate salts (including but not limited to KH$_2$PO$_4$, K$_3$PO$_4$, Na$_2$HPO$_4$, and Na$_3$PO$_4$) and carbonate salts (including but not limited to K$_2$CO$_3$ or Na$_2$CO$_3$). If Compound (H) is used as the starting material, Li$_2$CO$_3$ or preformed potassium, sodium, and cesium salt of Compound (H) may be employed.

Alternative solvents may include 2-methyltetrahydrofuran, dichloromethane, toluene, mixtures of THF/Toluene, isopropyl acetate, ethyl acetate, 1-methyl-2-pyrrolidinone, N,N-dimethylacetamide, acetone, MEK, and MIBK. An alternative additive may be potassium iodide, and the reaction temperature may range from about 40° C. to about 60° C. or about 40° C. to about 50° C.

Cyclization: Conversion of Compound (B-a) to Compound (C-a)

oven to afford Compound (C-a). A purified sample of Compound (C-a) has the following spectrum: ¹H NMR (400

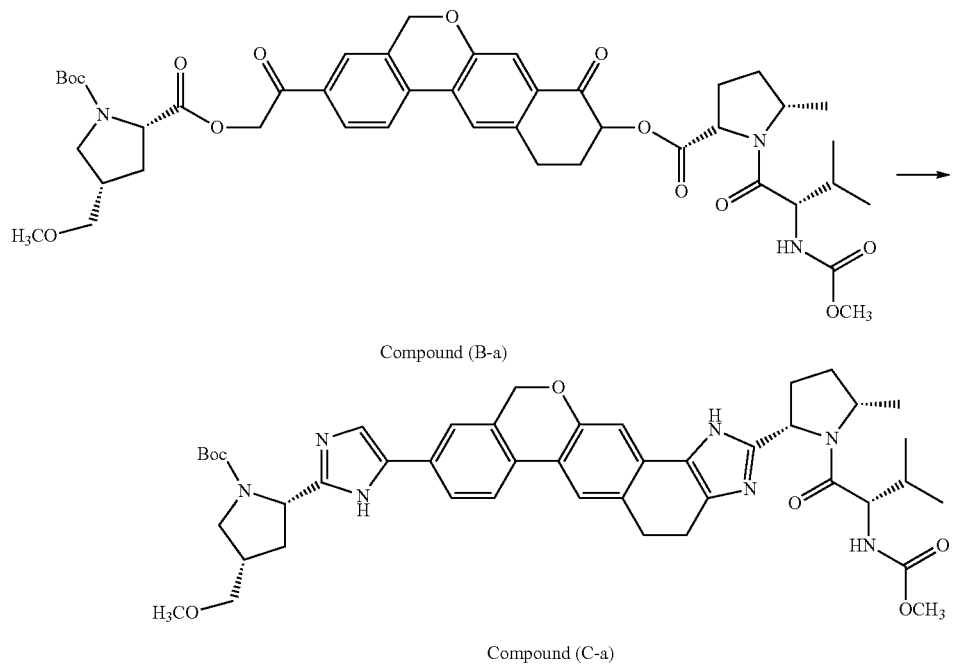

Compound (B-a)

Compound (C-a)

A toluene solution of Compound (B-a) (604 g solution from 45 g of Compound (I-a)) was charged to a reaction vessel containing ammonium acetate (185.2 g) and isopropanol (91.0 g). The contents of the reactor were agitated at about 90° C. until the reaction was complete (about 16 to 24 hours). The reaction mixture was cooled to about 45° C., and then allowed to settle for layer separation. Water (226 g) was added to the organic phase, and the resulting mixture was separated at about 30° C. Methanol (274 g), Celite (26.9 g) and an aqueous solution of sodium hydroxide (67.5 g, 50%) and sodium chloride (54.0 g) in water (608 g) were added to the organic phase, and the resulting mixture was agitated for a minimum of 30 minutes. The mixture was then filtered through Celite and rinsed forward with a mixture of toluene (250 g) and isopropanol (11 g). The biphasic filtrate was separated and water (223 g) was added to the organic phase, and the resulting mixture was agitated at about 30° C. for at least 15 minutes. The mixture was filtered through Celite and rinsed forward with toluene (91 g). The organic layer was concentrated by vacuum distillation to 355 g and was added over 30 minutes to another reactor containing n-heptane (578 g). The resulting slurry is filtered, with the wetcake was washed with n-heptane (450 mL) and dried in a vacuum MHz, CDCl₃) δ 12.27-11.60 (m, 1H), 11.18-10.69 (m, 1H), 7.83-7.44 (m, 4H), 7.36 (d, J=7.9 Hz, 1H), 7.28-7.05 (m, 1H), 5.65-5.25 (m, 1H), 5.25-4.83 (m, 4H), 4.34-4.03 (m, 2H), 3.93-3.63 (m, 4H), 3.52 (s, 1H), 3.35 (d, J=2.4 Hz, 4H), 3.19-2.94 (m, 4H), 2.88 (dd, J=12.0, 7.9 Hz, 3 H), 2.66-1.85 (m, 5H), 1.79 (s, 5H), 1.37-1.12 (m, 6H), 1.04-0.98 (m, 6H), 0.82 (t, J=7.7 Hz, 2H).

Alternative reagents and reaction conditions to those disclosed above may also be employed. For example, alternative reagents, in lieu of ammonium acetate, can include hexamethyldisilazane, ammonia, ammonium formate, ammonium propionate, ammonium hexanoate, and ammonium octanoate. Various solvents, such as toluene, xylene, an alcohol (including but not limited to isopropanol, 1-propanol, 1-butanol, 2-butanol, 2-methoxyethanol, and glycols, such as ethylene glycol and propylene glycol) may be employed. Alternative catalyst/additives may include magnesium stearate, acetic acid, propionic acid, and acetic anhydride. The reaction temperature may range from about 60° C. to about 110° C. or about 85° C. to about 95° C.

Dehydrogenation: Conversion of Compound (C-a) to Compound (D-a):

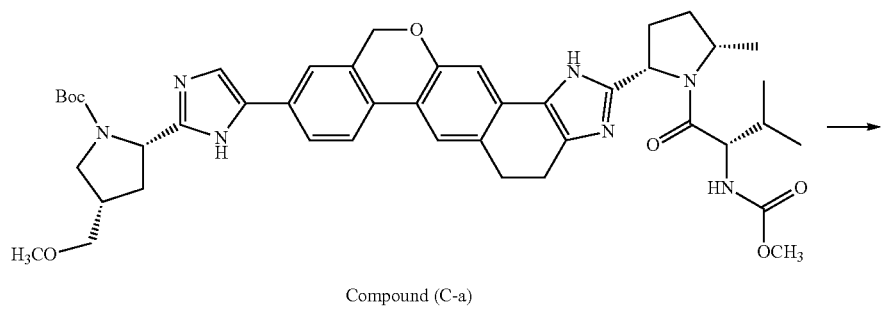

Compound (C-a)

-continued

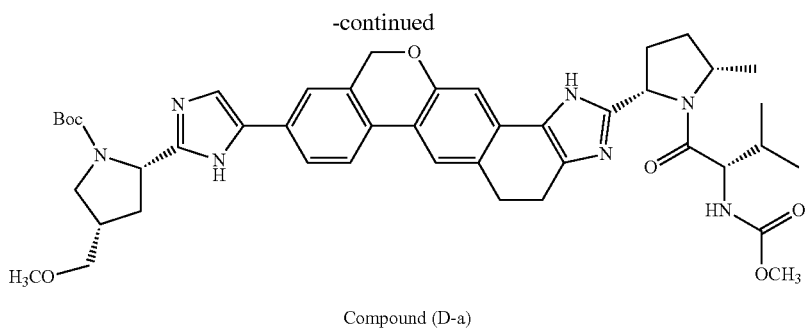

Compound (D-a)

Preparation of Compound (D-a) Using DDQ as Oxidant:

A solution of Compound (C-a) (255.84 g) in 2-methyltetrahydrofuran (1535 mL) was cooled to about 0° C. and acetic acid (0.92 mL) was added. To this mixture was added a solution of DDQ (76.98 g) in 2-methyltetrahydrofuran (385 mL) over about 30 minutes. Upon reaction completion, a 10 wt % aqueous potassium hydroxide solution (1275 mL) was added over about 30 minutes and the mixture was warmed to about 20° C. Celite (101.5 g) was added and the slurry was filtered through Celite (50.0 g) and the filter cake was rinsed with 2-methyltetrahydrofuran (765 mL). The phases of the filtrate were separated. The organic phase was washed successively aqueous potassium hydroxide solution (1020 mL, 10 wt %), aqueous sodium bisulfate solution (1020 mL, 10 wt %), aqueous sodium bicarbonate solution (1020 mL, 5 wt %) and aqueous sodium chloride solution (1020 mL, 5 wt %). The organic phase was then concentrated to a volume of about 650 mL. Cyclopentyl methyl ether (1530 mL) was added and the resulting solution was concentrated to a volume of about 710 mL. The temperature was adjusted to about 40° C. and Compound (D-a) seed (1.0 g) was added. The mixture was agitated until a slurry forms, then methyl tert-butyl ether (2300 mL) was added over about 3 hours. The slurry was cooled to about 20° C. over about 2 hours and filtered. The filter cake was rinsed with methyl tert-butyl ether (1275 mL) and dried in a vacuum oven at about 40° C. to provide Compound (D-a). A purified sample of Compound (D-a) has the following spectrum: $^1$H NMR (400 MHz, CDCl$_3$) δ 13.05-10.50 (comp m, 2H), 8.65-6.95 (comp m, 8H), 5.50-5.35 (m, 2H), 5.25-4.60 (comp m, 3H), 4.35-4.20 (m, 1H), 4.00-3.65 (comp m, 4H), 3.60-3.45 (m, 1H), 3.45-3.25 (comp m, 4H), 3.25-3.00 (comp m, 2H), 2.95-1.65 (comp m, 6H), 1.47 (br s, 9H), 1.40-1.25 (comp m, 2H), 1.20-0.70 (comp m, 9H).

Alternative Preparation of Compound (D-a) Using MnO$_2$ as Oxidant:

A mixture of Compound (C-a) (50.0 g), manganese (IV) oxide (152.8 g) and dichloromethane (500 mL) is stirred at about 20° C. Upon completion of the reaction, Celite (15 g) was added. The resulting slurry was filtered through Celite (20 g) and the filter cake was rinsed with dichloromethane (500 mL). The filtrate was concentrated and solvent exchanged into cyclopentyl methyl ether (250 mL). The resulting solution was warmed to about 60° C. and treated with an aqueous potassium hydroxide solution (250 mL, 10 wt %). The biphasic mixture is stirred at about 45° C. for about 12 hours. The phases are then separated and the organic phase is concentrated to a volume of about 150 mL. The concentrate is filtered, seeded with Compound (D-a) seed and agitated at about 40° C. to obtain a slurry. Methyl tert-butyl ether (450 mL) was added to the slurry over 30 minutes and the resulting mixture was cooled to about 20° C. The precipitated solid was filtered, rinsed with methyl tert-butyl ether (250 mL) and dried in a vacuum oven at about 40° C. to obtain Compound (D-a).

Alternative Preparation of Compound (D-a) Through Catalytic Dehydrogenation

A mixture of Compound (C-a) (2.5 g, 2.7 mmol, 1 equiv), 5% Pd/Al$_2$O$_3$ (2.5 g) and 1-propanol (25 mL, degassed) was stirred at reflux under inert environment for about 5.5 hours. The reaction mixture was then cooled to ambient temperature and filtered through Celite, and the residue rinsed with 1-propanol (2×5 mL) to obtain a solution of Compound (D-a).

Alternative reagents and reaction conditions to those disclosed above may also be employed. For example, in a reaction scheme employing stoichiometric oxidants, alternative oxidants may include manganese(IV) oxide, copper (II) acetate, copper(II) trifluoroacetate, copper(II) chloride, copper(II) bromide, bromine (Br$_2$), iodine (I$_2$), N-chlorosuccinimide, N-bromosuccinimide, N-iodosuccinimide, 1,4-benzoquinone, tetrachloro-1,4-benzoquinone (chloranil), ceric ammonium nitrate, hydrogen peroxide, tert-butyl hydroperoxide, di-tert-butyl peroxide, benzoyl peroxide, oxygen (O$_2$), sodium hypochlorite, sodium hypobromite, tert-butyl hypochlorite, Oxone, diacetoxyiodobenzene, and bis(trifluoroacetoxy)iodobenzene. Various additives may be employed, and non-limiting examples may be carbonate bases (e.g., potassium carbonate, potassium bicarbonate, sodium carbonate, sodium bicarbonate, and the like), amines (e.g., triethylamine, diisopropylethylamine and the like), and acids (e.g., trifluoroacetic acid, trichloroacetic acid, benzoic acid, hydrochloric acid, sulfuric acid, phosphoric acid, para-toluenesulfonic acid, methanesulfonic acid), sodium acetate, potassium acetate, and the like). The reaction temperature may range from about −10° C. to 80° C. The reaction may take place in solvents, such as halogenated solvents (e.g., dichloromethane, 1,2-dichloroethane, etc.), aromatic solvents (e.g., toluene, xylenes, etc.), ethereal solvents (tetrahydrofuran, 1,4-dioxane, cyclopentyl methyl ether, 1,2-dimethoxyethane, diglyme, triglyme, etc.), alcoholic solvents (e.g., methanol, ethanol, n-propanol, isopropanol, n-butanol, tert-butanol, tert-amyl alcohol, ethylene glycol, propylene glycol, etc.), ester solvents (e.g., ethyl acetate, isopropyl acetate, tert-butyl acetate, etc.), ketone solvents (e.g., acetone, 2-butanone, 4-methyl-2-pentanone, etc.), polar aprotic solvents (e.g., acetonitrile, N,N-dimethylformamide, N,N-dimethylacetamide, N-methyl-2-pyrrolidinone, pyridine, dimethyl sulfoxide, etc.), amine solvents (e.g., triethylamine, morpholine, etc.), acetic acid, and water.

In reaction schemes employing catalytic oxidants, alternative catalysts may include palladium catalysts (e.g., palladium(II) acetate, palladium(II) trifluoroacetate, palladium(II) chloride, palladium(II) bromide, palladium(II) iodide, palladium(II) benzoate, palladium(II) sulfate, tetrakis(triphenylphosphine)palladium(0), tris(dibenzylideneacetone)dipalladium(0), bis(tri-tert-butylphosphine)palladium(0), bis(triphenylphosphine)palladium(II) chloride, bis(acetonitrile)palladium(II) chloride, bis(benzonitrile)palladium(II) chloride, palladium on carbon, palladium on alumina, palladium on hydroxyapatite, palladium on calcium carbonate, palladium on barium sulfate, palladium(II) hydroxide on carbon), platinum catalysts (e.g., platinum on carbon, platinum(IV) oxide, chloroplatinic acid, potassium chloroplatinate), rhodium catalysts (e.g., rhodium on carbon, rhodium on alumina, bis(styrene)bis(triphenylphosphine)rhodium (0)), ruthenium catalysts (e.g., ruthenium(II) salen, dichloro(para-cymene)ruthenium(II) dimer), iridium catalysts (e.g., iridium(III) chloride, (1,5-cyclooctadiene)diiridium(I) dichloride, bis(1,5-cyclooctadiene)iridium(I) tetrafluoroborate, bis(triphenylphosphine)(1,5-cyclooctadiene)iridium(I) carbonyl chloride, bis(triphenylphosphine)(1,5-cyclooctadiene)iridium(I) tetrafluoroborate), copper catalysts (e.g., copper(I) chloride, copper(II) chloride, copper(I) bromide, copper(II) bromide, copper(I) iodide, copper(II) iodide, copper(II) acetate, copper(II) trifluoroacetate, copper(I) trifluoromethanesulfonate, copper(II) trifluoromethanesulfonate, copper(II) sulfate), iron catalysts (e.g., iron(II) sulfate, iron(II) chloride, iron(III) chloride), vanadium catalysts (e.g., dichloro(ethoxy)oxovanadium, dichloro(isopropoxy)oxovanadium), manganese catalysts (e.g., manganese(IV) oxide, manganese(III) (salen) chloride), cobalt catalysts (e.g., cobalt(II) acetate, cobalt(II) chloride, cobalt(II) salen), indium(III) chloride, silver(I) oxide, sodium tungstate, quinone catalysts (e.g., 2,3-dichloro-5,6-dicyano-1,4-benzoquinone, 1,4-benzoquinone, and tetrachloro-1,4-benzoquinone (chloranil)).

Alternative co-oxidants can include, but are not limited to, sodium nitrite, copper(II) acetate, sodium persulfate, potassium persulfate, ammonium persulfate, sodium perborate, nitrobenzenesulfonate, 2,2,6,6-tetramethylpiperidine-1-oxyl (TEMPO), pyridine-N-oxide, hydrogen peroxide, tert-butyl hydroperoxide, di-tert-butyl peroxide, benzoyl peroxide, oxygen ($O_2$), sodium hypochlorite, sodium hypobromite, tert-butyl hypochlorite, oxone, diacetoxyiodobenzene, and bis(trifluoroacetoxy)iodobenzene.

Various hydrogen acceptors may be employed. Non-limiting examples can include unsaturated hydrocarbons (e.g., tert-butylethylene, tert-butyl acetylene, 2-hexyne, cyclohexene, and the like), acrylate esters (e.g., methyl acrylate, ethyl acrylate, isopropyl acrylate, tert-butyl acrylate, and the like), maleate esters (e.g., dimethyl maleate, diethyl maleate, diisopropyl maleate, dibutyl maleate, and the like), fumarate esters (e.g., dimethyl fumarate, diethyl fumarate, diisopropyl fumarate, dibutyl fumarate, and the like), and quinones (e.g. chloranil, 1,4-benzoquinone, etc.).

Alternative additives may be employed, such as carbonate bases (e.g., potassium carbonate, potassium bicarbonate, sodium carbonate, sodium bicarbonate, etc.), amine bases (e.g., triethylamine, diisopropylethylamine, etc.), phosphines (e.g., triphenylphosphine, tri(ortho-tolyl)phosphine, tricyclohexylphosphine, tri-n-butylphosphine, tri-tert-butylphosphine, etc.), acids (e.g., trifluoroacetic acid, trichloroacetic acid, benzoic acid, hydrochloric acid, sulfuric acid, phosphoric acid, para-toluenesulfonic acid, methanesulfonic acid, etc.), sodium acetate, N-hydroxyphthalimide, salen, 2,2'-bipyridine, 9,10-phenanthroline, and quinine.

The reaction can proceed at temperatures ranging from about 10° C. to about 120° C. Various solvents can be employed, including but not limited to halogenated solvents (e.g., dichloromethane, 1,2-dichloroethane, and the like), aromatic solvents (e.g., toluene, xylenes, and the like), ethereal solvents (tetrahydrofuran, 1,4-dioxane, cyclopentyl methyl ether, 1,2-dimethoxyethane, diglyme, triglyme, and the like), alcoholic solvents (e.g., methanol, ethanol, n-propanol, isopropanol, n-butanol, tert-butanol, tert-amyl alcohol, ethylene glycol, propylene glycol, and the like), ester solvents (e.g., ethyl acetate, isopropyl acetate, tert-butyl acetate, and the like), ketone solvents (e.g., acetone, 2-butanone, 4-methyl-2-pentanone, and the like), polar aprotic solvents (e.g., acetonitrile, N,N-dimethylformamide, N,N-dimethylacetamide, N-methyl-2-pyrrolidinone, pyridine, dimethyl sulfoxide, and the like), amine solvents (e.g., triethylamine, morpholine, and the like), acetic acid, and water.

Deprotection: Conversion of Compound (D-a) to Compound (E-a):

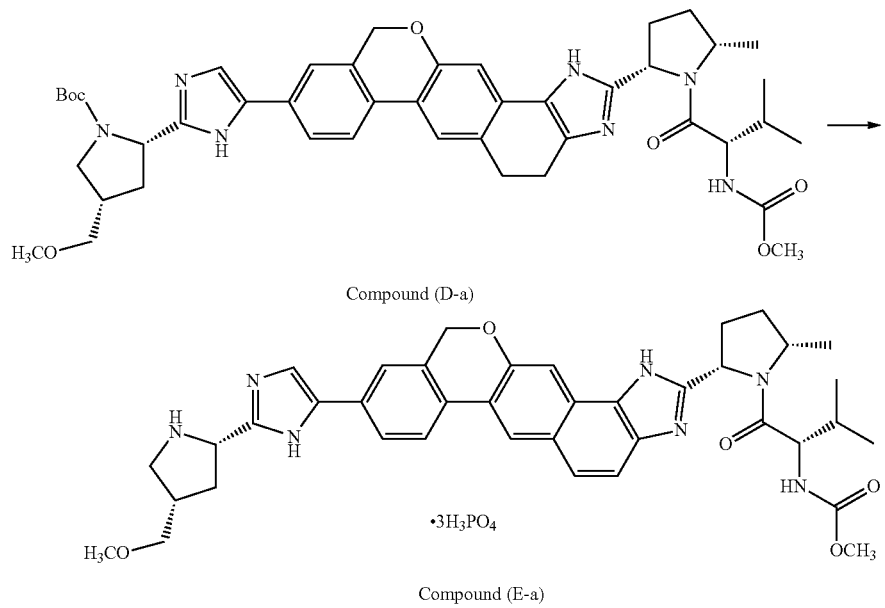

Compound (D-a)

Compound (E-a)

Acetyl chloride (135 mL, 5 equiv.) was added slowly to methanol (750 mL) under external cooling maintaining reaction temperature below 30° C. The resulting methanolic hydrogen chloride solution was cooled to about 20° C., and added slowly over about 1 hour to a solution of Compound (D-a) (300 g, 1 equiv.) in methanol (750 mL) held at about 60° C., and rinsed forward with methanol (300 mL). The reaction mixture was agitated at about 60° C. until reaction was complete (about 1 hour), and then cooled to about 5° C. The reaction mixture was adjusted to pH 7-8 by addition of sodium methoxide (25 wt. % solution in methanol, 370 mL) over about 20 minutes while maintaining reaction temperature below about 20° C. Phosphoric acid (85 wt. %, 26 mL, 1 equiv.) and Celite (120 g) were added to the reaction mixture, which was then adjusted to about 20° C., filtered, and the filter cake was rinsed with methanol (1050 mL). The combined filtrate was polish filtered and treated with phosphoric acid (85 wt. %, 104 mL, 4 equiv.). The mixture was adjusted to about 60° C., seeded with Compound (E-a) seed crystals (1.5 g), aged at about 60° C. for 4 hours and cooled slowly to about 20° C. over about 7.5 hours. The precipitated product was filtered, washed with methanol (2×600 mL), and dried in a vacuum oven at about 45° C. to provide Compound (E-a). $^1$H NMR (400 MHz, D$_2$O) δ 7.53-6.77 (comp m, 8H), 5.24-4.80 (comp m, 3H), 4.59-4.38 (comp m, 2H), 4.15-3.90 (m, 1H), 3.65-3.38 (comp m, 5H), 3.36-3.14 (comp m, 4H), 2.75 (s, 1H), 2.87-2.66 (m, 1H), 2.29-1.60 (comp m, 6H), 1.27 (d, 3H), 0.76 (m, 6H).

Alternative reagents and reaction conditions to those disclosed above may also be employed. Various deprotection agents are well known to those skilled in the art and include those disclosed in T. W. Greene & P. G. M. Wuts, *Protective Groups in Organic Synthesis* (4th edition) J. Wiley & Sons, 2007, hereby incorporated by reference in its entirety. For example, a wide range of acids may be used, including but not limited to phosphoric acid, trifluoroacetic acid, p-toluenesulfonic acid, methanesulfonic acid, ethanesulfonic acid, benzenesulfonic acid, p-toluenesulfonic acid, 4-bromobenzenesulfonic acid, thionyl chloride, and trimethylsilyl chloride. A wide range of solvents may be employed, including but not limited to water, ethanol, acetonitrile, acetone, tetrahydrofuran, 1,4-dioxane, and toluene. Deprotection may proceed at temperatures ranging from about 20° C. to about 110° C. or from about 55° C. to about 65° C.

A wide range of bases may be employed as a neutralization reagent. Non-limiting examples can include sodium phosphate dibasic, potassium phosphate dibasic, potassium bicarbonate, lithium hydroxide, sodium hydroxide, potassium hydroxide, triethylamine, N, N-diisopropylethylamine, and 4-methylmorpholine. Various solvents may be used for neutralization, such as water, ethanol, 1-propanol, 2-propanol, 1-butanol, 2-butanol, acetone, acetonitrile, 2-butanone, 4-methyl-2-pentanone, tetrahydrofuran, 2-methyltetrahydrofuran, 1,4-dioxane, ethyl acetate, isopropyl acetate, dichloromethane, and dichloroethane. Neutralization may proceed at temperatures ranging from about −20° C. to about 60° C. or about 5° C. to about 15° C.

Various crystallization reagents can be employed. Non-limiting examples may be hydrochloric acid, hydrobromic acid, sulfuric acid, ethanesulfonic acid, benzenesulfonic acid, 4-bromobenzenesulfonic acid, oxalic acid, and glucuronic acid. Solvents for crystallization can include, but is not limited to, water, ethanol, 1-propanol, 2-propanol, and acetonitrile. Crystallization may proceed at temperatures ranging from about −20° C. to about 100° C.

Free-Basing of Compound (E-a) to Prepare Compound (E)

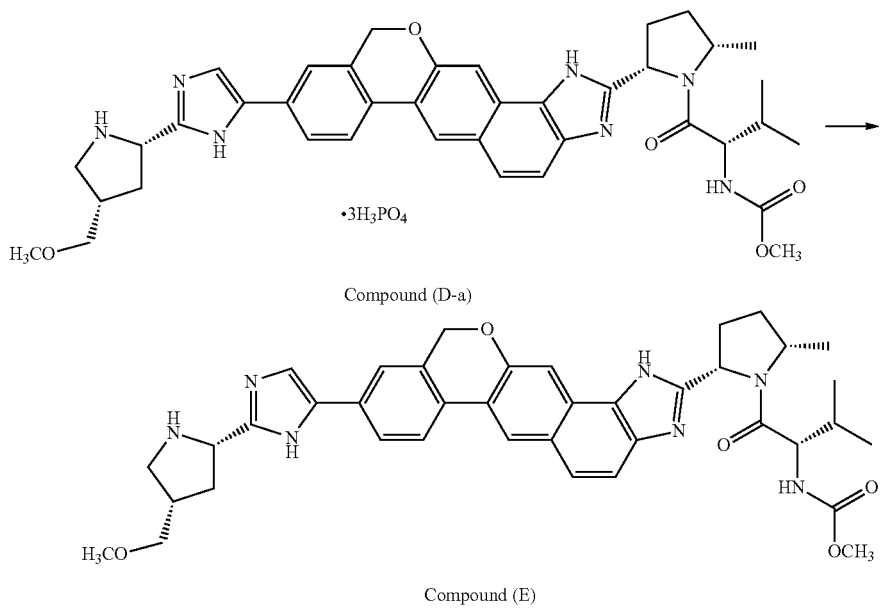

Compound (D-a)

Compound (E)

Compound (E-a) (10.0 g, 10.1 mmol) was dissolved in water (100 g) and then dichloromethane (132 g) and 28% ammonium hydroxide (7.2 g) were added sequentially. The biphasic mixture was stirred for 45 minutes. Celite (2.2 g) was added, the mixture was filtered through a bed of additional Celite (5.1 g), and the phases were then separated. The lower organic phase was washed with water (50 g), filtered, and then concentrated by rotary evaporation to produce Compound (E). $^1$H NMR (400 MHz, CD$_3$OD) δ 8.35-7.17 (m, 8H), 5.6-4.68 (m, 3H), 4.41-3.96 (m, 2H), 3.96-3.72 (br s, 1H), 3.74-3.48 (m, 2H), 3.42 (d, 2H), 3.33 (s, 3H), 3.28 (s, 1H), 3.19-3.01 (m, 1H), 3.00-2.79 (m, 1H), 2.69-1.82 (m, 6H), 1.80-1.45 (m, 3H), 1.21-0.73 (m, 8H).

Alternative reagents and reaction conditions to those disclosed above may also be employed. For example, tris-hydrochloride salts of Compound (E) may be used. Various bases may be employed, such as sodium carbonate, potassium carbonate, sodium hydroxide, and potassium hydroxide. Various solvents, such as 2-methyltetrahydrofuran and ethyl acetate, may be employed. The temperature may range from about 15° C. to about 25° C.

Alternative Free-Basing of Compound (E-b) to Prepare Compound (E)

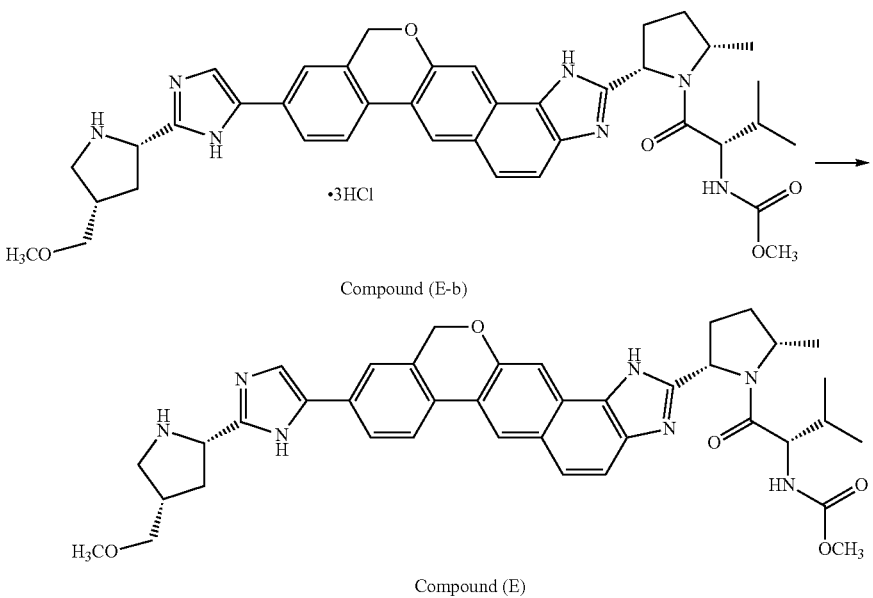

Compound (E-b)

Compound (E)

Compound (E-b) (15.2 g) was dissolved in water (100 g) and then dichloromethane (132 g) and 28% ammonium hydroxide (7.4 g) were added sequentially. The biphasic mixture was stirred for about 45 minutes. Celite (2.1 g) was added, the mixture was filtered through a bed of additional Celite (5.2 g), and the phases were then separated. The lower organic phase was washed with water (50 g), filtered, and then concentrated by rotary evaporation to produce Compound (E). ¹H NMR (400 MHz, CD₃OD) δ 7.92-6.73 (m, 8H), 5.51-4.90 (m, 2H), 4.63-4.30 (m, 3H), 4.21-3.78 (m, 1H), 3.73-3.46 (m, 5H), 3.40-3.19 (m, 4H), 3.07-2.49 (m, 3H), 2.41-1.61 (m, 6H), 1.44-1.14 (m, 2H), 1.04-0.55 (m, 7H).

Salt Conversion of Compound (E-a) to Compound (E-b)

(58 g) was charged to the reactor during which time a slurry formed. The slurry was stirred for about 21 h and then additional acetonitrile (39 g) was added. The slurry was cooled to about 0° C., held for about 60 min and the solids were then isolated by filtration, rinsed with 7% (w/w) water in acetonitrile (22 g) previously cooled to about 5° C. The wet cake was partially deliquored to afford Compound (E-b). ¹H NMR (400 MHz, D₂O) δ 7.92-6.73 (m, 8H), 5.51-4.90 (m, 2H), 4.63-4.30 (m, 3H), 4.21-3.78 (m, 1H), 3.73-3.46

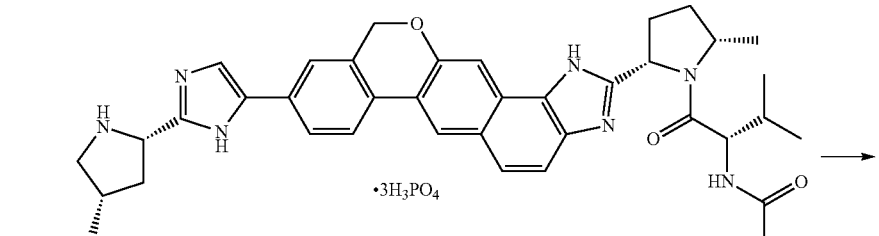

Compound (E-a)

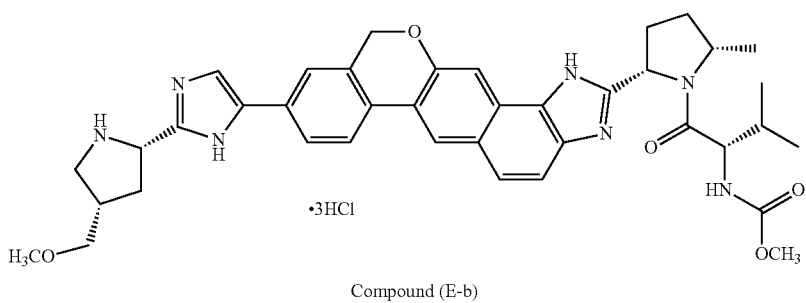

Compound (E-b)

A solution of Compound (E-a) (10.0 g, 10.1 mmol), a solution of 37% HCl (10 g) in water (20 g), and acetonitrile (30 g) was warmed to about 50° C. and agitated for about 1 h. The solution was cooled to about 20° C. and acetonitrile (m, 5H), 3.40-3.19 (m, 4H), 3.07-2.49 (m, 3H), 2.41-1.61 (m, 6H), 1.44-1.14 (m, 2H), 1.04-0.55 (m, 7H).

Coupling Reaction of Compound (E) and Compound (F) to Prepare Compound (A)

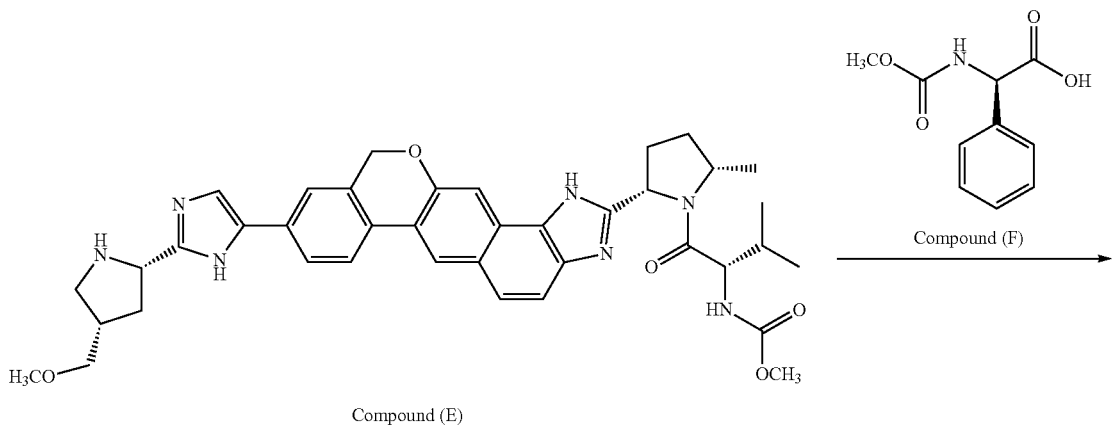

Compound (E)

Compound (F)

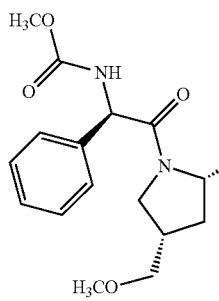
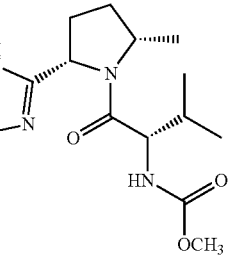

Compound (A)

A flask was charged sequentially with 2-chloro-4,6-bis[3-(perfluorohexyl)propyloxy]-1,3,5-triazine ("CDMT") (2.2 g/v) and methanol (8.9 g) and the slurry was cooled to about 0° C. To the mixture was added NMM (1.3 g) over about 5 minutes, maintaining an internal temperature of less than 20° C. The solution was stirred for about 20 minutes to produce a solution of 4-(4,6-dimethoxy-1,3,5-triazin-2-yl)-4-methylmorpholinium chloride in methanol.

To a solution of Compound (E) (7.1 g) in dichloromethane (170 g) was added Compound (F) (2.8 g). The solution of 4-(4,6-dimethoxy-1,3,5-triazin-2-yl)-4-methylmorpholinium chloride in methanol was added over 2 minutes followed by a rinse of methanol (1.1 g). After about 2.5 h, the completed reaction solution was washed sequentially with aqueous 10% potassium bicarbonate solution (40 mL), 3% hydrochloric acid (40 mL), and aqueous 10% potassium bicarbonate solution (40 mL). The lower organic phase was washed with water (40 mL), filtered, and then concentrated by rotary evaporation to produce Compound (A). $^1$H NMR (400 MHz, CD$_3$OD) δ 8.56-6.67 (m, 13H), 5.76-4.94 (m, 4H), 4.86-4.67 (m, 1H), 4.47-3.98 (m, 1H), 3.98-2.72 (m, 15H), 2.74-1.77 (m, 7H), 1.77-1.40 (m, 2H), 1.39-0.53 (m, 8H).

Alternative reagents and reaction conditions to those disclosed above may also be employed. For example, tris-phosphate salts or tris-hydrochloride salts of Compound (G) may be used as alternative starting material. The reaction may take place at a temperature range of from about 10° C. to about 20° C. Alternative coupling agents include, but are not limited to, EDC/HOBt, HATU, HBTU, TBTU, BOP, PyClOP, PyBOP, DCC/HOBt, COMU, EDCI/Oxyma, T3P, and 4-(4,6-dimethoxy-1,3,5-triazin-2-yl)-4-methylmorpholinium tetrafluoroborate. An alternative bases that may be employed can be diisopropylethylamine. The reaction may proceed in DMF and at temperatures ranging from about −20° C. to about 30° C.

Salt Formation and Crystallization of Compound (A)
Crystallization of Compound (A-a)

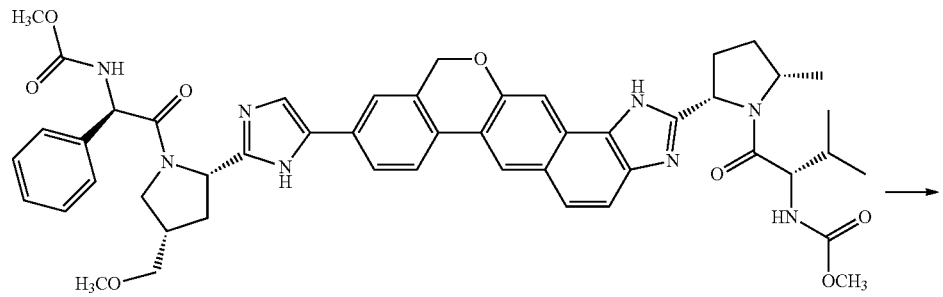

Compound (A)

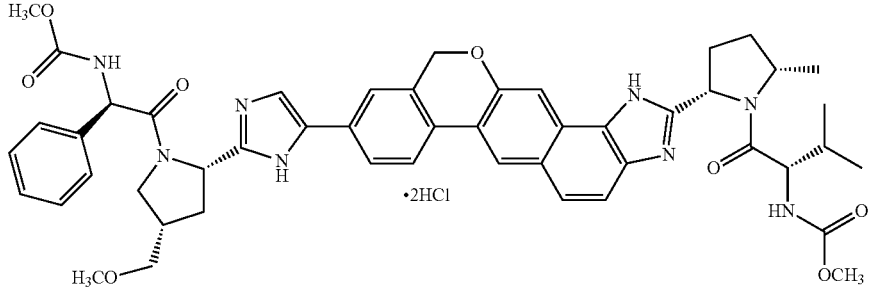

Compound (A-a)

A flask was charged with Compound (A) (10 g) and ethanol (125 mL) and was then warmed to about 45° C. Concentrated hydrochloric acid (2.3 mL) was added followed by Compound (A-a) seed crystals (5 mg). The mixture was cooled to about 20° C. over about 5 h and held for about an additional 11 h. The solids were isolated by filtration, washed with ethanol (2×20 mL), and deliquored to produce Compound (A-a). ¹H NMR (400 MHz, CD₃OD) δ 8.94-7.22 (m, 14H), 5.78-5.11 (m, 5H), 4.53-4.04 (m, 1H), 3.99-3.57 (m, 10H), 3.57-3.41 (m, 2H), 2.99-2.24 (m, 5H), 2.24-1.85 (m, 3H), 1.80-1.50 (m, 2H), 1.39-0.73 (m, 8H).

Alternative Crystallization of Compound (A-b)

3H), 4.60-4.32 (m, 2H), 4.29-3.76 (m, 1H), 3.70-2.75 (m, 14H), 2.66-1.51 (m, 8H), 1.51-1.09 (m, 3H), 1.05-0.45 (m, 7H).

Alternative reagents and reaction conditions to those disclosed above may also be employed. For example, alternative acids may be hydrochloric acid, hydrobromic acid,

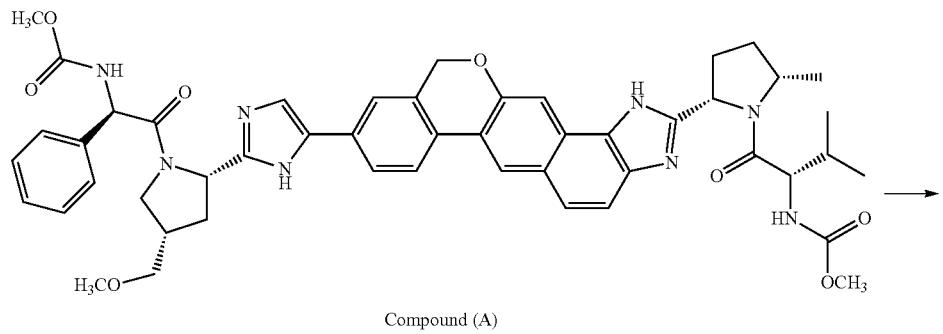

Compound (A)

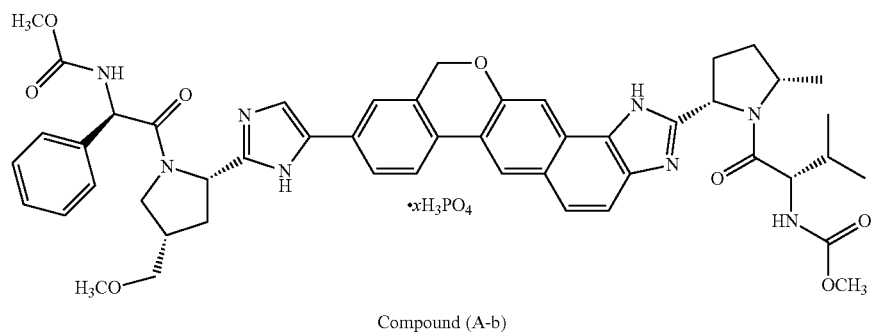

Compound (A-b)

A reaction vessel was charged with Compound (A) (25.0 g) followed by ethanol (125 mL) and 10% H₃PO₄ (250 mL). The solution was seeded with Compound (A-b) (100 mg) and stirred for about 17.5 h. The solids were isolated by filtration, washed with ethanol (2×5 mL), deliquored, and dried in a vacuum oven to produce Compound (A-b). ¹H NMR (400 MHz, D₂O) δ 7.76-6.48 (m, 13H), 5.53-4.90 (m, L-tartaric acid. Various solvents may be employed, such as methanol, ethanol, water, and isopropanol. The reaction may proceed at temperatures ranging from about 5° C. to about 60° C.

Free-Basing of Compound (A)

Free-Basing of Compound (A-a) to Prepare Compound (A)

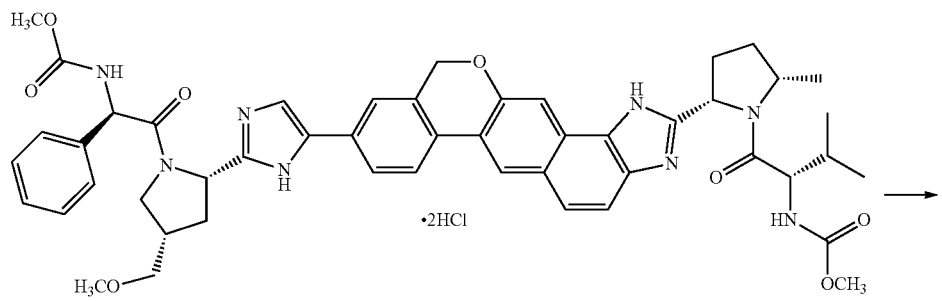

Compound (A-a)

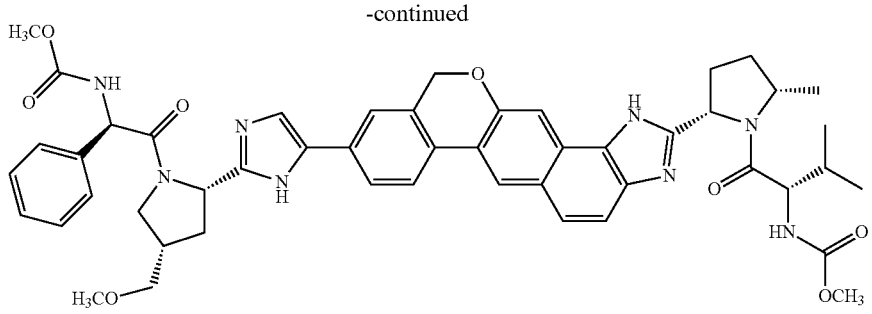

Compound (A)

A reaction vessel was charged with Compound (A-a) (18.2 g) followed by ethyl acetate (188 g) and 10% potassium bicarbonate (188 g) and the mixture was stirred for about 25 minutes. The phases were separated and the upper organic phase was then washed with water (188 mL). The resulting organic solution was concentrated, ethanol (188 g) was added, and the solution was evaporated to produce a concentrate (75 g). The resulting concentrate added into water (376 g) to produce a slurry. The solids were isolated by filtration, washed with water (38 g), deliquored and dried in a vacuum oven at about 50° C. to produce Compound (A). Alternative Free-Basing of Compound (A-b) to Prepare Compound (A)

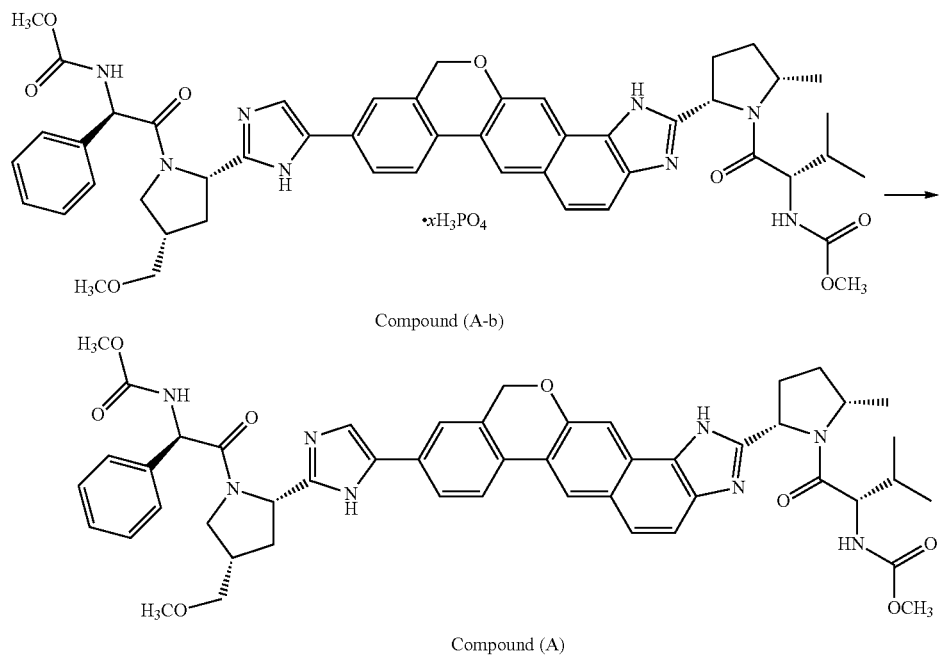

Compound (A-b)

Compound (A)

A reaction vessel was charged with Compound (A-b) (3.0 g) followed by EtOAc (15 mL) and 10% KHCO$_3$ (15 mL) and agitation was initiated. After about 5 h, the phases were separated and the organic phase was washed with water (15 mL) and then concentrated by rotary evaporation under vacuum. The residue was taken up in EtOH (4.5 mL) and then added to water (30 mL) to produce a slurry. After about 15 min, the solids were isolated by filtration rinsing forward water (3×3 mL). The solids were dried at about 50 to 60° C. vacuum oven for about 15 h to produce Compound (A).

Alternative reagents and reaction conditions to those disclosed above may also be employed. For example, an alternative base may be ammonium hydroxide or dibasic potassium phosphate. Various solvents may be employed, such as ethanol and water. The reaction may proceed at temperatures ranging from about 15° C. to about 25° C.

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms or methyl groups can be omitted from the drawn structures consistent with accepted shorthand notation of such organic compounds, and that one skilled in the art of organic chemistry would readily appreciate their presence. All patents and publications cited herein are hereby incorporated by reference in their entirety.

The invention claimed is:

1. A method for preparing a compound of formula (I-a), stereoisomer thereof, or mixture of stereoisomers thereof:

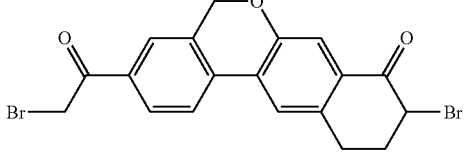
(I-a)

comprising the steps of:
(a) cyclizing a compound of formula (L):

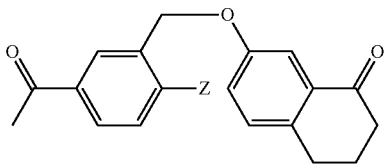
(L)

under conditions sufficient to yield a compound of formula (K):

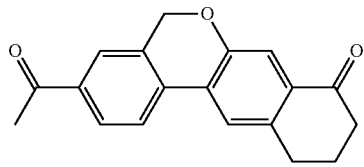
(K)

and
(b) brominating the compound of formula (K) under conditions sufficient to yield a compound of formula (I-a),
wherein Z is hydrogen, halo, —OSO$_2$R$^1$, —BF$_3^-$, —B(OR$^2$)$_2$, —CO$_2$H, or —NR$^1_3$ wherein R$^1$ is alkyl, haloalkyl, aryl, substituted aryl, heteroaryl, or substituted heteroaryl, and each R$^2$ is independently alkyl.

2. The method of claim 1, wherein the reaction conditions of step (a) comprise a solvent selected from the group consisting of N,N-dimethylacetamide, N,N-dimethylformamide, and acetonitrile.

3. The method of claim 1, wherein the reaction conditions of step (a) comprise a temperature of from about 20° C. to about 80° C.

4. The method of claim 1, wherein the reaction conditions of step (a) comprise at least one of a palladium catalyst, a carbonate salt, and a phosphine reagent.

5. The method of claim 1, wherein the reaction conditions of step (b) comprise a brominating reagent selected from the group consisting of pyridiniumtribomide, bromine, and N-bromosuccinimide.

6. The method of claim 1, wherein the reaction conditions of step (b) comprise a solvent selected from the group consisting of dichloromethane, methanol, and a mixture thereof.

7. The method of claim 1, wherein the reaction conditions of step (b) comprise a temperature of about 20° C.

8. The method of claim 1, wherein the compound of formula (L):

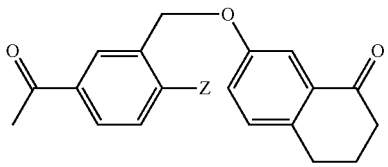
(L)

is prepared by contacting a compound of formula (M):

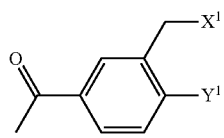
(M)

with a compound of formula (N):

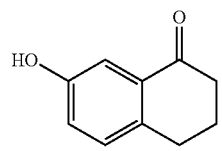
(N)

under conditions sufficient to yield the compound of formula (L),
wherein X$^1$ is a leaving group, Y$^1$ is hydrogen, halo or trifluoromethanesulfonate, and Z is hydrogen, halo, —OSO$_2$R$^1$, —BF$_3^-$, —B(OR$^2$)$_2$, —CO$_2$H, or —NR$^1_3$ wherein R$^1$ is alkyl, haloalkyl, aryl, substituted aryl, heteroaryl, or substituted heteroaryl, and each R$^2$ is independently alkyl.

9. The method of claim 8, wherein X$^1$ is halo, —OH, or —S(O)$_2$R$^3$, and R$^3$ is alkyl, haloalkyl, or aryl, and the aryl is optionally substituted with halo, alkyl, or haloalkyl.

10. The method of claim 8, wherein the reaction conditions comprise a solvent selected from the group consisting of N,N-dimethylacetamide, tetrahydrofuran, 2-methyltetrahydrofuran, N,N-dimethylformamide, and acetonitrile.

11. The method of claim 8, wherein the reaction conditions comprise a temperature of from about 20° C. to about 70° C.

12. A compound of formula (L):

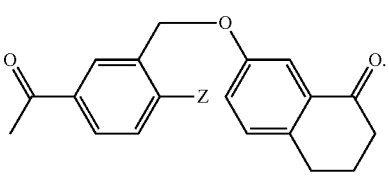
(L)

wherein Z is hydrogen, halo, —OSO$_2$R$^1$, —BF$_3^-$, —B(OR$^2$)$_2$, —CO$_2$H, or —NR$^1_3$ wherein R$^1$ is alkyl, haloalkyl, aryl, substituted aryl, heteroaryl, or substituted heteroaryl, and each R$^2$ is independently alkyl.

13. The compound of claim 12, wherein Z is bromo.

14. The method of claim 8 where the compound of formula (M):

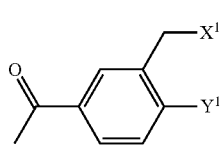
(M)
is prepared by reacting a compound of formula (M'):
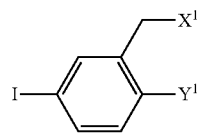
(M')
with isopropylmagnesium chloride in THF and N-methoxy-N-methyl acetamide to form formula (M); wherein $X^1$ is a leaving group and $Y^1$ is hydrogen, halo or trifluoromethanesulfonate.
* * * * *

UNITED STATES PATENT AND TRADEMARK OFFICE
CERTIFICATE OF CORRECTION

PATENT NO.         : 9,890,134 B2                       Page 1 of 1
APPLICATION NO.    : 15/582224
DATED              : February 13, 2018
INVENTOR(S)        : Kevin M. Allan et al.

It is certified that error appears in the above-identified patent and that said Letters Patent is hereby corrected as shown below:

In the Claims

In Claim 8, Column 146, Line 35, please replace "–B(OR$^2$)$_2$,–CO$_2$H," with -- –B(OR$^2$)$_2$, –CO$_2$H, --

In Claim 12, Column 146, Line 55, please replace " 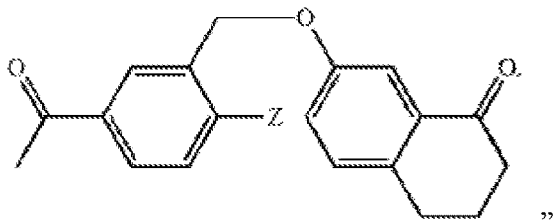 "

with -- 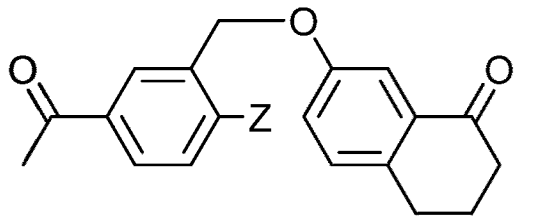 --

Signed and Sealed this
Sixteenth Day of July, 2019

Andrei Iancu
*Director of the United States Patent and Trademark Office*

UNITED STATES PATENT AND TRADEMARK OFFICE
CERTIFICATE OF CORRECTION

PATENT NO. : 9,890,134 B2
APPLICATION NO. : 15/582224
DATED : February 13, 2018
INVENTOR(S) : Kevin M. Allan et al.

Page 1 of 1

It is certified that error appears in the above-identified patent and that said Letters Patent is hereby corrected as shown below:

In the Specification

In Columns 129-130, please replace " 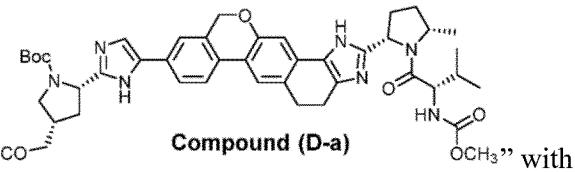" with

"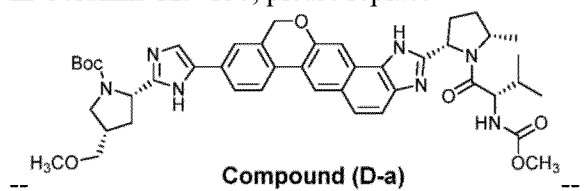"

In Columns 133-134, please replace "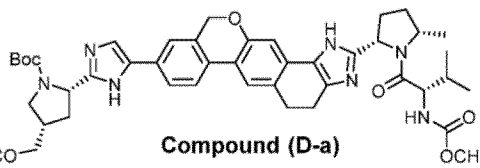" with

"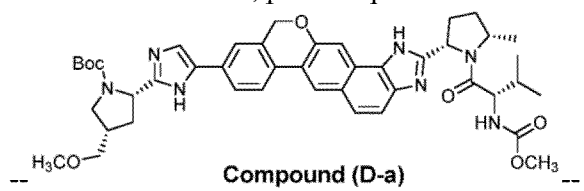"

Signed and Sealed this
Sixteenth Day of June, 2020

Andrei Iancu
*Director of the United States Patent and Trademark Office*